United States Patent
Tomishima et al.

(10) Patent No.: US 6,521,643 B1
(45) Date of Patent: Feb. 18, 2003

(54) PYRIDINE COMPOUNDS AND THEIR PHARMACEUTICAL USE

(75) Inventors: Masaki Tomishima, Osaka (JP); Kazuhiko Take, Tondabayashi (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/913,715

(22) PCT Filed: Feb. 14, 2000

(86) PCT No.: PCT/JP00/00772

§ 371 (c)(1),
(2), (4) Date: Aug. 17, 2001

(87) PCT Pub. No.: WO00/49015

PCT Pub. Date: Aug. 24, 2000

(30) Foreign Application Priority Data

Feb. 17, 1999 (AU) .................................. 8737

(51) Int. Cl.[7] ...................... A61K 31/44; C07D 401/00; C07D 401/14
(52) U.S. Cl. ..................... 514/336; 514/340; 514/342; 514/343; 514/345; 514/354; 546/268.4; 546/276.4; 546/279.7; 546/281.7; 546/290; 546/304; 546/314; 546/339
(58) Field of Search .................. 514/336, 340, 514/342, 343, 345, 354; 546/268.4, 276.4, 279.7, 281.7, 290, 304, 314, 339

(56) References Cited

U.S. PATENT DOCUMENTS 3,969,526 A * 7/1976 Gyurik et al.
4,005,202 A * 1/1977 Beard et al.

FOREIGN PATENT DOCUMENTS

| DE | 2411295 | * | 9/1974 |
| DE | 2635326 | * | 2/1977 |
| EP | 0 094 727 | * | 5/1983 |
| EP | 0 117 082 | * | 1/1984 |
| WO | WO 92/16526 | | 10/1992 |
| WO | 92/16526 | * | 10/1992 |
| WO | WO 96/18616 | | 6/1996 |
| WO | 96/18616 | * | 6/1996 |
| WO | WO 98/27108 | | 6/1998 |
| WO | 98/27108 | * | 6/1998 |

OTHER PUBLICATIONS

CA 89:43241, 1978, Raeymaekers.*

* cited by examiner

Primary Examiner—D. Margaret Seaman
(74) Attorney, Agent, or Firm—Oblon, Spivak, McClelland, Maier & Neustadt, P.C.

(57) ABSTRACT

A compound of formula (I) wherein each symbol is as defined in the specification, and pharmaceutically acceptable salts thereof. The compound (I) of the present invention and pharmaceutically acceptable salts thereof possess a strong inhibitory activity on the production of nitric oxide (NO), and are useful for prevention and/or treatment of NOS(nitric oxide synthasey)-mediated diseases such as adult respiratory distress syndrome, myocarditis, synovitis, septic shock, insulin-ependent diabetes mellitus, ulcerative colitis, cerebral infarction, rheumatoid arthritis, osteoarthritis, osteoporosis, systemic lupus erythematosus, rejection by organ transplantation, asthma, pain, ulcer, and the like in human being and animals.

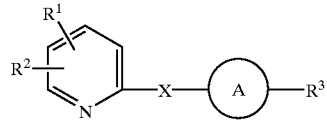

(I)

11 Claims, No Drawings

PYRIDINE COMPOUNDS AND THEIR PHARMACEUTICAL USE

TECHNICAL FIELD

This invention relates to new pyridine compounds. More particularly, this invention relates to new pyridine compounds and pharmaceutically acceptable salts thereof which have pharmacological activities, a process for preparation thereof, a pharmaceutical composition comprising the same and a use of the same.

Accordingly, one object of this invention is to provide the new and useful pyridine compounds and pharmaceutically acceptable salts thereof which possess a strong inhibitory activity on the production of nitric oxide (NO).

Another object of this invention is to provide a process for the preparation of the pyridine compounds and salts thereof.

A further object of this invention is to provide a pharmaceutical composition comprising said pyridine compound or a pharmaceutically acceptable salt thereof.

Still further object of this invention is to provide a use of said pyridine compounds or pharmaceutically acceptable salts thereof as a medicament for prophylactic and therapeutic treatment of nitric oxide synthase (NOS)-mediated diseases such as adult respiratory distress syndrome, myocarditis, synovitis, septic shock, insulin-dependent diabetes mellitus, ulcerative colitis, cerebral infarction, rheumatoid arthritis, osteoarthritis, osteoporosis, systemic lupus erythematosus, rejection by organ transplantation, asthma, pain, ulcer, and the like in human being and animals.

DISCLOSURE OF INVENTION

The object pyridine compounds of the present invention are novel and can be represented by the following general formula (I)

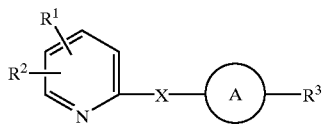

(I)

wherein
$R^1$ and $R^2$ are the same or different and each is hydrogen, lower alkyl, lower alkoxy, cyano, lower alkoxycarbonyl, carboxy, lower haloalkyl, hydroxy(lower)alkyl, hydroxy, nitro, amino, mono or di(lower)alkylamino, protected hydroxy or lower alkyl substituted by protected hydroxy;
X is a single bond or a group of the formula selected from the group consisting of

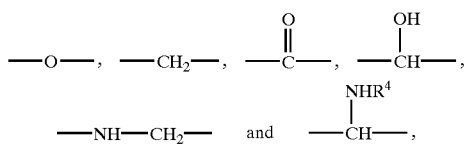

wherein $R^4$ is hydrogen or acyl;
ring A is heterocycle or arylene wherein said heterocycle and arylene may be substituted by suitable substituent(s) selected from the group consisting of lower alkyl, lower alkoxy, halogen and guanidino which may be substituted by suitable substituent(s); and
$R^3$ is a group of the formula selected from the group consisting of

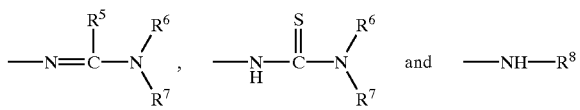

wherein $R^5$ is hydrogen, lower alkyl, lower alkylthio, amino which may be substituted by suitable substituent (s) or aromatic heterocyclic group, or when

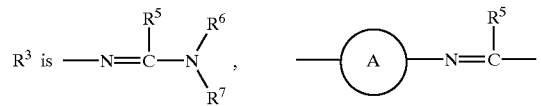

may form a bicyclic group selected from the group consisting of

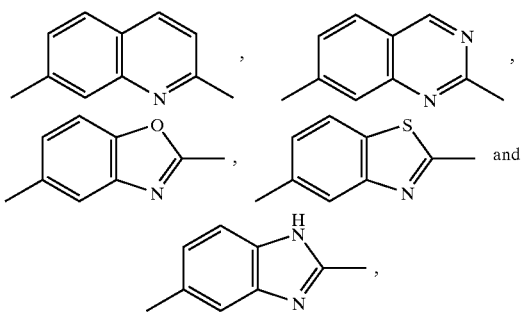

wherein said bicyclic group may be substituted by suitable substituent(s) selected from the group consisting of lower alkyl and aryl,
$R^6$ and $R^7$ are the same or different and each is hydrogen, lower alkyl, cyano, amino, hydroxy, acyl or amidino which may be substituted by suitable substituent(s), and $R^8$ is thiazolinyl or pyridyl.

Suitable pharmaceutically acceptable salts of the object compound (I) are conventional non-toxic salts and include, for example, a salt with a base or an acid addition salt such as a salt with an inorganic base, for example, an alkaline metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, methanesulfonate, benzenesulfonate, toluenesulfonate, etc.); and a salt with a basic or acidic amino acid (e.g., arginine salt, aspartic acid salt, gultamic acid salt, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and "lower alkyl moiety" in the terms "hydroxy(lower)alkyl", "mono or di(lower) alkylamino" and "lower alkylthio" include straight or branched one having 1 to 6 carbon atom(s), such as methyl, ethyl, propyl, isopropyl, butyl, isobutyl, sec-butyl, tert-butyl, pentyl, neopentyl, tert-pentyl and hexyl, in which more preferred one is $C_1$–$C_4$ alkyl.

Suitable "lower alkoxy" and "lower alkoxy moiety" in the term "lower alkoxycarbonyl" include, straight or branched one having 1 to 6 carbon atom(s), such as methoxy, ethoxy, propoxy, isopropoxy, butoxy, isobutoxy, tert-butoxy, pentyloxy, neopentyloxy, tert-pentyloxy and hexyloxy, in which more preferred one is $C_1$–$C_4$ alkoxy.

Suitable "lower alkoxycarbonyl" includes, for example, methoxycarbonyl, ethoxycarbonyl, propoxycarbonyl, isopropoxycarbonyl, butoxycarbonyl, isobutoxycarbonyl, tert-butoxycarbonyl, pentyloxycarbonyl and hexyloxycarbonyl.

Suitable "lower haloalkyl" includes, straight or branched one having 1 to 6 carbon atom(s), such as trifluoromethyl, trichloromethyl and tribromomethyl, in which more preferred one is trifluoromethyl.

Suitable "hydroxy(lower)alkyl" includes, for example, hydroxymethyl, 2-hydroxyethyl, 1-hydroxyethyl, 3-hydroxypropyl, 2-hydroxypropyl, 1-hydroxypropyl, 2-hydroxy-1-methylethyl, 4-hydroxybutyl, 3-hydroxybutyl, 2-hydroxybutyl, 1-hydroxybutyl, 1,1-dimethyl-2-hydroxyethyl, 5-hydroxypentyl and 6-hydroxyhexyl.

Suitable "mono or di(lower)alkylamino" includes, for example, methylamino, ethylamino, propylamino, isopropylamino, butylamino, tert-butylamino, N,N-dimethylamino, N,N-diethylamino, N,N-dipropylamino, N,N-dibutylamino, N-ethyl-N-methylamino, N-methyl-N-propylamino and N-butyl-N-methylamino.

Suitable "acyl" includes, for example, carbamoyl, aliphatic acyl group and acyl group containing an aromatic ring, which is referred to as aromatic acyl, or a heterocyclic ring, which is referred to as heterocyclic acyl.

Suitable examples of said acyl are illustrated as follows: carbamoyl; aliphatic acyl such as lower alkanoyl which may be substituted by one to three halogen atoms (e.g., formyl, acetyl, propanoyl, butanoyl, 2-methylpropanoyl, pentanoyl, 2,2-dimethylpropanoyl, hexanoyl, trichloroacetyl, trifluoroacetyl, etc.), lower alkoxycarbonyl (e.g., methoxycarbonyl, ethoxycarbonyl, tert-butoxycarbonyl, tert-pentyloxycarbonyl, etc.), lower alkylsulfonyl (e.g., methylsulfonyl, ethylsulfonyl, etc.), lower alkoxysulfonyl (e.g., methoxysulfonyl, ethoxysulfonyl, etc.), cyclo(lower)alkylcarbonyl (e.g., cyclopentylcarbonyl, cyclohexylcarbonyl, etc.), and the like; aromatic acyl such as aroyl (e.g., benzoyl, toluoyl, naphthoyl, etc.), aryl(lower)alkanoyl [e.g., phenyl(lower)alkanoyl (e.g., phenylacetyl, phenylpropanoyl, phenylbutanoyl, etc.), naphthyl(lower)alkanoyl (e.g., naphthylacetyl, naphthylpropanoyl, naphthylbutanoyl, etc.), etc.], aryl(lower)alkoxycarbonyl [e.g., phenyl(lower)alkoxycarbonyl (e.g., benzyloxycarbonyl, etc.), etc.], aryloxycarbonyl (e.g., phenoxycarbonyl, naphthyloxycarbonyl, etc.), aryloxy(lower)alkanoyl (e.g., phenoxyacetyl, phenoxypropionyl, etc.), arylsulfonyl (e.g., phenylsulfonyl, p-tolylsufonyl, etc.), and the like; heterocyclic acyl such as indolylcarbonyl (e.g., indolyl-2-ylcarbonyl, etc.), benzofuranylcarbonyl (e.g., benzofuran-2-ylcarbonyl), quinoxalinylcarbonyl, quinolylcarbonyl, pyrrolylcarbonyl, benzimidazolylcarbonyl, benzothienylcarbonyl, benzothiazolylcarbonyl, imidazolylcarbonyl, pyridylcarbonyl, morpholinylcarbonyl (e.g., morpholinocarbonyl) and the like. More preferred examples of "acyl" include lower alkanoyl having 1 to 6 carbon atoms (e.g., formyl, acetyl, propanoyl, butanoyl, 2-methylpropanoyl, pentanoyl, 2,2-dimethylpropanoyl, hexanoyl, etc.) and lower alkoxycarbonyl (e.g., methoxycarbonyl, ethoxycarbonyl, tert-butoxycarbonyl, tert-pentyloxycarbonyl, etc.).

Suitable examples of "hydroxy protective group" include aforesaid acyl (e.g., acetyl, trichloroacetyl, etc.), mono(or di or tri)phenyl(lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, tert-butyldimethylsilyl, etc.), etc.], tetrahydropyranyl and the like.

Suitable examples of "protected hydroxy" include tri(lower)-alkylsilyloxy (e.g., trimethylsilyloxy, tert-butyldimethylsilyloxy, etc.), acyloxy (e.g., acetoxy, etc.), mono(or di or tri)phenyl(lower)alkyloxy (e.g., benzyloxy, etc.) and tetrahydropyranyloxy.

Suitable examples of "lower alkyl substituted by protected hydroxy" include tri(lower)alkylsilyloxy(lower)alkyl (e.g., trimethylsilyloxymethyl, tert-butyldimethylsilyloxymethyl, 2-(trimethylsilyloxy)ethyl, 2-(tert-butyldimethylsilyloxy)ethyl, etc.), acyloxy(lower)alkyl (e.g., acetoxymethyl, etc.), mono(or di or tri)phenyl(lower)alkyloxy(lower)alkyl (e.g., benzyloxymethyl, etc.) and tetrahydropyranyloxy(lower)alkyl (e.g., tetrahydropyranyloxymethyl, etc.).

Suitable "heterocycle" for ring A includes heterocycle containing nitrogen atom(s) and heterocycle containing nitrogen atom(s) and sulfur atom(s). Suitable "heterocycle containing nitrogen atom(s)" includes saturated or unsaturated 5 or 6-membered heteromonocycle containing 1 to 4 nitrogen atom(s), for example, pyrrole, pyrroline, imidazole, imidazoline, pyrazole, pyrazoline, pyridine, dihydropyridine, pyrimidine, pyrazine, pyridazine, triazole, tetrazole, triazine, pyrrolidine, imidazolidine, pyrazolidine, piperidine and piperazine, in which more preferred ones are pyrimidine, imidazole and pyrrolidine. Suitable "heterocycle containing nitrogen atom(s) and sulfur atom(s)" includes saturated or unsaturated 5 or 6-membered heteromonocycle containing I to 3 nitrogen atom(s) and 1 or 2 sulfur atom(s), for example, thiazole, isothiazole, thiadiazole, thiazine, dihydrothiazine and thiazolidine, in which more preferred one is thiazole.

Suitable "arylene" for ring A includes phenylene (e.g., 1,2-phenylene, 1,3-phenylene, 1,4-phenylene) and naphthylene (e.g., 1,2-naphthylene, 1,3-naphthylene, 1,4-naphthylene, 1,5-naphthylene, 1,6-naphthylene, 1,7-naphthylene, 1,8-naphthylene, 2,3-naphthylene, 2,6-naphthylene, 2,7-naphthylene), in which more preferred one is phenylene.

Suitable examples of ring A include those represented by the following formulas:

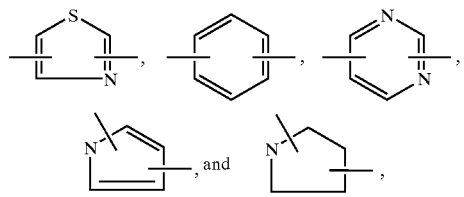

Suitable "halogen" includes, for example, fluorine, bromine, chlorine and iodine.

"Guanidino which may be substituted by suitable substituent(s)" includes a group of the formula

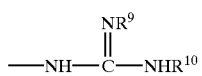

wherein $R^9$ and $R^1$ are the same or different and each is hydrogen, lower alkyl, cyano or amino protective group. Suitable examples of said amino protective group include lower alkoxycarbonyl (e.g., methoxycarbonyl, ethoxycarbonyl, tert-butoxycarbonyl, tert-pentyloxycarbonyl, etc.).

Suitable "lower alkylthio" includes, for example, methylthio, ethylthio, propylthio, isopropylthio, butylthio, isobutylthio, sec-butylthio, tert-butylthio, pentylthio, neopentylthio, tert-pentylthio and hexylthio, in which more preferred one is $C_1$–$C_4$ alkylthio.

Suitable substituent(s) in the term "amino which may be substituted by suitable substituent(s)" includes lower alkyl, acyl (e.g., lower alkoxycarbonyl) and cyano.

Suitable examples of "amino which may be substituted by suitable substituent(s)" include amino, mono or di(lower) alkylamino (e.g., methylamino, ethylamino, propylamino, isopropylamino, butylamino, tert-butylamino, N,N-dimethylamino, N,N-diethylamino, N,N-dipropylamino, N,N-dibutylamino, N-ethyl-N-methylamino, N-methyl-N-propylamino, N-butyl-N-methylamino, etc.), acylamino [e.g., lower alkoxycarbonylamino (e.g., methoxycarbonylamino, ethoxycarbonylamino, tert-butoxycarbonylamino, tert-pentyloxycarbonylamino, etc.)] and cyanoamino.

Suitable "aromatic heterocyclic group" includes 5 or 6-membered aromatic heteromonocyclic group containing at least one hetero atom selected from sulfur atom, oxygen atom and nitrogen atom, for example, thienyl, furyl, pyrrolyl, thiazolyl, isothiazolyl, oxazolyl, isoxazolyl, imidazolyl, pyrazolyl, triazolyl, tetrazolyl, pyridyl, pyridazinyl, pyrimidinyl and pyrazinyl. Preferred one is 5-membered aromatic heteromonocyclic group containing sulfur atom or oxygen atom, for example, thienyl (e.g., 2-thienyl, 3-thienyl) and furyl (e.g., 2-furyl, 3-furyl), in which more preferred one is thienyl (e.g., 2-thienyl, 3-thienyl).

Suitable "aryl" includes, for example, phenyl and naphthyl, in which more preferred one is phenyl.

"Amidino which may be substituted by suitable substituent(s)" includes a group of the formula

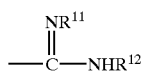

wherein $R^{11}$ and $R^{12}$ are the same or different and each is hydrogen, lower alkyl, cyano or amino protective group. Suitable examples of said amino protective group include lower alkoxycarbonyl (e.g., methoxycarbonyl, ethoxycarbonyl, tert-butoxycarbonyl, tert-pentyloxycarbonyl, etc.).

Suitable "thiazolinyl" includes, for example, 2-thiazolinyl.

Suitable "pyridyl" includes, for example, 2-pyridyl, 3-pyridyl and 4-pyridyl.

Suitable "amino protective group" includes, for example, acyl (e.g., lower alkoxycarbonyl, aryl(lower)alkoxycarbonyl, etc.) and conventional protective group such as mono(or di or tri)aryl(lower)alkyl, for example, mono(or di or tri)phenyl(lower)alkyl (e.g., benzyl, benzhydryl, trityl, etc.), in which more preferred one is lower alkoxycarbonyl (e.g., methoxycarbonyl, ethoxycarbonyl, tert-butoxycarbonyl, tert-pentyloxycarbonyl, etc.).

According to the present invention, the object compound (I) can be prepared by the following processes.

Process (1)

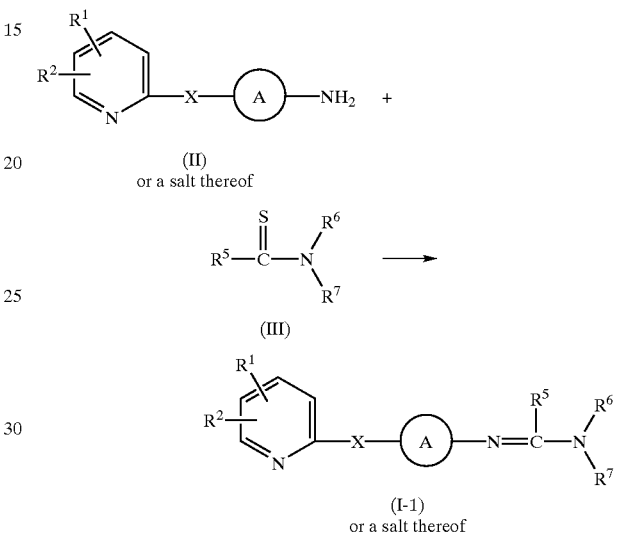

Process (2)

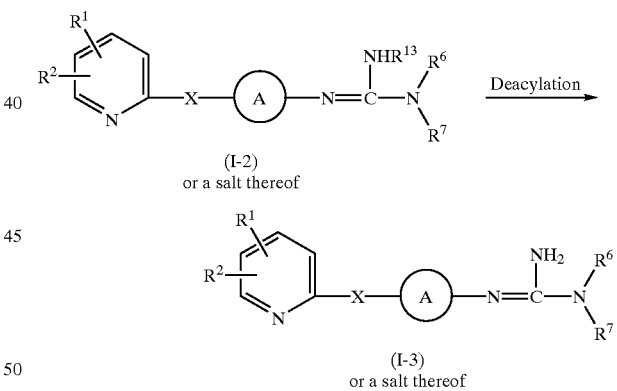

Process (3)

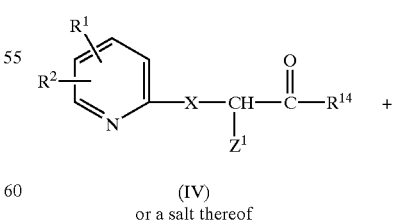

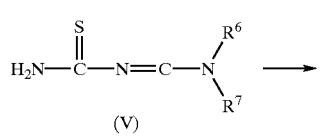

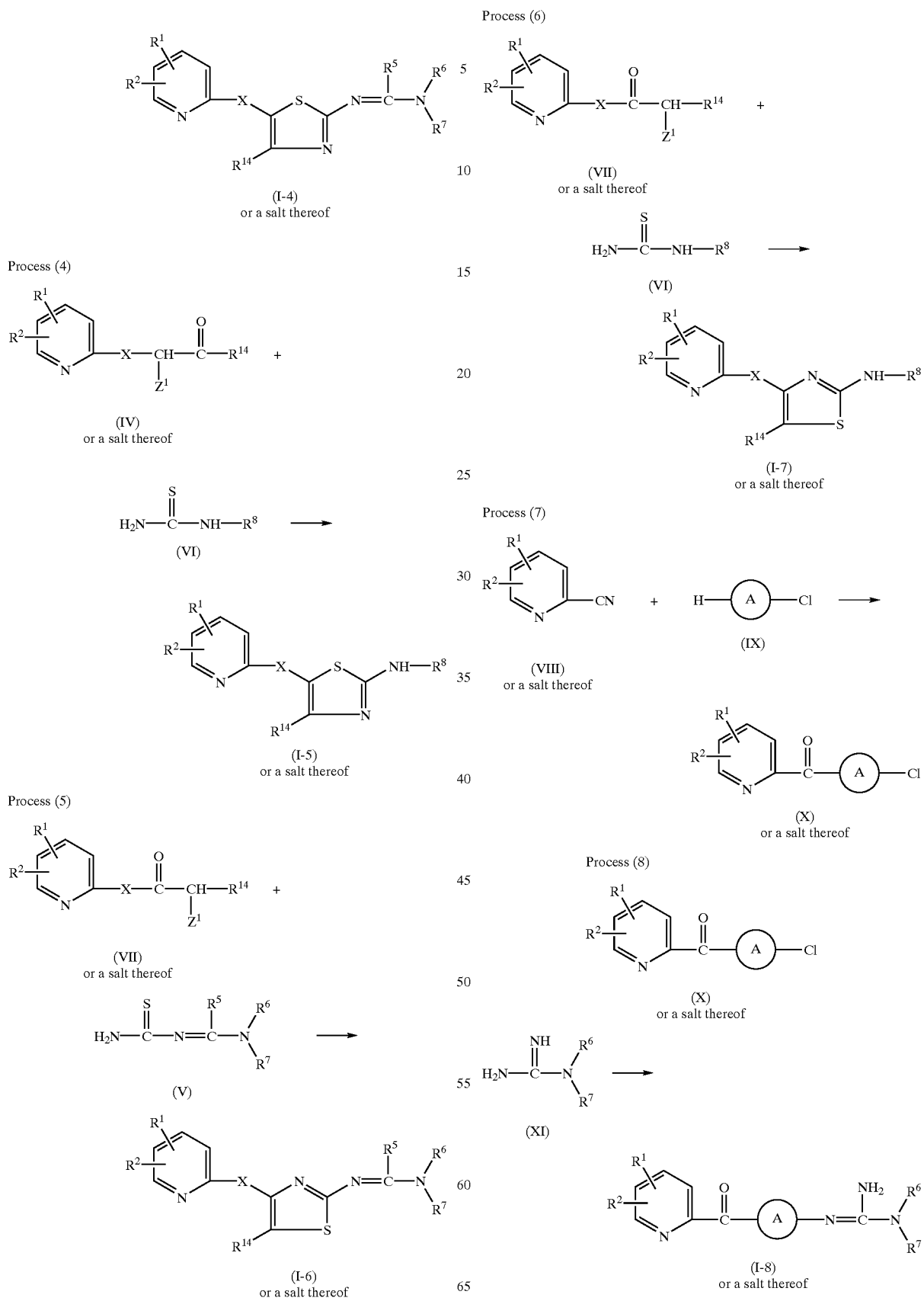

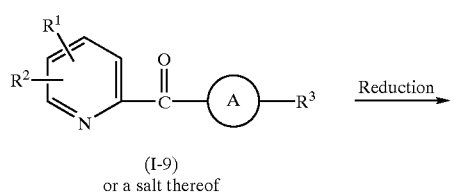

Process (17)
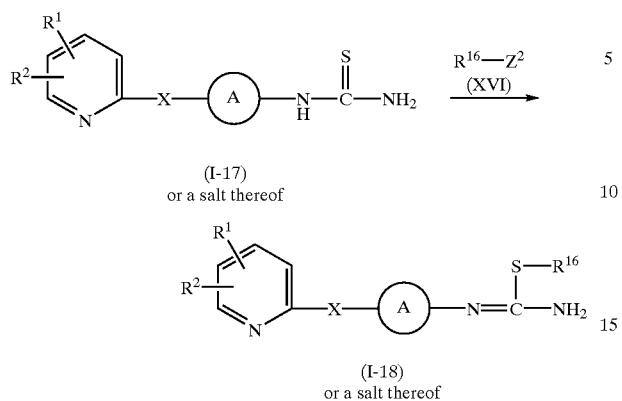
Process (18)
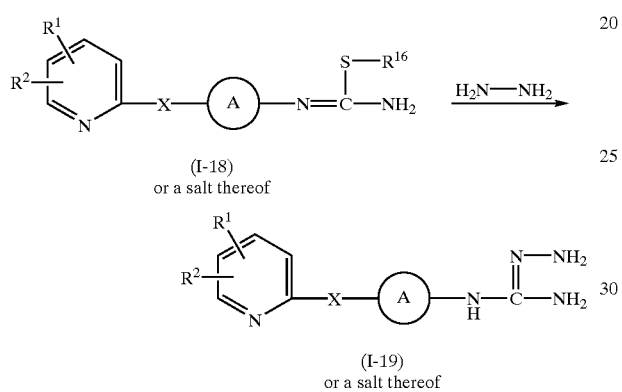
Process (19)
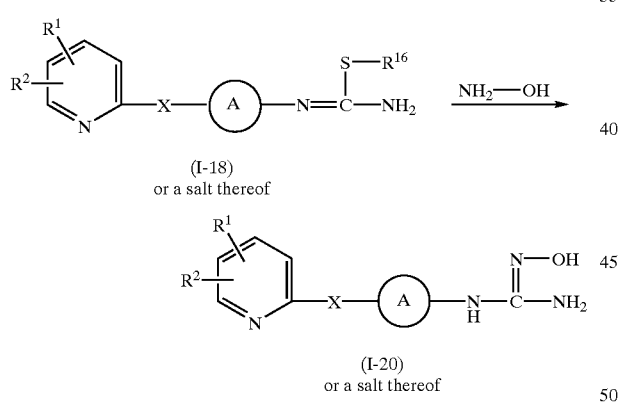
Process (20)
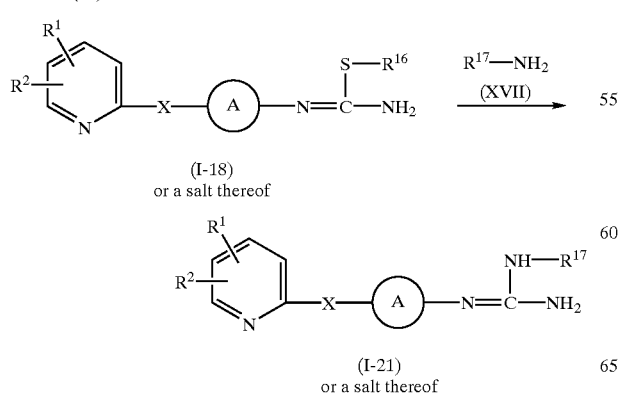
Process (21)
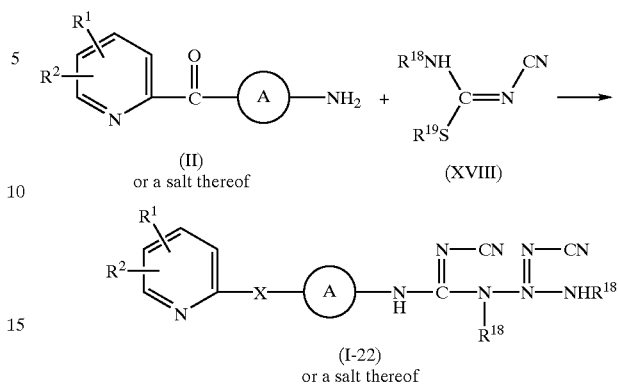
Process (22)
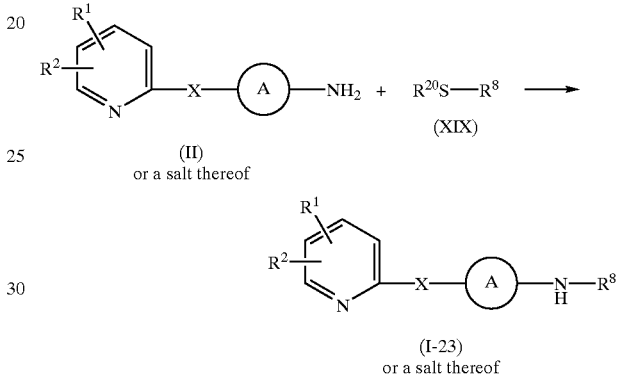
Process (23)
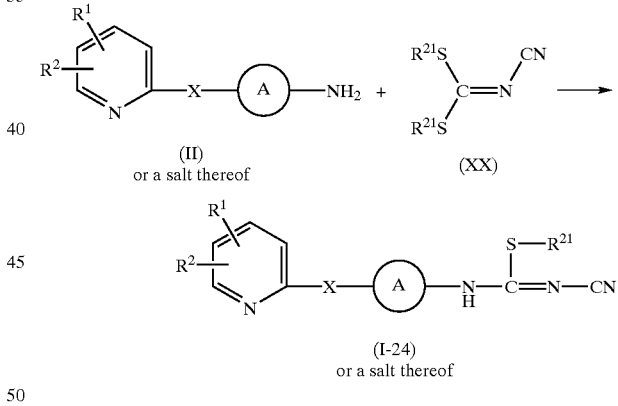
Process (24)
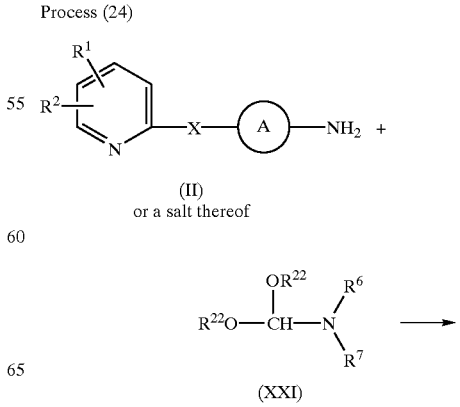

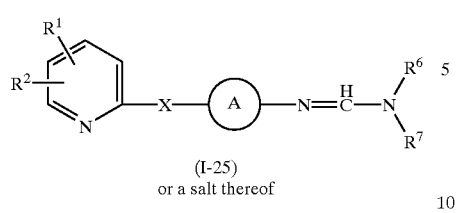

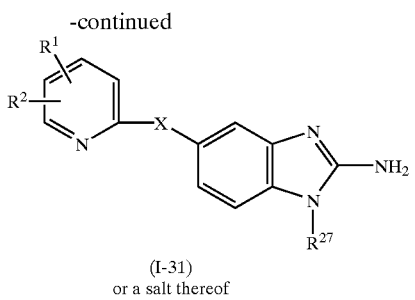

(I-31)
or a salt thereof

Process (31)

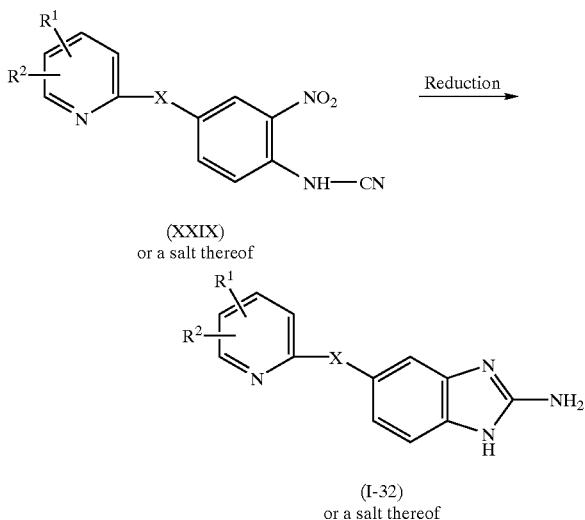

wherein
R¹, R², R³, R⁵, R⁶, R⁷, R⁸, X and ring A are each as defined above,
$R^{13}$ is acyl,
$R^{14}$ is hydrogen or lower alkyl,
$Z^1$, $Z^2$ and $Z^3$ are each halogen,
$R^{16}$, $R^{17}$, $R^{18}$, $R^{19}$, $R^{20}$, $R^{21}$, $R^{22}$ and $R^2$ are each lower alkyl,
$R^4a$ is acyl,
$R^{15}$ and $R^{26}$ are each amino protective group,
$R^{23}$ is lower alkyl or aromatic heterocyclic group, $R^{25}$ is hydrogen or lower alkyl
$R^{27}$ is lower alkyl or aryl, and
$X^1$ is sulfur atom or oxygen atom.

The starting compounds or a salt thereof can be prepared by the procedures described in the Preparations mentioned below or by a process known in the art for preparing their structually analogous compounds.

The processes for preparing the object compound (I) of the present invention are explained in detail in the following.

Process (1)

The compound (I-1) or a salt thereof can be prepared by reacting the compound (II) or a salt thereof with the compound (III) in the presence of 1-methyl-2-chloropyridinium iodide and an organic base such as tri(lower)alkylamine (e.g., diisopropylethylamine).

The reaction is usually carried out in a conventional solvent such as alcohol (e.g., methanol, ethanol, isopropyl alcohol, etc.), tetrahydrofuran, dioxane, methylene chloride, ethylene dichloride, chloroform, N,N-dimethylformamide, N,N-dimethylacetamide or any other organic solvents which do not adversely affect the reaction, or a mixture thereof.

The reaction temperature is not critical and the reaction is usually carried out under cooling to heating.

Process (2)

The compound (I-3) or a salt thereof can be prepared by subjecting the compound (I-2) or a salt thereof to deacylation.

Suitable method of this deacylation includes conventional one such as hydrolysis, reduction and the like. The hydrolysis is preferably carried out in the presence of a base or an acid.

Suitable base includes an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-one, or the like.

Suitable acid includes an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The reaction may be carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or a mixture thereof.

The reaction temperature is not critical and the reaction is usually carried out under cooling to warming.

Process (3)

The compound (I-4) or a salt thereof can be prepared by reacting the compound (IV) or a salt thereof with the compound (V).

The reaction is usually carried out in a conventional solvent such as ethyl acetate, methylene chloride, chloroform, carbon tetrachloride, tetrahydrofuran, N,N-dimethylformamide, N,N-dimethylacetamide, dioxane, water, alcohol (e.g., methanol, ethanol, isopropyl alcohol, etc.) or any other organic solvents which do not adversely affect the reaction, or a mixture thereof.

The reaction temperature is not critical and the reaction is usually carried out under cooling to heating.

Process (4)

The compound (1-10) or a salt thereof can be prepared by subjecting the compound (I-9) or a salt thereof to reduction.

This reaction can be carried out in a similar manner to the reaction in the aforementioned Process (3), and therefore the reagents to be used and the reaction conditions (e.g., solvent, reaction temperature, etc.) can be referred to those of the Process (3).

Process (5)

The compound (I-11) or a salt thereof can be prepared by reacting the compound (I-10) or a salt thereof with triethylsilane (XII).

The reaction is usually carried out in a conventional solvent such as ethyl acetate, methylene chloride, chloroform, carbon tetrachloride, tetrahydrofuran, N,N-dimethylformamide, N,N-dimethylacetamide, dioxane, water, alcohol (e.g., methanol, ethanol, isopropyl alcohol, etc.) or any other organic solvents which do not adversely affect the reaction, or a mixture thereof.

The reaction temperature is not critical and the reaction is usually carried out under cooling to heating.

Process (6)

The compound (I-12) or a salt thereof can be prepared by reacting the compound (I-10) or a salt thereof with acetonitrile and sulfuric acid.

This reaction can be carried out in a similar manner to the reaction in the aforementioned Process (5), and therefore the reagents to be used and the reaction conditions (e.g., solvent, reaction temperature, etc.) can be referred to those of the Process (5).

Process (7)

The compound (X) or a salt thereof can be prepared by reacting the compound (VIII) or a salt thereof with the compound (IX).

This reaction can be carried out in the same manner as in Preparation 15 or in a similar manner thereto.

Process (8)

The compound (I-8) or a salt thereof can be prepared by reacting the compound (X) or a salt thereof with the compound (XI).

This reaction can be carried out in the same manner as in Example 23 or in a similar manner thereto.

Process (9)

The compound (I-10) or a salt thereof can be prepared by subjecting the compound (1-9) or a salt thereof to reduction.

This reaction can be carried out in the same manner as in Example 24 or in a similar manner thereto.

Process (10)

The compound (I-11) or a salt thereof can be prepared by reacting the compound (1-10) or a salt thereof with triethylsilane (XII).

This reaction can be carried out in the same manner as in Example 25 or in a similar manner thereto.

Process (11)

The compound (I-12) or a salt thereof can be prepared by reacting the compound (1-10) or a salt thereof with acetonitrile and sulfuric acid.

This reaction can be carried out in the same manner as in Example 26 or in a similar manner thereto.

Process (12)

The compound (I-13) or a salt thereof can be prepared by subjecting the compound (I-12) or a salt thereof to deacetylation.

This reaction can be carried out in a similar manner to the reaction in the aforementioned Process (2), and therefore the reagents to be used and the reaction conditions (e.g., solvent, reaction temperature, etc.) can be referred to those of the Process (2).

Process (13)

The compound (I-14) or a salt thereof can be prepared by subjecting the compound (I-13) or a salt thereof to acylation.

Suitable examples of an acylating agent to be used in the acylation include an acid halide (e.g. acid chloride, etc.), an acid anhydride, an activated amide and an acivated ester.

The reaction is usually carried out in a conventional solvent such as water, alcohol (e.g., methanol, ethanol, isopropyl alcohol, etc.), acetone, dioxane, acetonitrile, chloroform, methylene chloride, ethylene dichloride, tetrahydrofuran, ethyl acetate, N,N-dimethylformamide, N,N-dimethylacetamide, pyridine, acetic acid or any other organic solvents which do not adversely affect the reaction, or a mixture thereof.

The reaction temperature is not critical and the reaction is usually carried out under cooling to heating.

The reaction may be carried out in the presence of an inorganic or organic base such as an alkali metal hydrogencarbonate, tri(lower)alkylamine, pyridine, N-(lower)alkylmorpholine and N,N-di(lower)alkylbenzylamine.

Process (14)

The compound (I-15) or a salt thereof can be prepared by reacting the compound (XIII) or a salt thereof with the compound (XIV) in the presence of a reducing agent.

This reaction can be carried out in the same manner as in Example 28 or in a similar manner thereto.

Process (15)

The compound (I-16) or a salt thereof can be prepared by reacting the compound (II) or a salt thereof with the compound (XV).

This reaction can be carried out in the same manner as in Preparation 14 or in a similar manner thereto.

Process (16)

The compound (I-17) or a salt thereof can be prepared by subjecting the compound (I-16) or a salt thereof to elimination of the amino protective group.

This reaction can be carried out in the same manner as in Example 10 or in a similar manner thereto.

Process (17)

The compound (I-18) or a salt thereof can be prepared by reacting the compound (I-17) or a salt thereof with the compound (XVI).

This reaction can be carried out in the same manner as in Example 11 or in a similar manner thereto.

Process (18)

The compound (I-19) or a salt thereof can be prepared by reacting the compound (I-18) or a salt thereof with hydrazine.

This reaction can be carried out in the same manner as in Example 12 or in a similar manner thereto.

Process (19)

The compound (I-20) or a salt thereof can be prepared by reacting the compound (I-18) or a salt thereof with hydroxylamine.

This reaction can be carried out in the same manner as in Example 13 or in a similar manner thereto.

Process (20)

The compound (I-21) or a salt thereof can be prepared by reacting the compound (I-18) or a salt thereof with the compound (XVII).

This reaction can be carried out in the same manner as in Example 14 or in a similar manner thereto.

Process (21)

The compound (I-22) or a salt thereof can be prepared by reacting the compound (II) or a salt thereof with the compound (XVIII).

This reaction can be carried out in the same manner as in Example 16 or in a similar manner thereto.

Process (22)

The compound (I-23) or a salt thereof can be prepared by reacting the compound (II) or a salt thereof with the compound (XIX).

This reaction can be carried out in the same manner as in Example 17 or in a similar manner thereto.

Process (23)

The compound (I-24) or a salt thereof can be prepared by reacting the compound (II) or a salt thereof with the compound (XX).

This reaction can be carried out in the same manner as in Example 19 or in a similar manner thereto.

Process (24)

The compound (I-25) or a salt thereof can be prepared by reacting the compound (II) or a salt thereof with the compound (XXI).

This reaction can be carried out in the same manner as in Example 20 or in a similar manner thereto.

Process (25)

The compound (I-26) or a salt thereof can be prepared by reacting the compound (II) or a salt thereof with the compound (XXII).

This reaction can be carried out in the same manner as in Example 21 or Example 69 or in a similar manner thereto.

Process (26)

The compound (I-27) or a salt thereof can be prepared by subjecting the compound (XXIII) or a salt thereof to ring-closing reaction in the presence of a reducing agent.

This reaction can be carried out in the same manner as in Example 96 or Example 97 or in a similar manner thereto.

Process (27)

The compound (I-28) or a salt thereof can be prepared by reacting the compound (XXIV) or a salt thereof with the compound (XXV).

This reaction can be carried out in the same manner as in Example 98 or in a similar manner thereto.

Process (28)

The compound (I-29) or a salt thereof can be prepared by subjecting the compound (XXVI) or a salt thereof to elimination of the protective groups.

This reaction can be carried out in the same manner as in Example 100 or in a similar manner thereto.

Process (29)

The compound (I-30) or a salt thereof can be prepared by reacting the compound (XXVII) or a salt thereof with cyanogen bromide.

This reaction can be carried out in the same manner as in Example 102 or in a similar manner thereto.

Process (30)

The compound (I-31) or a salt thereof can be prepared by reacting the compound (XXVIII) or a salt thereof with cyanogen bromide.

This reaction can be carried out in the same manner as in Example 103 or in a similar manner thereto.

Process (31)

The compound (I-32) or a salt thereof can be prepared by subjecting the compound (XXIX) or a salt thereof to reduction.

This reaction can be carried out in the same manner as in Example 106 or in a similar manner thereto.

Process (32)

The compound (I-33) or a salt thereof can be prepared by reacting the compound (XXX) or a salt thereof with sodium hydride.

This reaction can be carried out in the same manner as in Example 107 or in a similar manner thereto.

The compounds obtained by the above processes can be isolated and purified by a conventional method such as pulverization, recrystallization, column chromatography, reprecipitation, or the like.

It is to be noted that the compound (I) and the other compounds may include one or more stereoisomer(s) such as optical isomer(s) and geometrical isomer(s) due to asymmetric carbon atom(s) and double bond(s), and all of such isomers and mixtures thereof are included within the scope of this invention.

Furthermore, with regard to the compound (I), it is to be noted that the following formula (A) is well known to be a tautomeric isomer of the following formula (B), and accordingly, it is to be understood that both of the isomers are substantially the same.

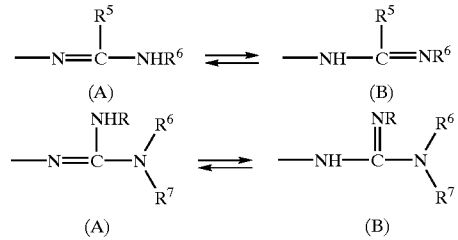

wherein $R^5$, $R^6$ and $R^7$ are each as defined above, and R is hydrogen or a substituent such as lower alkyl, acyl or cyano.

Accordingly, the both of the tautomeric forms are clearly included within the scope of the present invention. In the present specification, the object and starting compounds including the group of such tautomeric isomers are represented by using one of the expressions.

The object compounds (I) and pharmaceutically acceptable salts thereof include solvates [e.g., enclosure compounds (e.g., hydrate, etc.)].

The object compounds (I) and pharmaceutically acceptable salts thereof possess a strong inhibitory activity on the production of nitric oxide (NO).

Accordingly, the object compounds (I) and pharmaceutically acceptable salts thereof are expected to possess a nitric oxide synthase (NOS)-inhibitory activity or a NOS-production inhibitory activity.

Accordingly, they are useful for prevention and/or treatment of NOS-mediated diseases such as adult respiratory distress syndrome, myocarditis, synovitis, septic shock, insulin-dependent diabetes mellitus, ulcerative colitis, cerebral infarction, rheumatoid arthritis, osteoarthritis, osteoporosis, systemic lupus erythematosus, rejection by organ transplantation, asthma, pain, ulcer, and the like in human being or animals.

In order to illustrate the usefulness of the object compound (I), the pharmacological test data of the representative compound of the compound (I) are shown in the following.

Test: Binding Assay Using Nitric Oxide Synthase (NOS)

(1) Test method

A crude preparation of NOS was obtained from brains of male SD rats. The whole brain (including cerebellum) was homogenized with 5 volume (W/V) of 50 mM Tris buffer (pH 7.0 at 4° C.) and centrifuged at 48,000×g for 20 minutes. The pellet was discarded and the supernatant was passed through ¼ volume (V/V) of Dowex AG50WX-8 resin (Na$^+$ form), in order to remove endogenous arginine. The supernatant was collected, the pH was adjusted to 7.0 at 22° C., and this cytosolic preparation was frozen and stored at −80° C. until required. In the binding assay, each drug was incubated with the brain cytosol (200 μg protein/tube) in 0.15 ml (final volume) of 50 mM Tris buffer containing 10 μM $CaCl_2$ and 10 nM [$^3$H]Na (Amersham, UK). Incubation was performed at 27° C. for 90 minutes and terminated by vacuum filtration through 0.3% polyethyleneimine pretreated GF/B glass fibre filters which were subsequently washed with distilled water (4° C., 4 ml×4). Nonspecific binding was defined by use of 100 µl Na. Data are expressed as inhibition % of specific binding.

(2) Test Compounds (a) 2-Guanidino-4-methyl-5-(4-methoxypyridin-2-yl) thiazole
(b) (5-(4-Methoxypyridin-2-yl)-2-methylphenyl)guanidine dihydrochloride
(c) N-(3-(4-Methoxypyridin-2-yl)phenyl)-S-ethylisothiourea dihydrochloride
(d) 2-Amino-7-(4-methoxypyridin-2-yl)quinoline dihydrochloride
(e) 2-Amino-7-(4-methylpyridin-2-yl)quinoline dihydrochloride
(f) 7-(4-Methoxypyridin-2-yl)-2-methylaminoquinoline dihydrochloride Test Result

| Test compound ($10^{-4}$M) | Inhibition (%) |
|---|---|
| (a) | 99.0 |
| (b) | 98.9 |
| (c) | 100 |
| (d) | 99.3 |
| (e) | 98.0 |
| (f) | 99.4 |

For therapeutic administration, the object compound (I) of the present invention and pharmaceutically acceptable salts thereof are used in the form of a conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drop, etc. If needed, there may be included in the above preparation auxiliary substance such as stabilizing agent, wetting or emulsifying agent, buffer or any other commonly used additives.

The optimal dosage of effective ingredient which may be usually selected from the range of 0.001 mg/kg to 50 mg/kg, preferably 0.01 mg/kg to 10 mg/kg, is administered 1 to 4 times a day. However, the above dosage may be increased or decreased according to age, body weight and conditions of the patient or administering method.

The preferred embodiments of the pyridine compounds of the present invention represented by the general formula (I) are as follows.

1) The compound of the formula (I) wherein
$R^1$ and $R^2$ are the same or different and each is hydrogen, lower alkyl, lower alkoxy, cyano, lower alkoxycarbonyl, carboxy, lower haloalkyl, hydroxy(lower)alkyl, hydroxy, nitro, amino or mono or di(lower)alkylamino.

2) The compound of the formula (I) wherein
ring A is a ring selected from the group consisting of

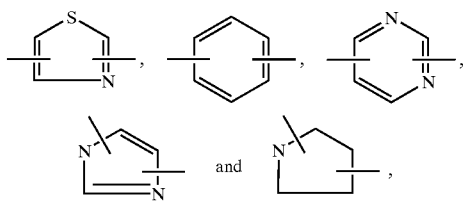

wherein said ring A may be substituted by suitable substituent(s) selected from the group consisting of lower alkyl, lower alkoxy, halogen and guanidino.

3) The compound of the formula (I) wherein $R^3$ is

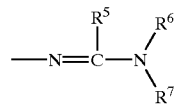

wherein $R^5$, $R^6$ and $R^7$ are as defined above.

4) The compound of the formula (I) wherein $R^3$ is

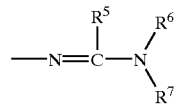

wherein $R^5$ is hydrogen, lower alkyl, lower alkylthio, amino, mono or di(lower)alkylamino, acylamino, cyanoamino or 5-membered aromatic heteromonocyclic group containing sulfur atom or oxygen atom, or

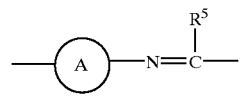

may form a bicyclic group selected from the group consisting of

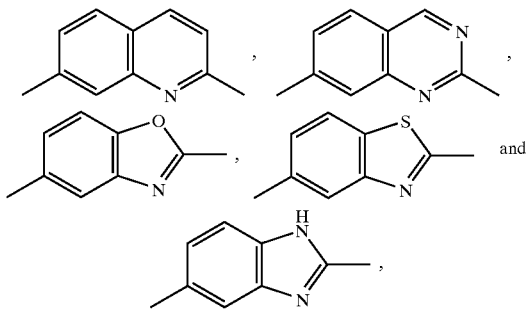

wherein said bicyclic group may be substituted by suitable substituent(s) selected from the group consisting of lower alkyl and aryl, and
$R^6$ and $R^7$ are the same or different and each is hydrogen, lower alkyl, cyano, amino, hydroxy or amidino which may be substituted by suitable substituent(s) selected from the group consisting of lower alkyl and cyano.

The following Preparations and Examples are given for the purpose of illustrating the present invention in detail.

Preparation 1

To a stirred solution of 2,3-lutidine (3.21 g) in tetrahydrofuran (20 ml) was added a solution of n-butyllithium in n-hexane (1.56M, 23.1 ml) dropwise at −50° C. under a nitrogen atmosphere, and the mixture was warmed to 0° C. The mixture was cooled to −50° C., and N,N-dimethylacetamide (3.63 ml) was added dropwise. Then the mixture was warmed to room temperature, poured into a saturated aqueous ammonium chloride solution and extracted with ethyl acetate (100 ml×3). The combined organic layer was washed with brine, dried over sodium sulfate and evaporated under reduced pressure. The residue was purified by column chromatography (silica gel 100 g, n-hexane:ethyl acetate=1:2) to give 1-(3-methylpyridin-2-yl)propan-2-one (3.70 g).

$^1$H-NMR (CDCl$_3$): δ2.22(3H,s), 2.27(3H,s), 3.96(2H,s), 7.12(1H,dd,J=7.6 Hz,4.8 Hz), 7.47(1H,d,J=7.6 Hz), 8.39 (1H,d,J=4.8 Hz)

EXAMPLE 1

To a stirred solution of 1-(3-methylpyridin-2-yl)propan-2-one (1.0 g) in dichloromethane (10 ml) was added a solution of hydrogen chloride in 1,4-dioxane (4N, 2.52 ml) dropwise at 5° C., and the mixture was stirred for 20 minutes. A solution of sulfuryl chloride (0.7 ml) in dichloromethane (15 ml) was added dropwise, and the mixture was stirred for 10 minutes. The mixture was evaporated under reduced pressure, and ethanol (10 ml) and 2-imino-4-thiobiuret (792 mg) were added. The mixture was stirred at 80° C. for 4 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was triturated with ethyl acetate (5 ml), filtered, washed with ethyl acetate and dried to give 2-guanidino-4-methyl-5-(3-methylpyridin-2-yl)thiazole (652 mg).

$^1$H-NMR (DMSO-d$_6$): δ2.02(3H,s), 2.25(3H,s), 6.88(4H, broad s), 7.24(1H,dd,J=7.8 Hz,4.7 Hz), 7.68(1H,d,J=7.8 Hz), 8.39(1H,d,J=4.7 Hz)

Preparation 2

To a stirred solution of 4-methoxy-2,6-dimethylpyridine (1.56 g) in tetrahydrofuran (15 ml) was added a solution of n-butyllithium in n-hexane (1.63M, 9.1 ml) dropwise at −50° C. under a nitrogen atmosphere, and the mixture was warmed to 0° C. The mixture was cooled to −50° C., and N,N-dimethylacetamide (1.59 ml) was added dropwise. Then the mixture was warmed to room temperature, poured into a saturated aqueous ammonium chloride solution and extracted with ethyl acetate (100 ml×2). The combined organic layer was washed with brine, dried over sodium sulfate and evaporated under reduced pressure. The residue was purified by column chromatography (silica gel 100 g, n-hexane:ethyl acetate=2:1) to give 1-(4-methoxy-6-methylpyridin-2-yl)propan-2-one (1.75 g).

$^1$H-NMR (CDCl$_3$): δ2.22(3H,s), 2.48(3H,s), 3.72(2H,s), 3.81(3H,s), 6.56(1H,d,J=2.2 Hz), 6.58(1H,d,J=2.2 Hz)

EXAMPLE 2

To a stirred solution of 1-(4-methoxy-6-methylpyridin-2-yl)propan-2-one (1.19 g) in dichloromethane (10 ml) was added a solution of hydrogen chloride in 1,4-dioxane (4N, 1.66 ml) dropwise at 5° C., and the mixture was stirred for 10 minutes. A solution of sulfuryl chloride (0.747 ml) in dichloromethane (5 ml) was added dropwise, and the mixture was stirred for 30 minutes. The mixture was evaporated under reduced pressure, and ethanol (15 ml) and 2-imino-4-thiobiuret (627 mg) were added. The mixture was stirred at 70° C. for 2.5 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was purified by column chromatography (silica gel 50 g, 5–8% methanol in dichloromethane) to give 2-guanidino-4-methyl-5-(4-methoxy-6-methylpyridin-2-yl)thiazole (340 mg).

$^1$H-NMR (DMSO-d$_6$): δ2.38(3H,s), 2.45(3H,s), 3.82(3H, s), 6.64(1H,d,J=2.0 Hz), 6.78(1H,d,J=2.0 Hz), 6.8–7.4(4H,s)

Preparation 3

To a stirred solution of 2-methyl-4-methoxypyridine (2.03 g) in tetrahydrofuran (20 ml) was added a solution of n-butyllithium in n-hexane (1.63M, 12.1 ml) dropwise at −50° C. under a nitrogen atmosphere, and the mixture was warmed to 0° C. The mixture was cooled to −50° C., and N,N-dimethylacetamide (1.99 ml) was added dropwise. Then the mixture was warmed to room temperature, poured into a saturated aqueous ammonium chloride solution and extracted with ethyl acetate (100 ml×2). The combined organic layer was washed with brine, dried over sodium sulfate and evaporated under reduced pressure. The residue was purified by column chromatography (silica gel 100 g, n-hexane:ethyl acetate=1:2) to give 1-(4-methoxypyridin-2-yl)propan-2-one (2.35 g).

$^1$H-NMR (CDCl$_3$): δ2.23(3H,s), 3.85(3H,s), 3.88(2H,s), 6.7–6.9(2H,m), 8.37(1H,d,J=5.2 Hz)

EXAMPLE 3

To a stirred solution of 1-(4-methoxypyridin-2-yl)propan-2-one (515 mg) in dichloromethane (5 ml) was added sulfuryl chloride (0.276 ml) at 5° C., and the mixture was stirred for 1 hour. The mixture was evaporated under reduced pressure, and ethanol (15 ml) and 2-imino-4-thiobiuret (567 mg) were added. The mixture was stirred at 60° C. for 4 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was purified by column chromatography (silica gel 30 g, 10% methanol in dichloromethane) to give 2-guanidino-4-methyl-5-(4-methoxypyridin-2-yl)thiazole (141 mg).

$^1$H-NMR (DMSO-d$_6$): δ2.46(3H,s), 3.85(3H,s), 6.76(1H, dd,J=5.7 Hz,2.4 Hz), 6.8–7.2(4H,broad s), 6.97(1H,d,J=2.4 Hz), 8.29(1H,d,J=5.7 Hz)

Preparation 4

To a stirred solution of 3-methoxy-2-methylpyridine (844 mg) in tetrahydrofuran (10 ml) was added a solution of n-butyllithium in n-hexane (1.59M, 5.6 ml) dropwise at −50° C. under a nitrogen atmosphere, and the mixture was warmed to 0° C. The mixture was cooled to −50° C., and N,N-dimethylacetamide (0.955 ml) was added dropwise. Then the mixture was warmed to room temperature, poured into a saturated aqueous ammonium chloride solution and extracted with ethyl acetate (100 ml). The organic layer was washed with brine, dried over sodium sulfate and evaporated under reduced pressure. The residue was purified by column chromatography (silica gel 50 g, 25% ethyl acetate in n-hexane) to give 1-(3-methoxypyridin-2-yl)propan-2-one (1.12 g).

$^1$H-NMR (CDCl$_3$): δ2.20(3H,s), 3.79(3H,s), 3.95(2H,s), 7.1–7.3(2H,m), 8.15(1H,dd,J=4.1 Hz,2.0 Hz)

EXAMPLE 4

To a stirred solution of 1-(3-methoxypyridin-2-yl)propan-2-one (496 mg) in dichloromethane (10 ml) was added a solution of hydrogen chloride in 1,4-dioxane (4N, 1.13 ml) dropwise at 5° C., and the mixture was stirred for 20 minutes. A solution of sulfuryl chloride (0.326 ml) in dichloromethane (10 ml) was added dropwise, and the mixture was stirred for 5 minutes. The mixture was evaporated under reduced pressure, and ethanol (10 ml), 2-imino-4-thiobiuret (354 mg) and triethylamine (0.419 ml) were added. The mixture was refluxed for 2 hours and cooled to ambient temperature. The solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was triturated with ethanol, filtered, washed with diisopropyl ether and dried to give 2-guanidino-4-methyl-5-(3-methoxypyridin-2-yl)thiazole (272 mg).

$^1$H-NMR (DMSO-d$_6$): δ2.26(3H,s), 3.83(3H,s), 6.7–7.1 (4H,broad s), 7.23(1H,dd,J=8.3 Hz,4.6 Hz), 7.45(1H,dd,J=8.3 Hz,1.3 Hz), 8.14(1H,dd,J=4.6 Hz,1.3 Hz)

Preparation 5

To a stirred solution of 2,5-lutidine (2.68 g) in tetrahydrofuran (16 ml) was added a solution of n-butyllithium in n-hexane (1.66M, 16.6 ml) dropwise at −50° C. under a nitrogen atmosphere, and the mixture was warmed to 0° C. The mixture was cooled to −50° C., and N,N-dimethylacetamide (2.56 ml) was added dropwise. Then the mixture was warmed to room temperature, poured into a saturated aqueous ammonium chloride solution and extracted with ethyl acetate (100 ml×3). The combined organic layer was washed with brine, dried over sodium sulfate and evaporated under reduced pressure. The residue was purified by column chromatography (silica gel 100 g, n-hexane:ethyl acetate=1:2) to give 1-(5-methylpyridin-2-yl)propan-2-one (2.60 g).

$^1$H-NMR (CDCl$_3$): δ2.22(3H,s), 2.32(3H,s), 3.88(2H,s), 7.11(1H,d,J=7.9 Hz), 7.47(1H,dd,J=7.9 Hz,1.8 Hz), 8.38 (1H,d,J=1.8 Hz)

EXAMPLE 5

To a stirred solution of 1-(5-methylpyridin-2-yl)propan-2-one (1.0 g) in dichloromethane (10 ml) was added a solution of hydrogen chloride in 1,4-dioxane (4N, 2.51 ml) dropwise at 5° C., and the mixture was stirred for 20 minutes. A solution of sulfuryl chloride (0.754 ml) in dichloromethane (10 ml) was added dropwise, and the mixture was stirred for 10 minutes. The mixture was evaporated under reduced pressure, and ethanol (10 ml) and 2-imino-4-thiobiuret (475 mg) were added. The mixture was stirred at 80° C. for 4 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was crystallized from ethyl acetate (12 ml), filtered, washed with ethyl acetate and dried to give 2-guanidino-4-methyl-5-(5-methylpyridin-2-yl)thiazole (254 mg).

$^1$H-NMR (DMSO-d$_6$): δ2.27(3H,s), 2.44(3H,s), 6.93(4H, broad s), 7.40(1H,d,J=8.2 Hz), 7.58(1H,dd,J-8.2 Hz,1.8 Hz), 8.32(1H,d,J=1.8 Hz)

Preparation 6

To a stirred solution of 4,5-dimethoxy-2-methylpyridine (2.92 g) in tetrahydrofuran (30 ml) was added a solution of n-butyllithium in n-hexane (1.63M, 14 ml) dropwise at −50° C. under a nitrogen atmosphere, and the mixture was warmed to 0° C. The mixture was cooled to −50° C., and N,N-dimethylacetamide (2.31 ml) was added dropwise. Then the mixture was warmed to room temperature, poured into a saturated aqueous ammonium chloride solution and extracted with ethyl acetate (100 ml×4). The combined organic layer was washed with brine, dried over sodium sulfate and evaporated under reduced pressure. The residue was purified by column chromatography (silica gel 100 g, n-hexane:ethyl acetate=1:1) to give 1-(4,5-dimethoxypyridin-2-yl)propan-2-one (1.59 g).

$^1$H-NMR (CDCl$_3$): δ2.12(3H,s), 3.7–3.9(8H,m), 6.94(1H, s), 8.05(1H,s)

EXAMPLE 6

To a stirred solution of 1-(4,5-dimethoxypyridin-2-yl) propan-2-one (0.79 g) in dichloromethane (15 ml) was added a solution of hydrogen chloride in 1,4-dioxane (4N, 2.52 ml) dropwise at 5° C., and the mixture was stirred for 30 minutes. A solution of sulfuryl chloride (0.453 ml) in dichloromethane (5 ml) was added dropwise, and the mixture was stirred for 30 minutes. The mixture was evaporated under reduced pressure, and ethanol (15 ml) and 2-imino-4-thiobiuret (792 mg) were added. The mixture was stirred at 70° C. for 2.5 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was purified by column chromatography (silica gel 75 g, 5–10% methanol in dichloromethane) and recrystallized from methanol (20 ml) and diisopropyl ether (30 ml) to give 2-guanidino-4-methyl-5-(4,5-dimethoxypyridin-2-yl)thiazole (373 mg).

$^1$H-NMR (DMSO-d$_6$): δ2.45(3H,s), 3.82(3H,s), 3.88(3H, s), 6.93(4H,broad s), 7.03(1H,s), 8.09(1H,s)

Preparation 7

To a stirred solution of 3,4-dimethoxy-2-methylpyridine (1.53 g) in tetrahydrofuran (15 ml) was added a solution of n-butyllithium in n-hexane (1.63M, 7.36 ml) dropwise at −50° C. under a nitrogen atmosphere, and the mixture was warmed to 0° C. The mixture was cooled to −50° C., and N,N-dimethylacetamide (1.21 ml) was added dropwise. Then the mixture was warmed to room temperature, poured into a saturated aqueous ammonium chloride solution and extracted with ethyl acetate (100 ml×2). The organic layer was washed with brine, dried over sodium sulfate and evaporated under reduced pressure. The residue was purified by column chromatography (silica gel 50 g, 25% ethyl acetate in n-hexane) to give 1-(3,4-dimethoxypyridin-2-yl) propan-2-one (1.85 g).

$^1$H-NMR (CDCl$_3$): δ2.23(3H,s), 3.81(3H,s), 3.91(3H,s), 3.94(2H,s), 6.78(1H,d,J=5.6 Hz), 8.19(1H,d,J=5.6 Hz)

EXAMPLE 7

To a stirred solution of 1-(3,4-dimethoxypyridin-2-yl) propan-2-one (781 mg) in dichloromethane (10 ml) was added a solution of hydrogen chloride in 1,4-dioxane (4N, 1.5 ml) dropwise at 5° C., and the mixture was stirred for 20 minutes. A solution of sulfuryl chloride (0.434 ml) in dichloromethane (10 ml) was added dropwise, and the mixture was stirred for 5 minutes. The mixture was evaporated under reduced pressure, and ethanol (10 ml), 2-imino-4-thiobiuret (472 mg) and triethylamine (0.557 ml) were added. The mixture was refluxed for 3.5 hours and cooled to ambient temperature. The solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was purified by column chromatography (silica gel 50 g, 5% methanol in dichloromethane) to give 2-guanidino-4-methyl-5-(3,4-dimethoxypyridin-2-yl)thiazole (547 mg).

$^1$H-NMR (DMSO-$d_6$): δ2.38(3H,s), 3.64(3H,s), 3.89(3H, s), 6.99(1H,d,J=5.5 Hz), 6.7–7.1(4H,broad s), 8.21(1H,d,J=5.5 Hz)

Preparation 8

To a suspension of sodium hydride (60% dispersion in mineral oil, 1.06 g) in 2-propanol (30 ml) was added 2-methyl-4-nitropyridine N-oxide (3.08 g), and the mixture was stirred at 60° C. for 1 hour. The residue was evaporated under reduced pressure and purified by column chromatography (silica gel 75 g, 5% methanol in dichloromethane) to give 4-isopropyloxy-2-methylpyridine N-oxide (0.78 g).

$^1$H-NMR (DMSO-$d_6$): δ1.27(6H,d,J=6.0 Hz), 2.30(3H,s), 4.66(1H,sep,J=6.0 Hz), 6.86(1H,dd,J=7.2 Hz,3.5 Hz), 7.09 (1H,d,J=3.5 Hz), 8.08(1H,d,J=7.2 Hz)

Preparation 9

A suspension of 4-isopropyloxy-2-methylpyridine N-oxide (0.78 g) in 2-propanol (10 ml) was hydrogenated over Raney-nickel (50% suspension in water, 1 ml) under a hydrogen atmosphere for 48 hours. The catalyst was filtered off, and the filtrate was evaporated under reduced pressure to give 4-isopropyloxy-2-methylpyridine (555 mg).

$^1$H-NMR (CDCl$_3$): δ1.26(6H,d,J=6.0 Hz), 2.27(3H,s), 4.72(1H,sep,J=6.0 Hz), 6.7–6.9(2H,m), 8.20(1H,d,J=5.7 Hz)

Preparation 10

To a stirred solution of 4-isopropyloxy-2-methylpyridine (687 mg) in tetrahydrofuran (7 ml) was added a solution of n-butyllithium in n-hexane (1.63M, 3.34 ml) dropwise at −50° C. under a nitrogen atmosphere, and the mixture was warmed to 0° C. The mixture was cooled to −50° C., and N,N-dimethylacetamide (0.549 ml) was added dropwise. Then the mixture was warmed to room temperature, poured into a saturated aqueous ammonium chloride solution and extracted with ethyl acetate (100 ml). The organic layer was washed with brine, dried over sodium sulfate and evaporated under reduced pressure. The residue was purified by column chromatography (silica gel 50 g, 25% ethyl acetate in n-hexane) to give 1-(4-isopropyloxypyridin-2-yl)-propan-2-one (652 mg).

$^1$H-NMR (CDCl$_3$): δ1.36(6H,d,J=6.1 Hz), 2.23(3H,s), 3.86(2H,s), 4.63(1H,sep,J=6.1 Hz), 6.6–6.8(2H,m), 8.34 (1H,d,J=6.2 Hz)

EXAMPLE 8

To a stirred solution of 1-(4-isopropyloxypyridin-2-yl) propan-2-one (641 mg) in dichloromethane (10 ml) was added a solution of hydrogen chloride in 1,4-dioxane (4N, 1.25 ml) dropwise at 5° C., and the mixture was stirred for 20 minutes. A solution of sulfuryl chloride (0.36 ml) in dichloromethane (10 ml) was added dropwise, and the mixture was stirred for 5 minutes. The mixture was evaporated under reduced pressure, and ethanol (10 ml), 2-imino-4-thiobiuret (275 mg) and triethylamine (0.323 ml) were added. The mixture was refluxed for 3 hours and cooled to ambient temperature. The solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was triturated with 2-propanol, filtered, washed with diisopropyl ether and dried to give 2-guanidino-4-methyl-5-(4-isopropyloxypyridin-2-yl)thiazole (200 mg).

$^1$H-NMR (DMSO-$d_6$): δ1.31(6H,d,J=6.0 Hz), 2.45(3H,s), 4.78(1H,sep,J=6.0 Hz), 6.74(1H,dd,J=5.8 Hz,2.3 Hz), 6.91 (1H,d,J=2.3 Hz), 6.8–7.1(4H,broad s), 8.27(1H,d,J=5.8 Hz)

Preparation 11

To a solution of dimethylamine in tetrahydrofuran (2M, 20 ml) was added 2-methyl-4-nitropyridine N-oxide (3.08 g), and the mixture was stirred at 60° C. for 8 hours. The residue was evaporated under reduced pressure and purified by column chromatography (silica gel 75 g, 0 to 10% methanol in dichloromethane) to give 4-dimethylamino-2-methylpyridine N-oxide (1.76 g).

$^1$H-NMR (DMSO-$d_6$): δ2.29(3H,s), 3.40(6H,s), 6.57(1H, dd,J=7.3 Hz,3.5 Hz), 6.72(1H,d,J=3.5 Hz), 7.90(1H,d,J=7.3 Hz)

Preparation 12

A suspension of 4-dimethylamino-2-methylpyridine N-oxide (1.67 g) in 2-propanol (15 ml) was hydrogenated over Raney-nickel (50% suspension in water, 1 ml) under a hydrogen atmosphere for 3 hours. The catalyst was filtered off, and the filtrate was evaporated under reduced pressure to give 4-dimethylamino-2-methylpyridine (1.35 g).

$^1$H-NMR (CDCl$_3$): δ2.30(3H,s), 3.32(6H,s), 6.3–6.5(2H, m), 7.97(1H,d,J=5.8 Hz)

Preparation 13

To a stirred solution of 4-dimethylamino-2-methylpyridine (1.30 g) in tetrahydrofuran (13 ml) was added a solution of n-butyllithium in n-hexane (1.56M, 7.34 ml) dropwise at −50° C. under a nitrogen atmosphere, and the mixture was warmed to 0° C. The mixture was cooled to −50° C., and N,N-dimethylacetamide (1.15 ml) was added dropwise. Then the mixture was warmed to room temperature, poured into a saturated aqueous ammonium chloride solution and extracted with ethyl acetate (100 ml×3). The combined organic layer was washed with brine, dried over sodium sulfate and-evaporated under reduced pressure. The residue was purified by column chromatography (silica gel 50 g, 20% methanol in dichloromethane) to give 1-(4-dimethylaminopyridin-2-yl)propan-2-one (1.29 g).

$^1$H-NMR (CDCl$_3$): δ2.28(3H,s), 3.07(6H,s), 3.96(2H,s), 6.4–6.6(2H,m), 8.12(1H,d,J=6.2 Hz)

EXAMPLE 9

To a stirred solution of 1-(4-dimethylaminopyridin-2-yl) propan-2-one (1.25 g) in dichloromethane (12.5 ml) was added a solution of hydrogen chloride in 1,4-dioxane (4N, 2.63 ml) dropwise at 5° C., and the mixture was stirred for 20 minutes. A solution of sulfuryl chloride (0.789 ml) in dichloromethane (15 ml) was added dropwise, and the mixture was stirred for 5 minutes. The mixture was evaporated under reduced pressure, and ethanol (15 ml), 2-imino-4-thiobiuret (413 mg) and triethylamine (0.976 ml) were added. The mixture was stirred at 50° C. for 2 hours and cooled to ambient temperature. The precipitate was collected by filtration, washed with ethanol, ethyl acetate and diisopropyl ether and recrystallized from dichloromethane/2-propanol to give 2-guanidino-4-methyl-5-(4-dimethylaminopyridin-2-yl)thiazole (395 mg).

$^1$H-NMR (DMSO-$d_6$): δ2.45(3H,s), 2.98(6H,s), 6.43(1H, dd,J=5.9 Hz,2.3 Hz), 6.62(1H,d,J=2.3 Hz), 6.8–7.2(4H, broad s), 8.03(1H,d,J=5.9 Hz)

Preparation 14

To a suspension of 2-amino-4-methyl-5-(4-methylpyridin-2-yl)-thiazole (615 mg) in acetone (5 ml) was added a solution of benzoyl isothiocyanate (0.443 ml) in acetone (5 ml) dropwise, and the mixture was heated under reflux for 3 hours. After cooling, the resulting precipitate was collected by filtration and dried to give N-(4-methyl-5-(4-methylpyridin-2-yl)thiazol-2-yl)-N'-benzoylthiourea (490 mg).

$^1$H-NMR (DMSO-d$_6$): δ2.41(3H, s) 2.59(3H ,s) , 7.19 (1H,d,J=5.1 Hz), 7.4–7.8(4H,m), 7.9–8.1(2H,m), 8.47(1H, d,J=5.1 Hz), 11.8–12.2(1H,broad s)

EXAMPLE 10

To a suspension of N-(4-methyl-5-(4-methylpyridin-2-yl)thiazol-2-yl)-N'-benzoylthiourea (700 mg) in methanol (7 ml) was added an aqueous sodium hydroxide solution (1N, 1.9 ml) dropwise. The mixture was stirred at 60° C. for 1 hour, cooled to ambient temperature, and the pH was adjusted to 8.0 with 1N hydrochloric acid. The mixture was diluted with water (50 ml) and stirred for 5 minutes. The precipitate was collected by filtration, washed with water and diisopropyl ether and dried under reduced pressure to give N-(4-methyl-5-(4-methylpyridin-2-yl)thiazol-2-yl)thiourea (438 mg).

$^1$H-NMR (DMSO-d$_6$): δ2.37(3H,s), 2.53 (3H,s), 7.09(1H, d,J=5.0 Hz), 7.45(1H,s), 8.40(1H,d,J=5.5 Hz), 8.7(2H,broad s), 11.64(1H,broad s)

EXAMPLE 11

To a suspension of N-(4-methyl-5-(4-methylpyridin-2-yl)thiazol-2-yl)thiourea (1.23 g) in N,N-dimethylformamide were added a solution of hydrogen chloride in 1,4-dioxane (4N, 2.56 ml) and iodoethane (1.86 ml), and the mixture was stirred at 70° C. for 4 hours. Ethyl acetate (100 ml) was added to the mixture, and the mixture was cooled. The precipitate was collected by filtration and purified by column chromatography (silica gel, triethylamine:methanol:dichloromethane=1:5:100) to give N-(4-methyl-5-(4-methylpyridin-2-yl)thiazol-2-yl)-S-ethylisothiourea (1.14 g).

$^1$H-NMR (DMSO-d$_6$): δ1.27(3H,t,J=7.3 Hz), 2.36(3H,s), 2.52(3H,s), 3.01(2H,q,J=7.3 Hz), 7.07(1H,d,J=5.0 Hz), 7.43 (1H,s), 8.39(1H,d,J=5.5 Hz), 8.99(2H,broad s)

EXAMPLE 12

To a suspension of N-(4-methyl-5-(4-methylpyridin-2-yl)thiazol-2-yl)-S-ethylisothiourea dihydrochloride (36.5 mg) in ethanol (0.5 ml) was added hydrazine hydrate (50 mg). The mixture was stirred at 80° C. for 1 hour and cooled to ambient temperature. The precipitate was collected by filtration, washed with ethanol, water and diisopropyl ether to give N-(4-methyl-5-(4-methylpyridin-2-yl)thiazol-2-yl)-N'-aminoguanidine (11 mg).

$^1$H-NMR (DMSO-d$_6$): δ2.14(3H,s), 2.47(3H,s), 4.48(2H, s), 6.97(1H,d,J=4.9 Hz), 7.30(1H,s), 7.2–7.8(2H,broad s), 8.32(1H,d,J=4.9 Hz), 8.69(1H,s)

EXAMPLE 13

To a suspension of hydroxylamine hydrochloride (146 mg) and sodium acetate (172 mg) in 2-propanol (4 ml) was added N-(4-methyl-5-(4-methylpyridin-2-yl)thiazol-2-yl)-S-ethylisothiourea (205 mg), and the mixture was stirred at 90° C. for 1 hour. The mixture was diluted with ethyl acetate and washed with water and brine. The organic layer was dried over sodium sulfate and evaporated under reduced pressure. The residue was purified by column chromatography (silica gel, 3 to 4% methanol in dichloromethane) to give N-(4-methyl-5-(4-methylpyridin-2-yl)thiazol-2-yl)-N'-hydroxyguanidine (81 mg).

$^1$H-NMR (DMSO-d$_6$): δ2.15(3H,s), 2.47(3H,s), 7.00(1H, d,J=5.0 Hz), 7.34(1H,s), 8.34(1H,d,J=5.0 Hz), 8.95(1H,s), 9.77(1H,s)

EXAMPLE 14

To a solution of ethylamine in ethanol (20% w/w, 10 ml) was added N-(4-methyl-5-(4-methylpyridin-2-yl)thiazol-2-yl)-S-ethylisothiourea (292 mg), and the mixture was heated in a steel autoclave at 110° C. for 17 hours. The mixture was evaporated under reduced pressure and crystallized from ethanol. The precipitate was collected by filtration to give N-ethyl-N'-(4-methyl-5-(4-methylpyridin-2-yl)-thiazol-2-yl)guanidine (124 mg).

$^1$H-NMR (DMSO-d$_6$): δ1.09(3H,t,J=7.2 Hz), 2.33(3H,s), 2.47(3H,s), 3.16(2H,q,J=7.2 Hz), 6.98(1H,d,J=7.1 Hz), 7.31 (1H,s), 7.3–7.8(3H,broad), 8.33 (1H,d,J=7.1 Hz)

EXAMPLE 15

To a stirred solution of 1-(4-methylpyridin-2-yl)propan-2-one (0.597 g) in dichloromethane (6 ml) was added a solution of hydrogen chloride in 1,4-dioxane (4N, 1 ml) dropwise at 50° C., and the mixture was stirred for 20 minutes. A solution of sulfuryl chloride (0.45 ml) in dichloromethane (4 ml) was added dropwise, and the mixture was stirred for 10 minutes. The mixture was evaporated under reduced pressure, and ethanol (10 ml) and 1,1-dimethyl-2-imino-4-thiobiuret (467 mg) were added. The mixture was stirred at 90° C. for 3 hours and cooled to ambient temperature. The solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. To the residue was added a solution of hydrogen chloride in 1,4-dioxane (4N, 0.161 ml). The precipitate was collected by filtration, washed with ethyl acetate and dried to give N,N-dimethyl-N'-(4-methyl-5-(4-methylpyridin-2-yl)-thiazol-2-yl) guanidine hydrochloride (204 mg).

$^1$H-NMR (DMSO-d$_6$): δ2.38(3H,s), 2.49(3H,s), 3.09(6H, s), 7.15(1H,d,J=7.0 Hz), 7.48(1H,s), 7.9–8.2(2H,broad), 8.40(1H,d,J=7.0 Hz), 12.6–13.0(1H,broad)

EXAMPLE 16

To a suspension of 2-amino-4-methyl-5-(4-methylpyridin-2-yl)-thiazole (308 mg) and potassium carbonate (207 mg) in N,N-dimethylformamide (5 ml) was added N-cyano-N',S-dimethylisothiourea (194 mg), and the mixture was stirred at 100° C. for 12 hours. The mixture was poured into water and extracted with ethyl acetate-tetrahydrofuran (2:1, 150 ml×2). The organic layer was washed with brine and evaporated under reduced pressure. The residue was purified by column chromatography (silica gel 10 g, 0 to 2% methanol in dichloromethane) to give 2,4-dicyano-1,3-dimethyl-5-(4-methyl-5-(4-methylpyridin-2-yl)thiazol-2-yl)biguanide (41 mg) as a mixture of regioisomers.

$^1$H-NMR (DMSO-d$_6$): δ2.24(3H,s), 2.66(3H,s), 2.8–3.0 (6H,m), 7.23(1H,d,J=5.0 Hz), 7.51(1H,m), 7.63(1H,s), 7.6–8.4(2H,m), 8.49(1H,d,J=5.0 Hz)

EXAMPLE 17

To a suspension of 2-amino-4-methyl-5-(4-methylpyridin-2-yl)-thiazole and 2-(methylthio)-2- thiazoline (127 mg) in methoxyethanol (2 ml) was added a solution of hydrogen chloride in 1,4-dioxane (4N, 0.23 ml). The mixture was refluxed for 20 hours, poured into a saturated aqueous sodium hydrogencarbonate solution and extracted with ethyl acetate twice. The combined organic layer was washed with brine, dried over sodium sulfate and evaporated under reduced pressure. The residue was purified by column chromatography (silica gel 25 g, 5% methanol in dichloromethane) and recrystallized from chloroform (1 ml)-diisopropyl ether (3 ml) to give 2-(4-methyl-5-(4-methylpyridin-2-yl)thiazol-2-ylamino)-2-thiazoline (110 mg).

$^1$H-NMR (DMSO-d$_6$): δ2.35(3H,s), 2.51(3H,s), 3.6–3.8 (4H,broad), 7.04(1H,d,J=5.1 Hz), 7.40(1H,s), 8.37(1H,d,J= 5.1 Hz), 8.6–9.0(1H,broad s)

EXAMPLE 18

To a suspension of N-(4-methyl-5-(4-methylpyridin-2-yl) thiazol-2-yl)thiourea (529 mg) in N,N-dimethylformamide (10 ml) were added a solution of hydrogen chloride in 1,4-dioxane (4N, 1 ml) and iodoethane (0.8 ml), and the mixture was stirred at 70° C. for 4 hours. Ethyl acetate (100 ml) was added to the mixture, and the mixture was cooled. The precipitate was collected by filtration and purified by column chromatography (silica gel, triethylamine:methanol:dichloromethane=1:2:100). The combined fractions were evaporated under reduced pressure, and the residue was dissolved in ethyl acetate (5 ml). To the solution was added a solution of hydrogen chloride in 1,4-dioxane (4N, 1.25 ml). The precipitate was collected by filtration and dried under reduced pressure to give N-(4-methyl-5-(4-methylpyridin-2-yl)thiazol-2-yl)-S-ethylisothiourea dihydrochloride (0.69 g).

$^1$H-NMR (DMSO-d$_6$): δ1.33(3H,t,J=7.3 Hz), 2.43(3H,s), 2.59(3H,s), 3.25(2H,q,J=7.3 Hz), 7.28(1H,d,J=5.2 Hz), 7.61 (1H,s), 8.47(1H,d,J=5.2 Hz), 9.49(2H,broad s)

EXAMPLE 19

To a suspension of 2-amino-4-methyl-5-(4-methylpyridin-2-yl)-thiazole (410 mg) and potassium carbonate (415 mg) in N,N-dimethylformamide (10 ml) was added dimethyl N-cyanodithioimino-carbonate (292 mg), and the mixture was stirred at 100° C. for 1 hour. The mixture was poured into a saturated aqueous solution of ammonium chloride. Then the precipitate was collected by filtration, purified by column chromatography (silica gel 30 g, 0 to 3% methanol in dichloromethane) and recrystallized from 2-propanol to give N-cyano-N'-(4-methyl-5-(4-methylpyridin-2-yl) thiazol-2-yl)-S-methylisothiourea (0.08 g).

$^1$H-NMR (DMSO-d$_6$): δ2.38(3H,s), 2.56(3H,s), 2.58(3H, s), 7.18(1H,d,J=5.3 Hz), 7.51(1H,m), 8.45(1H,d,J=5.3 Hz), 13.53(1H,broad s)

EXAMPLE 20

A solution of 2-amino-4-methyl-5-(4-methylpyridin-2-yl) thiazole (300 mg) in N,N-dimethylformamide dimethyl acetal (1.5 ml) was stirred at ambient temperature for 14 hours and evaporated under reduced pressure. The residue was triturated with 2-propanol (1 ml) and diisopropyl ether, and the solid was collected by filtration, washed with diisopropyl ether and dried under reduced pressure to give N,N-dimethyl-N'-(4-methyl-5-($^4$-methylpyridin-2-yl) thiazol-2-yl)-formamidine (268 mg).

$^1$H-NMR (DMSO-d$_6$): δ2.34(3H,s), 2.98(3H,s), 3.12(3H, s), 7.02(1H,d,J=5.1 Hz), 7.37(1H,s), 8.34(1H,s), 8.37(1H,d, J=5.1 Hz)

EXAMPLE 21

A suspension of 2-amino-4-methyl-5-(4-methylpyridin-2-yl)thiazole (205 mg), ethyl acetimidate hydrochloride (370 mg) and diisopropylethylamine (0.697 ml) in N,N-dimethylformamide (4 ml) was stirred at ambient temperature for 10 days and evaporated under reduced pressure. To the residue was added hydrogen chloride in ethyl acetate (4N, 4 ml) and crystallized from methanol and ethyl acetate. The precipitate was collected by filtration and recrystallized from methanol and 2-propanol to give N-(4-methyl-5-(4-methylpyridin-2-yl)thiazol-2-yl)acetamidine dihydrochloride (220 mg).

$^1$H-NMR (DMSO-d$_6$): δ2.43(3H,s), 2.46(3H,s), 2.65(3H, s), 7.26(1H,d,J=5.1 Hz), 7.63(1H,s), 8.47(1H,d,J=5.1 Hz), 10.4–10.7(1H,broad s), 10.8–11.2(1H,broad s), 13.7–14.1 (1H,broad s)

EXAMPLE 22

To a stirred solution of 1-(4-methylpyridin-2-yl)propan-2-one (0.35 g) in dichloromethane (5 ml) was added a solution of hydrogen chloride in 1,4-dioxane (4N, 0.88 ml) dropwise at 5° C., and the mixture was stirred for 15 minutes. A solution of sulfuryl chloride (0.264 ml) in dichloromethane (5 ml) was added dropwise, and the mixture was stirred for 30 minutes. The mixture was evaporated under reduced pressure, and ethanol (15 ml) and 2-pyridylthiourea (216 mg) were added. The mixture was stirred at 60° C. for 2 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was purified by column chromatography (silica gel 25 g, 2% methanol in dichloromethane) and recrystallized from methanol and dichloromethane to give 2-(2-pyridylamino)-4-methyl-5-(4-methylpyridin-2-yl)thiazole (297 mg).

$^1$H-NMR (DMSO-d$_6$): δ2.37(3H,s), 2.55(3H,s), 6.93(1H, t,J=6.1 Hz), 7.0–7.2(2H,m), 7.43(1H,s), 7.70(1H,t,7.8 Hz), 8.34(1H,d,J=5.1 Hz), 8.39(1H,d,J=3.0 Hz), 11.34(1H,s)

Preparation 15

To a stirred solution of 2-chloro-4-methylthiazole (6.35 g) in tetrahydrofuran (50 ml) was added a solution of n-butyllithium in n-hexane (1.66M, 34.35 ml) dropwise at −70° C. under a nitrogen atmosphere, and the mixture was stirred for 20 minutes at −70° C. To the resultant mixture was added a solution of 2-cyano-4-methylpyridine (3.74 g) in tetrahydrofuran (30 ml) dropwise at −70° C., and the mixture was stirred for 15 minutes. The mixture was poured into a saturated aqueous ammonium chloride solution and extracted with ethyl acetate. The organic layer was washed with brine, dried over magnesium sulfate and evaporated. The residue was purified by column chromatography (silica gel 240 g, n-hexane:ethyl acetate=10:1) to give 2-chloro-4-methyl-5-(4-methylpyridin-2-ylcarbonyl)thiazole (1.64 g).

$^1$H-NMR (CDCl$_3$): δ2.47(3H,s), 2.86(3H,s), 7.34(1H,dd, J=4.9 Hz,0.9 Hz), 8.04(1H,d,J=0.9 Hz), 8.54(1H,d,J=4.9 Hz)

m.p. 115–116° C.

EXAMPLE 23

To a suspension of guanidine carbonate (456 mg) in methanol (4 ml) was added a solution of sodium methoxide in methanol (28%, 928 mg), and the mixture was stirred for 2 hours. The precipitate was removed by filtration, and the filtrate was evaporated under reduced pressure. To the residue were added 1,4-dioxane (6 ml) and 2-chloro-4-methyl-5-(4-methylpyridin-2-ylcarbonyl)thiazole (64 mg). The resultant mixture was refluxed for hour, poured into a saturated aqueous sodium hydrogencarbonate solution and extracted with ethyl acetate. The organic layer was washed with brine, dried over sodium sulfate and evaporated under reduced pressure. The residue was recrystallized from ethyl acetate/n-hexane to give 2-guanidino-4-methyl-5-(4-methylpyridin-2-ylcarbonyl)thiazole (56 mg).

$^1$H-NMR (CDCl$_3$): δ1.7–1.9(1H,m 2.1–2.4(1H,m), 2.25 (3H,s), 3.2–3.4(1H,m), 3.5–3.8(4H,m), 6.16(1H,s), 6.38(1H, d,J=5.2 Hz), 8.01(1H,d,J=5.2 Hz)

EXAMPLE 24

To a suspension of 2-guanidino-4-methyl-5-(4-methylpyridin-2-ylcarbonyl)thiazole (0.1 g) in methanol (3 ml) was added sodium borohydride. (48.4 mg), and the mixture was stirred for 2 hours. The mixture was poured into 1N hydrochloric acid. The pH was adjusted to 12 with 4N aqueous sodium hydroxide, and the mixture was stirred for 15 minutes. The precipitate was collected by filtration, washed with water and dried to give N-(5-(hydroxy-(4-methylpyridin-2-yl)methyl)-4-methylthiazol-2-yl)guanidine (92 mg).

$^1$H-NMR (DMSO-d$_6$): δ2.18(3H,s), 2.32(3H,s), 5.79(1H, d,J=3.0 Hz), 5.96(1H,d,J=3.0 Hz), 6.76(4H,broad s), 7.06 (1H,d,J=5.0 Hz), 7.33(1H,s), 8.29(1H,d,J=5.0 Hz)

m.p. 150.5–151.5° C.

EXAMPLE 25

A solution of N-(5-(hydroxy-(4-methylpyridin-2-yl) methyl)-4-methylthiazol-2-yl)guanidine (65 mg) and triethylsilane (300 mg) in trifluoroacetic acid (3 ml) was stirred for 48 hours and then evaporated under reduced pressure. Water was added, and the pH was adjusted to 12 with 4N aqueous sodium hydroxide. The resultant mixture was extracted with ethyl acetate. The organic layer was washed with brine, dried over sodium sulfate and-evaporated under reduced pressure. The residue was crystallized from dichloromethane to give N-(5-($^4$-methylpyridin-2-ylmethyl)-4-methylthiazol-2-yl)-guanidine (27 mg).

$^1$H-NMR (DMSO-d$_6$): δ2.15(3H,s), 2.27(3H,s), 3.95(2H, s), 6.75(4H,broad s), 6.9–7.1(2H,m), 8.31(1H,dd,J=4.6 Hz,1.3 Hz)

EXAMPLE 26

A solution of N-(5-(hydroxy-(4-methylpyridin-2-yl) methyl)-4-methylthiazol-2-yl)guanidine (0.54 g) and 96% sulfuric acid (6.5 ml) in acetonitrile (26 ml) was stirred at 5° C. for 18 hours. The pH of the mixture was adjusted to 12 with 4N aqueous sodium hydroxide, and the mixture was extracted with ethyl acetate three times. The combined organic layer was washed with brine, dried over sodium sulfate and evaporated under reduced pressure. The residue was triturated with ethyl acetate, collected by filtration and dried. The crude compound was recrystallized from ethanol/n-hexane to give N-(5-(acetylamino-(4-methylpyridin-2-yl) methyl)-4-methylthiazol-2-yl)-guanidine (211 mg).

m.p. 239–240° C.

$^1$H-NMR (DMSO-d$_6$): δ1.88(3H,s), 2.17(3H,s), 2.30(3H, s), 6.19(1H,d,J=8.0 Hz), 6.77(4H,broad s), 7.10(1H,d,J=5.0 Hz), 7.20(1H,s), 8.36(1H,d,J=5.0 Hz), 8.57(1H,d,J=8.0 Hz)

EXAMPLE 27

To a suspension of N-(5-(acetylamino-(4-methylpyridin-2-yl)-methyl)-4-methylthiazol-2-yl)guanidine (176 mg) in methanol (8.8 ml) was added hydrochloric acid (6 N, 4.6 ml), and the mixture was stirred at 90° C. for 4 hours. The mixture was evaporated under reduced pressure. The residue was recrystallized from ethanol to give N-(5-(amino-(4-methylpyridin-2-yl)methyl)-4-methylthiazol-2-yl)-guanidine trihydrochloride (141 mg).

$^1$H-NMR (DMSO-d$_6$): δ2.35(3H,s), 2.46(3H,s), 5.99(1H, broad d,J=3.9 Hz), 7.32(1H,d,J=5.0 Hz), 7.43(1H,s), 8.32 (4H,broad s), 8.56(1H,d,J=5.0 Hz), 9.04(3H,broad s)

Preparation 16

To a stirred solution of 2-chloro-4-methylthiazole (0.3 g) in tetrahydrofuran (3 ml) was added a solution of n-butyllithium in n-hexane (1.63M, 1.52 ml) dropwise at −70° C. under a nitrogen atmosphere, and the mixture was stirred for 20 minutes at −70° C. To the resultant mixture was added N,N-dimethylformamide (0.21 ml) at −70° C., and the mixture was stirred for 40 minutes. The mixture was poured into a saturated aqueous ammonium chloride solution and extracted with ethyl acetate. The organic layer was washed with brine, dried over magnesium sulfate and evaporated. The residue was purified by column chromatography (silica gel 10 g, n-hexane:ethyl acetate=10:1) to give 2-chloro-5-formyl-4-methylthiazole (231 mg).

$^1$H-NMR (CDCl$_3$): δ2.71(3H,s), 10.00(1H,s)

m.p. 77–78° C.

Preparation 17

To a suspension of guanidine carbonate (3.34 g) in methanol (18 ml) was added a solution of sodium methoxide in methanol (28%, 6.8 g), and the mixture was stirred for 2 hours. The solid was removed by filtration, and the filtrate was evaporated under reduced pressure. To the residue were added methanol (10 ml) and 2-chloro-5-formyl-4-methylthiazole (0.3 g). The resultant mixture was stirred for 20 hours, poured into a saturated aqueous sodium hydrogencarbonate solution and extracted with ethyl acetate. The organic layer was washed with brine, dried over sodium sulfate and evaporated under reduced pressure. The residue was recrystallized from ethanol to give 5-formyl-2-guanidino-4-methylthiazole (197 mg).

$^1$H-NMR (DMSO-d$_6$): δ2.46(3H,s), 7.28(4H,broad s), 9.80(1H,s)

m.p. 176–178° C.

EXAMPLE 28

To a suspension of 5-formyl-2-guanidino-4-methylthiazole (1.0 g) and 2-amino-4-picoline (587 mg) in N,N-dimethylformamide (10 ml) and dichloromethane (60 ml) was added sodium triacetoxyborohydride (1.82 g), and the mixture was stirred for 140 hours. The mixture was evaporated under reduced pressure, and to the residue was added hydrochloric acid (1N, 12 ml). The pH was adjusted to 12 with 4N aqueous sodium hydroxide. The mixture was extracted with ethyl acetate twice. The combined organic layer was washed with brine, dried over sodium sulfate and evaporated under reduced pressure. The residue was purified by column chromatography (silica gel 50 g, 5% methanol in dichloromethane), and the fractions containing objective compound were combined and evaporated. The residue was dissolved in ethanol, and to the solution was added a solution of hydrogen chloride in 1,4-dioxane (4N, 2 ml). The precipitate was collected by filtration, washed with ethyl acetate-ethanol (1:1, 3 ml) and dried to give N-(5-(4-methylpyridin-2-ylaminomethyl)-4-methylthiazol-2-yl)-guanidine dihydrochloride (513 mg).

$^1$H-NMR (DMSO-d$_6$): δ2.33(3H,s), 2.35(3H,s), 4.76(2H, broad s), 6.79(1H,d,J=6.5 Hz), 6.94(1H,s), 7.90(1H,d,J=6.5 Hz), 8.31(4H,s), 9.01(1H,broad s)

EXAMPLE 29

To a stirred solution of 1-(4-methylpyridin-2-yl)propan-2-one (0.6 g) in acetic acid (5 ml) was added a solution of hydrogen bromide in acetic acid (30%, 2 ml). To the mixture was added pyridinium hydrobromide perbromide (1.28 g). The mixture was stirred at ambient temperature for 3 hours. The mixture was evaporated under reduced pressure, and ethanol (10 ml) and 2-imino-4-thiobiuret (472 mg) were added. The mixture was stirred at 80° C. for 4 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was triturated with 2-propanol and diisopropyl ether (1:1), filtered, washed with diisopropyl ether and dried to give 2-guanidino-4-(4-methylpyridin-2-ylmethyl)thiazole (677 mg).

$^1$H-NMR (DMSO-d$_6$): δ2.26(3H,s), 3.91(2H,s), 6.29(1H, s), 6.80(4H,broad s), 7.04(1H,d,J=5.0 Hz), 7.09(1H,s), 8.31 (1H,d,J=5.0 Hz)

EXAMPLE 30

To a stirred solution of 1-(3-methylisoxazol-5-yl)propan-2-one (0.14 g) in chloroform (2 ml) was added a solution of sulfuryl chloride (136 mg) in chloroform (1 ml) dropwise, and the mixture was stirred for 10 minutes. The mixture was evaporated under reduced pressure, and methanol (3 ml) and 2-imino-4-thiobiuret (119 mg) were added. The mixture was stirred at 80° C. for 4 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was crystallized from methanol, collected by filtration and dried to give 2-guanidino-4-methyl-5-(3-methylisoxazol-5-yl)thiazole (63 mg).

$^1$H-NMR (DMSO-d$_6$): δ2.23(3H,s), 2.36(3H,s), 6.33(1H, s), 7.04(4H,s)

Preparation 18

A suspension of 2-fluoro-4-methylpyridine (1.11 g), 3-(tert-butoxycarbonylamino)pyrrolidine (1.68 g) and potassium carbonate (1.49 g) in N,N-dimethylformamide (20 ml) was stirred at 100° C. for 16 hours. After cooling, the mixture was poured into water and extracted with ethyl acetate. The organic layer was washed with water five times and brine, dried over sodium sulfate and evaporated under reduced pressure to give 1-(4-methylpyridin-2-yl)-3-(tert-butoxycarbonylamino)pyrrolidine (1.36 g).

$^1$H-NMR (CDCl$_3$): δ1.45(9H,s), 1.9–2.1(1H,m), 2.2–2.4 (1H,m), 2.25(3H,s), 3.3–3.8(4H,m), 4.2–4.4(1H,m), 4.6–4.8 (1H,m), 6.18(1H,s), 6.41(1H,d,J=5.0 Hz), 8.01(1H,d,J=5.0 Hz)

Preparation 19

To a solution of 1-(4-methylpyridin-2-yl)-3-(tert-butoxycarbonylamino)pyrrolidine (0.72 g) in dichloromethane (5 ml) was added a solution of hydrogen chloride in 1,4-dioxane (5 ml) and the resultant mixture was stirred at ambient temperature for 3 hours and evaporated under reduced pressure. To the residue was added 1N aqueous sodium hydroxide (30 ml) and extracted with ethyl acetate-tetrahydrofuran (2:1) three times. The combined organic layer was washed with brine, dried over sodium sulfate and evaporated under reduced pressure to give 3-amino-1-(4-methylpyridin-2-yl)pyrrolidine (409 mg).

$^1$H-NMR (CDCl$_3$): δ1.7–1.9(lH,m), 2.1–2.4(1H,m), 2.25 (3H,s), 3.2–3.4(1H,m), 3.5–3.8(4H,m), 6.16(1H,s), 6.38(1h, d,J=5.2 Hz), 8.01(1H,d,J=5.2 Hz)

EXAMPLE 31

To a suspension of 3-amino-1-(4-methylpyridin-2-yl) pyrrolidine (177 mg) and N,N'-bis(tert-butoxycarbonyl) thiourea (331 mg) and diisopropylethylamine (0.4 ml) in dichloromethane (10 ml) was added 1-methyl-2-chloropyridinium iodide (332 mg), and the mixture was stirred for 16 hours. The mixture was diluted with ethyl acetate, washed with water and brine, dried over magnesium sulfate and evaporated under reduced pressure. The residue was purified by column chromatography (silica gel 25 g, n-hexane:ethyl acetate=4:1) and crystallized from diisopropyl ether to give N,N'-bis(tert-butoxycarbonyl)-N"-(1-(4-methylpyridin-2-yl)pyrrolidin-3-yl)guanidine (290 mg).

$^1$H-NMR (CDCl$_3$): δ1.47(9H,s), 1.51(9H,s), 1.9–2.1(1H, m), 2.2–2.4(1H,m), 2.21(3H,s), 3.3–3.9(4H,m), 4.8–5.0(1H, m), 6.20(1H,s), 6.42(1H,d,J=5.2 Hz), 8.02(1H,d,J=5.2 Hz), 8.57(1H,d,7.2 Hz), 11.47(1H,s)

EXAMPLE 32

To a solution of N,N'-bis(tert-butoxycarbonyl)-N"-(1-(4-methylpyridin-2-yl)pyrrolidin-3-yl)guanidine (210 mg) in dichloromethane (4 ml) was added a solution of hydrogen chloride in 1,4-dioxane (4N, 4 ml), and the mixture was stirred at ambient temperature for 24 hours. The solvent was evaporated under reduced pressure. To the residue was added 10% methanol in ethyl acetate (50 ml). The resultant precipitate was collected by filtration and dried under reduced pressure to give (1-(4-methylpyridin-2-yl)-pyrrolidin-3-yl)guanidine dihydrochloride (140 mg).

$^1$H-NMR (DMSO-d$_6$): δ2.0–2.4(2H,m), 2.39(3H,s), 3.4–4.0(6H,m), 4.45(1H,broad s), 6.82(1H,d,6.5 Hz), 6.97 (1H,s), 7.2–7.8(4H,broad s), 7.89(1H,d,J=6.5 Hz), 8.72 (1H, d,J=7.7 Hz), 13.80 (1H,broad s)

EXAMPLE 33

To a solution of 3-amino-1-(4-methylpyridin-2-yl) pyrrolidine (177 mg) and N-(tert-butoxycarbonyl)-N'-ethylthiourea (245 mg) in N,N-dimethylformamide (5 ml) was added 1-ethyl-3-(3-dimethylaminopropyl)-carbodiimide hydrochloride (230 mg), and the mixture was stirred for 18 hours. The mixture was diluted with ethyl acetate, washed with water three times and brine, dried over sodium sulfate and evaporated under reduced pressure. The residue was purified by column chromatography (silica gel 25 g, 5% methanol in dichloromethane) to give N-(tert-butoxycarbonyl)-N'-ethyl-N"-(1-(4-methylpyridin-2-yl))-pyrrolidin-3-yl)guanidine (290 mg).

$^1$H-NMR (CDCl$_3$): δ1.24(3H,t,J=7.2 Hz), 1.49(9H,s), 1.8–2.1(2H,m), 2.2–2.4(1H,m), 2.26(3H,s), 3.1–3.9(7H,m), 4.6–4.8(1H,broad s), 6.20(1H,s), 6.44(1H,d,J=5.2 Hz), 8.02 (1H,d,J=5.2 Hz)

EXAMPLE 34

To a solution of N-(tert-butoxycarbonyl)-N'-ethyl-N"-(1-(4-methylpyridin-2-yl)pyrrolidin-3-yl)guanidine (200 mg) in ethanol (2 ml) was added a solution of hydrogen chloride in 1,4-dioxane (4N, 3 ml), and the mixture was stirred at ambient temperature for 6 hours. The solvent was evaporated under reduced pressure. To the residue was added 10% ethanol in ethyl acetate (50 ml), and the resultant precipitate was collected by filtration and dried under reduced pressure to give N-ethyl-N'-(1-(4-methylpyridin-2-yl)pyrrolidin-3-yl)guanidine dihydrochloride (120 mg).

$^1$H-NMR (D$_2$O): δ1.24(3H,t,J=7.2 Hz), 2.2–2.6(2H,m), 2.43(3H,s), 3.24(2H,q,J=7.2 Hz), 3.5–4.0(4H,m), 4.4–4.6 (1H,m), 6.8–7.0(2H,m), 7.73(1H,d,J=6.5 Hz)

Preparation 20

A suspension of 2-acetyl-4-methylpyridine (0.65 g) in N,N-dimethylformamide dimethyl acetal (4 ml) was refluxed for 10 hours and evaporated under reduced pressure. The residue was triturated with diisopropyl ether, filtered and dried under reduced pressure to give 3-dimethylamino-1-(4-methylpyridin-2-yl)prop-2-en-1-one (777 mg).

$^1$H-NMR (DMSO-d$_6$): δ2.37(3H,s), 2.91(3H,s), 3.16(3H,s), 6.36(1H,d,J=12.7 Hz), 7.32(1H,d,J=4.9 Hz), 7.7–7.9(2H,m), 8.47(1H,d,J=4.9 Hz)

Preparation 21

To a suspension of 3-dimethylamino-1-(4-methylpyridin-2-yl)prop-2-en-1-one (0.78 g) and cyanoguanidine (1.38 g) in ethanol (8 ml) was added a solution of sodium methoxide in methanol (28%, 1.49 ml), and the mixture was refluxed for 2 hours. The mixture was neutralized with 1N hydrochloric acid and extracted with ethyl acetate and tetrahydrofuran (3:1). The organic layer was washed with brine, dried over sodium sulfate and evaporated under reduced pressure. The residue was purified by column chromatography (silica gel 75 g, 10% methanol in dichloromethane). The solid obtained was triturated with 2-propanol, filtered and dried to give N-(4-(4-methylpyridin-2-yl)-pyrimidin-2-yl)cyanamide (325 mg).

$^1$H-NMR (DMSO-d$_6$): δ2.45(3H,s), 7.46 (1H,dd,J=4.9 Hz,0.9 Hz), 7.85(1H,d,J=5.8 Hz), 8.19(1H,t,J=0.9 Hz), 8.6–8.8(2H,m), 12.0–12.6(1H,broad s)

EXAMPLE 35

To a solution of ethylamine in ethanol (20 w/w %, 5 ml) was added N-(4-(4-methylpyridin-2-yl)pyrimidin-2-yl) cyanamide (150 mg). The mixture was heated in a steel autoclave at 120° C. for 4.5 hours. After cooling, the solvent was evaporated under reduced pressure. To the residue was added 2-propanol, and the resultant precipitate was collected by filtration and dried under reduced pressure to give N-ethyl-N'-(4-(4-methylpyridin-2-yl)pyrimidin-2-yl) guanidine (50 mg).

$^1$H-NMR (DMSO-d$_6$): δ1.15(3H,t,J=7.6 Hz), 2.42(3H,s), 3.28(2H,q,J=7.6 Hz), 7.36(1H,d,J=7.1 Hz), 7.4–7.8(3H,broad s), 7.54(1H,d,J=4.9 Hz), 8.14(1H,s), 8.51(lH,d,J=7.1 Hz), 8.56(1H,d,J=4.9 Hz)

Preparation 22

A suspension of 2-fluoro-4-methylpyridine (1.11 g), 4-nitroimidazole (1.24 g) and potassium carbonate (1.65 g) in N,N-dimethylformamide (10 ml) was stirred at 130° C. for 21 hours. After cooling, the mixture was poured into water and stirred for 30 minutes. The precipitate was collected by filtration and dried to give 1-(4-methylpyridin-2-yl)-4-nitroimidazole (698 mg).

$^1$H-NMR (CDCl$_3$): δ2.50(3H,s), 7.22(1H,d,J=5.0 Hz), 7.30(1H,s), 8.29(1H,s), 8.40(1H,d,J=1.5 Hz), 8.48(1H,d,J=1.5 Hz)

EXAMPLE 36

A suspension of 1-(4-methylpyridin-2-yl)-4-nitroimidazole (204 mg) in ethanol (5 ml) was hydrogenated over palladium on carbon (10% w/w, 50% wet, 50 mg) under a hydrogen atmosphere for 5.5 hours. The catalyst was filtered off, and the filtrate was evaporated under reduced pressure. The residue was dissolved in dichloromethane (10 ml). To the solution were added N,N'-bis(tert-butoxycarbonyl)thiourea (331 mg), 1-methyl-2-chloropyridinium iodide (332 mg) and diisopropylethylamine (0.4 ml), and the mixture was stirred at ambient temperature for 12 hours. The resultant suspension was diluted with dichloromethane and washed with water and brine. The separated organic layer was dried over sodium sulfate and evaporated under reduced pressure. The residue was purified by column chromatography (silica gel 25 g, n-hexane:ethyl acetate=1:1) to give N,N'-bis(tert-butoxycarbonyl)-N"-(1-(4-methylpyridin-2-yl)-imidazol-4-yl)guanidine (260 mg).

$^1$H-NMR (CDCl$_3$): δ1.53(9H,s), 1.54(9H,s), 2.57(3H,s), 7.04(1H,d,J=5.1 Hz), 7.20(1H,s), 7.94(1H,d,J=1.5 Hz), 8.25 (1H,d,J=1.5 Hz), 8.31(1H,d,J=5.1 Hz), 11.35 (1H,broad s)

EXAMPLE 37

To a solution of N,N'-bis(tert-butoxycarbonyl)-N"-(1-(4-methylpyridin-2-yl)imidazol-4-yl)guanidine (200 mg) in dichloromethane (2 ml) was added a solution of hydrogen chloride in 1,4-dioxane (4N, 4 ml), and the mixture was stirred at ambient temperature for 23 hours. The solvent was evaporated under reduced pressure. To the residue was added 2-propanol, and the resultant precipitate was collected by filtration and dried under reduced pressure to give (1-(4-methylpyridin-2-yl)imidazol-4-yl)guanidine dihydrochloride (94 mg).

$^1$H-NMR (DMSO-d$_6$): δ2.24(3H,s), 7.27(1H,d,J=5.0 Hz), 7.6–8.0(6H,m), 8.37(1H,d,J=5.0 Hz), 8.60 (1H,d,J=1.4 Hz), 10.51(1H,s)

Preparation 23

To a stirred suspension of 2-cyano-4-methylpyridine (1.0 g) in tetrahydrofuran (10 ml) was added a solution of ethylmagnesium bromide in tetrahydrofuran (0.96M, 9.7 ml) dropwise at −55° C. The reaction mixture was stirred at −55° C. for 30 minutes and warmed to 0° C. Then the mixture was poured into a saturated aqueous ammonium chloride solution and extracted with ethyl acetate twice. The combined organic layer was washed with brine, dried over magnesium sulfate and evaporated under reduced pressure to give 1-(4-methylpyridin-2-yl)-propan-1-one (1.21 g).

$^1$H-NMR (CDCl$_{13}$): δ; 1.21 (3H,t,J=7.3 Hz), 2.42(3H,s), 3.23(2H,q,J=7.3 Hz), 7.27(1H,d,J=5.0 Hz), 7.86(1H,s), 8.52 (1H,d,J=5.0 Hz)

Preparation 24

To a stirred solution of 1-(4-methylpyridin-2-yl)propan-1-one (0.9 g) in chloroform (5 ml) was added a solution of sulfuryl chloride (0.533 ml) in chloroform (5 ml) dropwise. The resultant mixture was refluxed for 2 hours and evaporated under reduced pressure. The pH was adjusted to 8.5 with a saturated aqueous sodium hydrogencarbonate solution, and the mixture was extracted with ethyl acetate twice. The combined organic layer was washed with brine, dried over magnesium sulfate and evaporated under reduced pressure. The residue was purified by column chromatography (silica gel 25 g, n-hexane:dichloromethane=1:1) to give 2-chloro-1-(4-methylpyridin-2-yl)propan-1-one (0.71 g).

$^1$H-NMR (CDCl$_3$): δ1.75(3H,d,J=6.9 Hz), 2.45(3H,s), 6.00(1H,q,J=6.9 Hz), 7.32 (1H,dd,J=4.9 Hz, 0.8 Hz), 7.93 (1H,d,J=0.8 Hz), 8.52(1H,d,J=4.9 Hz)

EXAMPLE 38

To a solution of 2-chloro-1-(4-methylpyridin-2-yl) propan-1-one (0.4 g) in ethanol (5 ml) was added 2-imino- 4-thiobiuret (257 mg). The mixture was refluxed for 2 hours, and the solvent was evaporated under reduced pressure. To the residue were added ethyl acetate and a saturated aqueous sodium hydrogencarbonate solution. The ethyl acetate layer was separated, washed with brine, dried over sodium sulfate and evaporated under reduced pressure. The residue was purified by column chromatography (silica gel 25 g, dichloromethane:methanol:triethylamine=80:10:1) to give 2-guanidino-5-methyl-4-(4-methylpyridin-2-yl)thiazole (402 mg).

$^1$H-NMR (DMSO-$d_6$): δ2.35(3H,s), 2.62(3H,s), 6.81(4H, broad s), 7.06(1H,d,J=5.0 Hz), 7.69(1H,s), 8.42(1H,d,J=5.0 Hz)

Preparation 25

To a suspension of 2-bromo-3-methylpyridine (1.72 g), 3-nitrophenylboronic acid (2.17 g) and tetrakis (triphenylphosphine)-palladium (577 mg) in 1,2-dimethoxyethane (20 ml) was added 2M aqueous solution of sodium carbonate (13 ml). The mixture was stirred at 80° C. for 5 hours under a nitrogen atmosphere, then cooled to room temperature and diluted with dichloromethane. The organic layer was separated, washed with water and brine and dried over sodium sulfate. The solvent was evaporated under reduced pressure. The residue was purified by column chromatography (silica gel 75g, dichloromethane:n-hexane= 67:33 to 100:0) to give 3-(3-methylpyridin-2-yl)-nitrobenzene (1.81 g).

$^1$H-NMR (CDCl$_3$): δ2.40(3H,s), 7.2–7.4(1H,m), 7.6–7.8 (2H,m), 7.90(1H,d,J=7.7 Hz), 8.26(1H,d,J=7.7 Hz), 8.43 (1H,s), 8.57(1H,d,J=4.0 Hz)

Preparation 26

A suspension of 3-(3-methylpyridin-2-yl)nitrobenzene (214 mg) in ethanol (5 ml) was hydrogenated over palladium on carbon (10% w/w, 50% wet, 50 mg) under a hydrogen atmosphere for 2 hours. The catalyst was filtered off, and the filtrate was evaporated under reduced pressure to give 3-(3-methylpyridin-2-yl)aniline (184 mg).

$^1$H-NMR (CDCl$_3$): δ2.37 (3H,s), 6.73(1H,d,J=6.8 Hz), 6.8–7.0(2H,m), 7.1–7.3(4H,m), 7.62(1H,d,J=7.0 Hz), 8.52 (1H,d,J=4.8 Hz)

EXAMPLE 39

To a suspension of $^3$-(3-methylpyridin-2-yl)aniline (184 mg), N,N'-bis(tert-butoxycarbonyl)thiourea (331 mg) and diisopropylethyl-amine (0.4 ml) in dichloromethane (10 ml) was added 1-methyl-2-chloropyridinium iodide (332 mg), and the mixture was stirred for 3 hours. The mixture was diluted with dichloromethane, washed with water and brine, dried over magnesium sulfate and evaporated under reduced pressure. The residue was purified by column chromatography (silica gel 30 g, n-hexane:ethyl acetate=2:1) to give N,N'-bis(tert-butoxycarbonyl)-N"-(3-(3-methylpyridin-2-yl)phenyl)guanidine (327 mg).

$^1$H-NMR (CDCl$_3$): δ1.50(18H,s), 2.45(3H,s), 7.2–7.5 (4H,m), 7.5–7.7(2H,m), 7.80(1H,s), 8.53(1H,d,J=3.6 Hz), 10.39(1H,s), 11.59(1H,s)

EXAMPLE 40

To a solution of N,N'-bis(tert-butoxycarbonyl)-N"-(3-(3-methylpyridin-2-yl)phenyl)guanidine (213 mg) in dichloromethane (2 ml) was added a solution of hydrogen chloride in 1,4-dioxane (4N, 4 ml), and the mixture was stirred at room temperature for 8 hours. The solvent was evaporated under reduced pressure. To the residue was added 5% ethanol in ethyl acetate (100 ml), and the precipitate was collected by filtration and dried under reduced pressure to give 3-(3-methylpyridin-2-yl)phenylguanidine dihydrochloride (119 mg).

$^1$H-NMR (DMSO-$d_6$): δ2.44(3H,s), 7.42(1H,d,J=7.2 Hz), 7.5–8.8(8H,m), 8.35(1H,d,J=7.6 Hz), 8.71(1H,d,J=5.2 Hz), 10.38(1H,s)

Preparation 27

To a suspension of 2-chloro-3-trifluoromethylpyridine (908 mg), 3-nitrophenylboronic acid (1.09 g) and tetrakis (triphenylphosphine)-palladium (289 mg) in 1,2-dimethoxyethane (20 ml) was added 2M aqueous solution of sodium carbonate (6.5 ml). The mixture was stirred at 80° C. for 7 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 50 g, ethyl acetate:n-hexane= 20:80 to 25:75) to give 3-(3-trifluoromethylpyridin-2-yl)-nitrobenzene (677 mg).

$^1$H-NMR (CDCl$_3$): δ7.4–7.6(1H,m), 7.65(1H,t,J=7.9 Hz), 7.86(1H,d,J=7.7 Hz), 8.15(1H,d,J=8.1 Hz), 8.34(1H,d,J=8.1 Hz), 8.42(1H,s), 8.89(1H,d,J=3.9 Hz)

Preparation 28

A suspension of 3-(3-trifluoromethylpyridin-2-yl) nitrobenzene (500 mg) in ethanol (10 ml) was hydrogenated over palladium on carbon (10% w/w, 50% wet, 167 mg) under a hydrogen atmosphere for 2 hours. The catalyst was filtered off, and the filtrate was evaporated under reduced pressure to give 3-(3-trifluoromethylpyridin-2-yl)aniline (425 mg).

$^1$H-NMR (CDCl$_3$): δ3.73(2H,broad s), 6.7–6.9(2H,m), 7.1–7.3(4H,m), 7.3–7.5(1H,m), 8.06(1H,dd,J=8.1 Hz,1.3 Hz), 8.81(1H,d,J=4.8 Hz)

EXAMPLE 41

To a suspension of 3-(3-trifluoromethylpyridin-2-yl) aniline (200 mg), N,N'-bis(tert-butoxycarbonyl)thiourea (278 mg) and diisopropylethylamine (0.336 ml) in dichloromethane (10 ml) was added 1-methyl-2-chloropyridinium iodide (279 mg), and the mixture was stirred for 16 hours. The mixture was diluted with ethyl acetate, washed with water and brine, dried over magnesium sulfate and evaporated under reduced pressure. The residue was purified by column chromatography (silica gel 30 g, n-hexane:ethyl acetate=4:1) to give N,N'-bis(tert-butoxycarbonyl)-N"-(3-(3-trifluoromethylpyridin-2-yl)phenyl)guanidine (234 mg).

$^1$H-NMR (CDCl$_3$): δ1.50(9H,s), 1.52(9H,s), 7.2–7.3(1H, m), 7.4–7.6(2H,m),7.60(1H,s), 7.98(1H,d,J=9.5 Hz), 8.08 (1H,d,J=8.0 Hz), 8.83(1H,d,J=3.8 Hz), 10.45(1H,s), 11.61 (1H,s)

EXAMPLE 42

To a solution of N,N'-bis(tert-butoxycarbonyl)-N"-(3-(3-trifluoromethylpyridin-2-yl)phenyl)guanidine (200 mg) in dichloromethane (2 ml) was added 4N hydrogen chloride in 1,4-dioxane (4 ml), and the mixture was stirred at room temperature for 18 hours. The solvent was evaporated under reduced pressure. To the residue was added 5% ethanol in ethyl acetate (100 ml), and the precipitate was collected by filtration and dried under reduced pressure to give 3-(3-trifluoromethylpyridin-2-yl) phenylguanidine dihydrochloride (111 mg).

$^1$H-NMR (DMSO-$d_6$): δ7.2–7.8(9H,m), 8.35(1H,d,J=6.8 Hz), 8.91(1H,d,J=4.0 Hz), 10.16(1H,s)

Preparation 29

To a suspension of 2-chloro-3-nitropyridine (792 mg), 3-aminophenylboronic acid (1.01 g) and tetrakis (triphenylphosphine)-palladium (289 mg) in 1,2- dimethoxyethane (20 ml) was added 2M aqueous solution of sodium carbonate (6.5 ml). The mixture was stirred at 80° C. for 7 hours under a nitrogen atmosphere, then cooled to room temperature and diluted with ethyl acetate. The organic layer was separated, washed with water and brine and dried over sodium sulfate. The solvent was evaporated under reduced pressure. Methanol was added to the residue. The precipitate was collected by filtration and dried under reduced pressure to give 3-(3-nitropyridin-2-yl)-aniline (445 mg).

$^1$H-NMR (CDCl$_3$): δ3.79(2H,broad s), 6.7–7.0(3H,m), 7.21(1H,d,J=8.0 Hz), 7.42(1H,dd,J=8.0 Hz,4.7 Hz), 8.10 (1H,dd,J=8.1 Hz,1.6 Hz), 8.83(1H,dd,J=4.8 Hz,1.5 Hz)

EXAMPLE 43

To a suspension of 3-(3-nitropyridin-2-yl)aniline (400 mg), N,N'-bis(tert-butoxycarbonyl)thiourea (616 mg) and diisopropylethylamine (0.745 ml) in dichloromethane (18.6 ml) was added 1-methyl-2-chloropyridinium iodide (618 mg), and the mixture was stirred for 16 hours. The mixture was diluted with ethyl acetate, washed with water and brine, dried over magnesium sulfate and evaporated under reduced pressure. The residue was purified by column chromatography (silica gel 30 g, n-hexane:ethyl acetate=4:1) to give N,N'-bis(tert-butoxycarbonyl)-N"-(3-(3-nitropyridin-2-yl) phenyl)guanidine (730 mg).

$^1$H-NMR (CDCl$_3$): δ1.52(18H,s), 7.2–7.4(1H,m), 7.5–7.7 (2H,m), 7.78(1H,s), 7.92(1H,d,J=8.0 Hz), 8.14(1H,dd,J=8.2 Hz,1.6 Hz), 8.85(1H,dd,J=4.7 Hz,1.6 Hz), 10.48(1H,s), 11.61(1H,s)

EXAMPLE 44

To a solution of N,N'-bis(tert-butoxycarbonyl)-N"-(3-(3-nitropyridin-2-yl)phenyl)guanidine (200 mg) in dichloromethane (2 ml) was added 4N hydrogen chloride in 1,4-dioxane (2 ml), and the mixture was stirred at room temperature for 16 hours. The solvent was evaporated under reduced pressure. To the residue was added 5% ethanol in ethyl acetate (100 ml), and the precipitate was collected by filtration and dried under reduced pressure to give 3-(3-nitropyridin-2-yl)phenylguanidine dihydrochloride (127 mg).

$^1$H-NMR (DMSO-d$_6$): δ7.3–7.8(9H,m), 8.50(1H,dd,J= 8.2 Hz, 1.5 Hz), 8.95(1H,dd,J=6.7 Hz, 1.5 Hz), 10.20(1H,s)

EXAMPLE 45

A suspension of N,N'-bis(tert-butoxycarbonyl)-N"-(3-(3-nitropyridin-2-yl)phenyl)guanidine (520 mg) in ethanol (15 ml) was hydrogenated over palladium on carbon (10% w/w, 50% wet, 500 mg) under a hydrogen atmosphere for 24 hours. The catalyst was filtered off, and the filtrate was evaporated under reduced pressure. The residue was triturated with ethanol, filtered, and dried to give N,N'-bis(tert-butoxycarbonyl)-N"-(3-(3-aminopyridin-2-yl)phenyl) guanidine (325 mg).

$^1$H-NMR (CDCl$_3$): δ1.49(9H,s), 1.54(9H,s), 7.0–7.2(2H, m), 7.4–7.6(3H,m), 7.91(1H,s), 8.13(1H,dd,J=3.4 Hz,J=2.7 Hz), 10.38(1H,s), 11.60(1H,s)

EXAMPLE 46

To a solution of N,N'-bis(tert-butoxycarbonyl)-N"-(3-(3-aminopyridin-2-yl)phenyl)guanidine (150 mg) in dichloromethane (1.5 ml) was added 4N hydrogen chloride in 1,4-dioxane (3 ml), and the mixture was stirred at room temperature for 26 hours. The solvent was evaporated under reduced pressure. To the residue was added 5% ethanol in ethyl acetate (100 ml), and the precipitate was collected by filtration and dried under reduced pressure to give 3-(3-aminopyridin-2-yl)phenylguanidine dihydrochloride (92 mg).

$^1$H-NMR (DMSO-d$_6$): δ6.2–6.6(2H,broad s), 7.40(1H,d, J=8.1 Hz), 7.5–7.9(9H,m), 8.04(1H,d,J=4.0 Hz), 10.39(1H, s)

EXAMPLE 47

To a suspension of 2-bromo-4-nitropyridine (406 mg), 3-aminophenylboronic acid (403 mg) and tetrakis (triphenylphosphine)-palladium (116 mg) in 1,2-dimethoxyethane (10 ml) was added 2M aqueous solution of sodium carbonate (2.6 ml). The mixture was stirred at 80° C. for 7 hours under a nitrogen atmosphere, then cooled to room temperature and diluted with ethyl acetate. The organic layer was separated, washed with water and brine and dried over sodium sulfate. The solvent was evaporated under reduced pressure to give crude 3-(4-nitropyridin-2-yl) aniline. This compound was used for next step without purification. To a suspension of 3-(4-nitropyridin-2-yl)-aniline obtained above, N,N'-bis(tert-butoxycarbonyl) thiourea (663 mg) and diisopropylethylamine (0.801 ml) in dichloromethane (20 ml) was added 1-methyl-2-chloropyridinium iodide (664 mg), and the mixture was stirred for 18 hours. The mixture was diluted with ethyl acetate, washed with water and brine, dried over magnesium sulfate and evaporated under reduced pressure. To the residue was added 2-propanol (10 ml), and the precipitate was collected by filtration, washed with 2-propanol and dried to give N,N'-bis(tert-butoxycarbonyl)-N"-(3-(4-nitropyridin-2-yl)phenyl)guanidine (469 mg).

$^1$H-NMR (CDCl$_3$): δ1.51(9H,s), 1.55(9H,s), 7.49(1H,t,J= 8.0 Hz), 7.79(1H,d,J=9.3 Hz), 7.87(1H,d,J=9.3 Hz), 7.95 (1H,dd,J=5.3 Hz,J=2.0Hz), 8.45(1H,d,J=8.0 Hz), 8.96(1H, d,J=5.3 Hz), 10.57(1H,s), 11.68(1H,s)

EXAMPLE 48

A suspension of N,N'-bis(tert-butoxycarbonyl)-N"-(3-(4-nitropyridin-2-yl)phenyl)guanidine (200 mg) in ethanol (10 ml) was hydrogenated over palladium on carbon (10% w/w, 50% wet, 70 mg) under a hydrogen atmosphere for 6 hours. The catalyst was filtered off, and the filtrate was evaporated under reduced pressure. The residue was dissolved in dichloromethane (2 ml). To the solution was added 4N hydrogen chloride in 1,4-dioxane (2 ml), and the mixture was stirred at room temperature for 18 hours. The solvent was evaporated under reduced pressure. To the residue was added 5% ethanol in ethyl acetate (100 ml), and the precipitate was collected by filtration and dried under reduced pressure to give 3-(4-aminopyridin-2-yl)-phenylguanidine dihydrochloride (112 mg).

$^1$H-NMR (DMSO-d$_6$): δ6.87(1H,dd,J=6.9 Hz, J=2.2 Hz), 7.12(1H,d,J=2.2 Hz), 7.45(1H,d,J=6.9 Hz), 7.6–8.0(7H,m), 8.15(1H,d,J=6.9 Hz), 8.26(2H,broad s), 10.48(1H,broad s), 13.98(1H,broad s)

Preparation 30

To a suspension of 2-bromo-4-methoxypyridine (483 mg), 3-nitrophenylboronic acid (643 mg) and tetrakis (triphenylphosphine)-palladium (148 mg) in 1,2-dimethoxyethane (10 ml) was added 2M aqueous solution of sodium carbonate (2.78 ml). The mixture was stirred at 90° C. for 6 hours under a nitrogen atmosphere, then cooled to room temperature and diluted with dichloromethane. The organic layer was separated, washed with water and brine and dried over sodium sulfate. The solvent was evaporated under reduced pressure. The residue was purified by column chromatography (silica gel 40 g, 50–100% dichloromethane in n-hexane) to give 3-(4-methoxypyridin-2-yl)-nitrobenzene (365 mg).

$^1$H-NMR (CDCl$_3$): δ3.95(3H,s), 6.87(1H,dd,J=5.7 Hz,2.4 Hz), 7.31(1H,d,J=2.4 Hz), 7.64(1H,t,J=8.0 Hz), 8.2–8.4(2H, m), 8.56(1H,d,J=5.7 Hz), 8.82(1H,s)

Preparation 31

A suspension of 3-(4-methoxypyridin-2-yl)nitrobenzene (1.8 g) in ethanol (40 ml) was hydrogenated over palladium on carbon (10% w/w, 50% wet, 800 mg) under a hydrogen atmosphere for 5 hours. The catalyst was filtered off, and the filtrate was evaporated under reduced pressure to give 3-(4-methoxypyridin-2-yl)aniline (1.57 g).

$^1$H-NMR (CDCl$_3$): δ2.0–3.0(2H,broad), 3.92(3H,s), 6.7–6.9(2H,m), 7.2–7.4(3H,m), 7.37(1H,d,J=1.7 Hz), 8.51 (1H,d,J=5.8 Hz)

EXAMPLE 49

To a suspension of 3-(4-methoxypyridin-2-yl)aniline (130 mg), N,N'-bis(tert-butoxycarbonyl)thiourea (216 mg) and diisopropylethyl-amine (0.26 ml) in dichloromethane (6.5 ml) was added 1-methyl-2-chloropyridinium iodide (216 mg), and the mixture was stirred for 2 hours. The mixture was diluted with dichloromethane, washed with water and brine, dried over magnesium sulfate and evaporated under reduced pressure. The residue was purified by column chromatography (silica gel 25 g, n-hexane:ethyl acetate= 4:1) to give N,N'-bis (tert-butoxycarbonyl) -N"- (3- (4-methoxypyridin-2-yl) phenyl) guanidine (240 mg).

$^1$H-NMR (CDCl$_3$): δ1.51(9H,s), 1.54(9H,s), 3.92(3H,s), 6.78(1H,dd,J=5.7 Hz,2.4 Hz), 7.2–7.3(1H,m), 7,44(1H,t,J= 7.9 Hz), 7.73(1H,d,J=8.0 Hz), 7.84(1H,d,J=8.0 Hz), 8.12 (1H,s), 8.51(1H,d,J=5.7 Hz), 10.46(1H,s), 11.65(1H,s)

EXAMPLE 50

To a solution of N,N'-bis(tert-butoxycarbonyl)-N"-(3-(4-methoxypyridin-2-yl)phenyl)guanidine (200 mg) in dichloromethane (2 ml) was added a solution of hydrogen chloride in 1,4-dioxane (4N, 4 ml), and the mixture was stirred at room temperature for 24 hours. The solvent was evaporated under reduced pressure. To the residue was added 5% ethanol in ethyl acetate (100 ml), and the precipitate was collected by filtration and dried under reduced pressure to give 3-(4-methoxypyridin-2-yl)phenylguanidine dihydrochloride (120 mg).

$^1$H-NMR (DMSO-d$_6$): δ4.10(3H,s), 7.3–7.5(2H,m), 7.6–7.8(5H,m), 7.80(1H,d,J=2.4 Hz), 7.9–8.1(2H,m), 8.68 (1H,d,J=6.5 Hz), 10.33(1H,s)

Preparation 32

To a suspension of 3-(3-cyanopyridin-2-yl)aniline (195 mg), N,N'-bis(tert-butoxycarbonyl)thiourea (332 mg) and diisopropylethylamine (0.401 ml) in dichloromethane (10 ml) was added 1-methyl-2-choropyridinium iodide (332 mg), and the mixture was stirred for 18 hours. The mixture was diluted with dichloromethane, washed with water and brine, dried over magnesium sulfate and evaporated under reduced pressure. The residue was crystallized from methanol. The precipitate was collected by filtration, washed with methanol and dried to give N,N'-bis(tert-butoxycaronyl)-N"-(3-(3-cyanopyridin-2-yl)phenyl)guanidine (383 mg). The solvent was evaporated under reduced pressure. The residue was purified by column chromatography (silica gel 75 g, dichloromethane) to give 3-( 4-methylpyridin-2-yl) nitrobenzene (1.4 g).

$^1$H-NMR (CDCl$_3$): δ2.46(3H,s), 7.16(1H,dd,J=5.0 Hz,0.8 Hz), 7.6–7.8(2H,m), 8.26(1H,d,J=8.0 Hz), 8.38(1H,d,J=8.0 Hz), 8.59(1H,d,J=5.0 Hz), 8.85(1H,s)

Preparation 33

A suspension of 3-(4-methylpyridin-2-yl)nitrobenzene (100 mg) in ethanol (2 ml) was hydrogenated over palladium on carbon (10% w/w, 50% wet, 10 mg) under a hydrogen atmosphere for 3 hours. The catalyst was filtered off, and the filtrate was evaporated under reduced pressure to give 3-(4-methylpyridin-2-yl)aniline (85 mg).

$^1$H-NMR (CDCl$_3$): δ2.40(3H,s), 3.54(2H,broad s), 6.7–6.8 (1H,m), 7.04(1H,d,J=5.0 Hz), 7.2–7.5(3H,m), 7.51(1H,d,J= 0.7 Hz), 8.52(1H,d,J=5.0 Hz)

EXAMPLE 51

To a suspension of 3-(4-methylpyridin-2-yl)aniline (276 mg), N,N'-bis (tert-butoxycarbonyl )thiourea (539 mg) and diisopropylethyl-amine (0.601 ml) in dichloromethane (15 ml) was added 1-methyl-2-chloropyridinium iodide (498 mg), and the mixture was stirred for 2.5 hours. The mixture was diluted with dichloromethane, washed with water and brine, dried over magnesium sulfate and evaporated under reduced pressure. The residue was purified by column chromatography (silica gel 45 g, n-hexane:ethyl acetate= 9:1) to give N,N'-bis(tert-butoxycarbonyl) -N"-(3-(4-methylpyridin-2-yl)phenyl)guanidine (397 mg).

$^1$H-NMR (CDCl$_3$): δ1.52(9H,s), 1.54(9H,s), 2.43(3H,s), 7.08(1H,d,J=4.2 Hz), 7.44(1H,t,J=8.0 Hz), 7.59(1H,s), 7.7–7.9(2H,m), 8.18(1H,s), 8.55(1H,d,J=5.0 Hz), 10.46(1H, s), 11.63(1H,s)

EXAMPLE 52

To a solution of N,N'-bis(tert-butoxycarbonyl)-N"-(3-(4-methylpyridin-2-yl)phenyl)guanidine (300 mg) in dichloromethane (3 ml) was added a solution of hydrogen chloride in 1,4-dioxane (4N, 6 ml), and the mixture was stirred at room temperature for 18 hours. The solvent was evaporated under reduced pressure. To the residue was added 5% ethanol in ethyl acetate (100 ml), and the precipitate was collected by filtration and dried under reduced pressure to give (3-(4-methylpyridin-2-yl)phenyl)guanidine dihydrochloride (119 mg).

$^1$H-NMR (DMSO-d$_6$): δ2.59(3H,s), 7.44(1H,d,J=8.1 Hz), 7.6–8.0(6H,m), 8.0–8.2(2H,m), 8.21(1H,s), 8.72(1H,d,J=5.7 Hz), 10.48(1H,s)

Preparation 34

To a suspension of methyl 2-chloronicotinate (1.89 g), 3-nitrophenylboronic acid (1.67 g) and tetrakis (triphenylphosphine)-palladium (578 mg) in 1,2-dimethoxyethane (20 ml) was added 2M aqueous solution of sodium carbonate (11 ml). The mixture was stirred at 80° C. for 3 hours under a nitrogen atmosphere, then cooled to room temperature and diluted with ethyl acetate. The organic layer was separated, washed with water and brine and dried over sodium sulfate. The solvent was evaporated under reduced pressure. The residue was triturated with 2-propanol, filtered, washed with 2-propanol and dried under reduced pressure to give 3-(3-methoxycarbonylpyridin-2-yl)-nitrobenzene (713 mg).

$^1$H-NMR (CDCl$_3$): δ3.76(3H,s), 7.47(1H,dd,J=8.0 Hz,2.4 Hz), 7.62(1H,J=8.0 Hz), 7.87(1H,dt,J=8.0 Hz,1.4 Hz), 8.2–8.4(2H,m), 8.43(1H,t,J=1.9 Hz), 8.83(1H,dd,J=4.8 Hz,1.7 Hz)

EXAMPLE 53

A suspension of 3-(3-methoxycarbonylpyridin-2-yl) nitrobenzene (0.7 g) in methanol (7 ml) and tetrahydrofuran (7 ml) was hydrogenated over palladium on carbon (10% w/w, 50% wet, 0.28 g) under a hydrogen atmosphere for 3 hours. The catalyst was filtered off, and the filtrate was evaporated under reduced pressure. The residue was dissolved in dichloromethane (25 ml). To the solution were added N,N'-bis(tert-butoxycarbonyl)thiourea (0.9 g), 1-methyl-2-chloropyridinium iodide (0.9 g) and diisopropylethylamine (1.09 ml), and the mixture was stirred at ambient temperature for 12 hours.

To a suspension of 2-2-chloro-3-formylpyridine (0.708 g), 3-nitrophenylboronic acid (1.09 g) and tetrakis(triphenyphosphine)palladium (289 mg) in 1,2-dimethoxyethane (20 ml) was added 2M aqueous solution of sodium carbonate (6.5 ml). The mixture was stirred at 80° C. for 14 hours under a nitrogen atmosphere, then cooled to room temperate and diluted with ethyl acetate. The organic layer was separated, washed with water and brine and dried over sodium sulfate. The solvent was evaporated under reduced pressure. The residue was purified by column chromatography (silica gel 50 g, n-hexane:ethyl acetate= 1:1) to give 3-(3-formylpyrdin-2-)nitrobenzene (1.07 g).

EXAMPLE 54

To a solution of N,N'-bis(tert-butoxycarbonyl)-N"-(3-(3-methoxycarbonylpyridin-2-yl)phenyl)guanidine (203 mg) in dichloromethane (2 ml) was added a solution of hydrogen chloride in 1,4-dioxane (4N, 4 ml), and the mixture was stirred at room temperature for 16 hours. The solvent was evaporated under reduced pressure. To the residue was added 5% ethanol in ethyl acetate (100 ml), and the precipitate was collected by filtration and dried under reduced pressure to give 3-(3-methoxycarbonylpyridin-2-yl)phenyl-guanidine dihydrochloride (142 mg).

$^1$H-NMR (DMSO-d$_6$): δ3.72(3H,s), 7.2–7.8(9H,m), 8.21 (1H,dd,J=7.8 Hz,1.7 Hz), 8.84(1H,dd,J=4.8 Hz,1.7 Hz), 10.25(1H,s)

EXAMPLE 55

To a solution of N,N'-bis(tert-butoxycarbonyl)-N"-(3-(3-methoxycarbonylpyridin-2-yl)phenyl)guanidine (282 mg) in methanol (3 ml) was added an aqueous sodium hydroxide solution (1N, 1.2 ml), and the mixture was stirred for 2 hours. The pH of the reaction mixture was adjusted to 5 with 1N hydrochloric acid. The mixture was diluted with water and extracted with ethyl acetate. The separated organic layer was washed with brine, dried over magnesium sulfate and evaporated under reduced pressure. The residue was triturated with diisopropyl ether, filtered and dried to give N,N'-bis(tert-butoxycarbonyl)-N"-(3-(3-carboxypyridin-2-yl)phenyl)guanidine (0.23 g).

$^1$H-NMR (DMSO-d$_6$): δ1.41(18H,s), 7.2–7.6(6H,m), 8.08(1H,dd,J=7.8 Hz,1.7 Hz), 8.73(1H,dd,J=4.7 Hz,1.7 Hz)

EXAMPLE 56

To a solution of N,N-bis(tert-butoxycarbonyl)-N"-(3-(3-carboxypyridin-2-yl)phenyl)guanidine (220 mg) in dichloromethane (2 ml) was added a solution of hydrogen chloride in 1,4-dioxane (4N, 4 ml), and the mixture was stirred at room temperature for 16 hours. The solvent was evaporated under reduced pressure. To the residue was added 5% ethanol in ethyl acetate (100 ml), and the precipitate was collected by filtration and dried under reduced pressure to give 3-(3-carboxypyridin-2-yl)phenylguanidine dihydrochloride (144 mg).

$^1$H-NMR (DMSO-d$_6$): δ3.72(3H,s), 7.3–7.8(10H,m), 8.23(1H,dd,J=7.8 Hz,1.7 Hz), 8.80(1H,dd,J=4.8 Hz,1.7 Hz), 10.23(1H,s)

Preparation 35

To a suspension of 2-bromo-4-nitropyridine (1.0 g) in ethanol (5 ml) was added a solution of sodium ethoxide in ethanol (20%, 2 ml), and the resultant mixture was stirred at 85° C. for 1.5 hours. After cooling, the mixture was diluted with dichloromethane and washed with water and brine. The separated organic layer was dried over sodium sulfate and evaporated under reduced pressure to give 2-bromo-4-ethoxypyridine (927 mg).

$^1$H-NMR (CDCl$_3$): δ1.43(3H,t,J=7.0 Hz), 4.08(2H,q,J=7.0 Hz), 6.76(1H,dd,J=5.8 Hz,2.3 Hz), 6.98(1H,d,J=2.3 Hz), 8.15(1H,d,J=5.8 Hz)

Preparation 36

To a suspension of 2-bromo-4-ethoxypyridine (879 mg), 3-nitrophenylboronic acid (944 mg) and tetrakis(triphenylphosphine)-palladium (251 mg) in 1,2-dimethoxyethane (20 ml) was added 2M aqueous solution of sodium carbonate (5.66 ml). The mixture was stirred at 90° C. for 8 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 40 g, 25% ethyl acetate in n-hexane) to give 3-(4-ethoxypyridin-2-yl)nitrobenzene (887 mg).

$^1$H-NMR (CDCl$_3$): δ1.49(3H,t,J=7.0 Hz), 4.18(2H,q,J=7.0 Hz), 6.83(1H,dd,J=5.7 Hz,2.4 Hz), 7.29(1H,d,J=2.4 Hz), 7.63(1H,t,J=8.0 Hz), 8.2–8.4(2H,m), 8.54(1H,d,J=5.7 Hz), 8.81(1H,t,J=2.0 Hz)

Preparation 37

A suspension of 3-(4-ethoxypyridin-2-yl)nitrobenzene (0.3 g) in ethanol (6 ml) was hydrogenated over palladium on carbon (10% w/w, 50% wet, 0.2 g) under a hydrogen atmosphere for 3 hours. The catalyst was filtered off, and the filtrate was evaporated under reduced pressure to give 3-(4-ethoxypyridin-2-yl)aniline (0.264 g).

$^1$H-NMR (CDCl$_3$): δ1.46(3H,t,J=7.0 Hz), 3.0–3.6(2H, broad), 4.14(2H,q,J=7.0 Hz), 6.7–6.9(2H,m), 7.2–7.4(4H, m), 8.48(1H,d,J=5.7 Hz)

EXAMPLE 57

To a suspension of 3-(4-ethoxypyridin-2-yl)aniline (258 mg), N,N'-bis(tert-butoxycarbonyl)thiourea (399 mg) and diisopropylethyl-amine (0.482 ml) in dichloromethane (12 ml) was added 1-methyl-2-chloropyridinium iodide (400 mg), and the mixture was stirred for 2 hours. The mixture was diluted with ethyl acetate, washed with water and brine, dried over magnesium sulfate and evaporated under reduced pressure. The residue was purified by column chromatography (silica gel 25 g, n-hexane:ethyl acetate=3:1) to give N,N'-bis(tert-butoxycarbonyl) -N"-(3-(4-ethoxypyridin-2-yl)phenyl)guanidine (389 mg).

$^1$H-NMR (CDCl$_3$): δ1.46(3H,t,J=7.0 Hz), 1.51(9H,s), 1.54(9H,s), 4.16(2H,q,J=7.0 Hz), 6.75(1H,dd,J=5.7 Hz,2.4 Hz), 7.2–7.3(1H,m), 7.43(1H,t,J=7.9 Hz), 7.72(1H,d,J=8.0 Hz), 7.84(1H,d,J=8.0 Hz), 8.11(1H,t,J=1.8 Hz), 8.49(1H,d, J=5.7 Hz), 10.46(1H,s), 11.64(1H,s)

EXAMPLE 58

To a solution of N,N'-bis (tert-butoxycarbonyl)-N"-(3-(4-ethoxypyridin-2-yl)phenyl)guanidine (200 mg) in dichloromethane (2 ml) was added a solution of hydrogen chloride in 1,4-dioxane (4N, 4 ml), and the mixture was stirred at room temperature for 16 hours. The solvent was evaporated under reduced pressure. To the residue was added 10% ethanol in ethyl acetate (50 ml), and the precipitate was collected by filtration and dried under reduced pressure to give 3-(4-ethoxypyridin-2-yl)phenylguanidine dihydrochloride (126 mg).

$^1$H-NMR (DMSO-d$_6$): δ1.43(3H,t,J=7.0 Hz), 4.45(2H,q J=7.0 Hz), 7.3–8.0(10H,m), 8.68(1H,d,J=6.7 Hz), 10.45(1H, s)

Preparation 38

To a suspension of 2-bromo-3-methoxypyridine (1.54 g), 3-nitrophenylboronic acid (1.77 g) and tetrakis(triphenylphosphine)-palladium (473 mg) in 1,2-dimethoxyethane (30 ml) was added 2M aqueous solution of sodium carbonate (10.6 ml). The mixture was stirred at 80° C. for 15 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 40 g, 25% ethyl acetate in n-hexane) to give 3-($^3$-methoxypyridin-2-yl)nitrobenzene (1.7 g).

$^1$H-NMR (CDCl$_3$): δ3.93(3H,s), 7.3–7.4(2H,m), 7.61 (1H,t,J=8.0 Hz), 8.2–8.4(3H,m), 8.87(1H,t,J=2.0 Hz)

Preparation 39

A suspension of 3-(3-methoxypyridin-2-yl)nitrobenzene (0.391 g) in ethanol (8 ml) was hydrogenated over palladium on carbon (10% w/w, 50% wet, 120 mg) under a hydrogen atmosphere for 3 hours. The catalyst was filtered off, and the filtrate was evaporated under reduced pressure to give 3-(3-methoxypyridin-2-yl)aniline (0.34 g).

$^1$H-NMR (CDCl$_3$): δ2.7–3.1 (2H,broad), 3.96(3H,s), 6.8–7.0(1H,m), 7.2–7.4(5H,m), 8.30(1H,dd,J=4.4 Hz,1.7 Hz)

EXAMPLE 59

To a suspension of 3-(3-methoxypyridin-2-yl)aniline (0.34 g), N,N'-bis(tert-butoxycarbonyl)thiourea (563 mg) and diisopropylethyl-amine (0.681 ml) in dichloromethane (15 ml) was added 1-methyl-2-chloropyridinium iodide (565 mg), and the mixture was stirred for 18 hours. The mixture was diluted with dichloromethane, washed with water and brine, dried over magnesium sulfate and evaporated under reduced pressure. The residue was crystallized from methanol. The precipitate was collected by filtration, washed with methanol and dried to give N,N'-bis(tert-butoxycarbonyl)-N"-(3-(3-methoxypyridin-2-yl)phenyl)guanidine (512 mg).

$^1$H-NMR (CDCl$_3$): δ1.50(9H,s), 1.53(9H,s), 3.89(3H,s), 7.2–7.4(2H,m), 7.41(1H,t,J=7.9 Hz), 7.70(1H,d,J=8.0 Hz), 7.80(1H,d,J=8.0 Hz), 8.01(1H,t,J=1.8 Hz), 8.51(1H,dd,J= 4.3 Hz,1.7 Hz), 10.40(1H,s), 11.67(1H,s)

EXAMPLE 60

To a solution of N,N'-bis(tert-butoxycarbonyl)-N"-(3-(3-methoxypyridin-2-yl)phenyl)guanidine (200 mg) in dichloromethane (2 ml) was added a solution of hydrogen chloride in 1,4-dioxane (4N, 4 ml), and the mixture was stirred at room temperature for 18 hours. The solvent was evaporated under reduced pressure. To the residue was added 5% ethanol in ethyl acetate (100 ml), and the precipitate was collected by filtration and dried under reduced pressure to give 3-(3-methoxypyridin-2-yl)phenylguanidine dihydrochloride (135 mg).

$^1$H-NMR (DMSO-d$_6$): δ3.94(3H,s), 7.35(1H,d,J=9.0 Hz), 7.5–7.9(8H,m), 7.96(1H,d,J=8.4 Hz), 8.39(1H,d,J=4.0 Hz), 10.30(1H,s)

Preparation 40

To a suspension of 2-chloro-3-cyanopyridine (0.693 g), 3-nitrophenylboronic acid (1.09 g) and tetrakis(triphenylphosphine)-palladium (289 mg) in 1,2-dimethoxyethane (20 ml) was added 2M aqueous solution of sodium carbonate (6.5 ml). The mixture was stirred at 80° C. for 24 hours under a nitrogen atmosphere, then cooled to room temperature and diluted with ethyl acetate. The organic layer was separated, washed with water and brine and dried over sodium sulfate. The solvent was evaporated under reduced pressure. The residue was crystallized from 2-propanol. The precipitate was collected by filtration, washed with diisopropyl ether and dried to give 3-(3-cyanopyridin-2-yl)nitrobenzene (294 mg).

$^1$H-NMR (CDCl$_3$) : δ7.50(1H,dd,J=8.0 Hz,4.9 Hz), 7.74 (1H,t,J=8.0 Hz), 8.15(1H,dd,J=7.9 Hz,1.8 Hz), 8.2–8.5(2H, m), 8.83(1H,t,J=2.0 Hz), 8.94(1H,dd,J=4.9 Hz,1.8 Hz)

Preparation 41

A suspension of 3-(3-cyanopyridin-2-yl)nitrobenzene (0.27 g) in ethanol (5 ml) was hydrogenated over palladium on carbon (10% w/w, 50% wet, 80 mg) under a hydrogen atmosphere for 5 hours. The catalyst was filtered off, and the filtrate was evaporated under reduced pressure to give 3-(3-cyanopyridin-2-yl)aniline (0.34 g).

$^1$H-NMR (CDCl$_3$): δ3.4–4.2(2H,broad), 6.7–6.9(1H,m), 7.2–7.4(4H,m), 8.06(1H,dd,J=7.9 Hz,1.8 Hz), 8.85(1H,dd, J=4.8 Hz,1.8 Hz)

EXAMPLE 61

To a suspension of 3-(3-cyanopyridin-2-yl)aniline (195 mg), N,N'-bis(tert-butoxycarbonyl)thiourea (332 mg) and diisopropylethylamine (0.401 ml) in dichloromethane (10 ml) was added 1-methyl-2-chloropyridinium iodide (332 mg), and the mixture was stirred for 18 hours. The mixture was diluted with dichloromethane, washed with water and brine, dried over magnesium sulfate and evaporated under reduced pressure. The residue was crystallized from methanol. The precipitate was collected by filtration, washed with methanol and dried to give N,N'-bis(tert-butoxycarbonyl)-N"-(3-(3-cyanopyridin-2-yl)phenyl)guanidine (383 mg).

$^1$H-NMR (CDCl$_3$): δ1.49(9H,s), 1.54(9H,s), 3.89(3H,s), 7.39(1H,dd,J=7.9 Hz,4.9 Hz), 7.51(1H,t,J=7.9 Hz), 7.72(1H, d,J=7.9 Hz), 7.9–8.0(2H,m), 8.08(1H,dd,J=7.9 Hz,1.7 Hz), 8.87(1H,dd,J=4.9 Hz,1.7 Hz), 10.4–10.8(1H,broad s), 11.70 (1H,s)

EXAMPLE 62

To a solution of N,N'-bis(tert-butoxycarbonyl)-N"-(3-(3-cyanopyridin-2-yl)phenyl)guanidine (200 mg) in dichloromethane (2 ml) was added a solution of hydrogen chloride in 1,4-dioxane (4N, 4 ml), and the mixture was stirred at room temperature for 18 hours. The solvent was evaporated under reduced pressure. To the residue was added 5% ethanol in ethyl acetate (20 ml), and the precipitate was collected by filtration and dried under reduced pressure to give 3-(3-cyanopyridin-2-yl)phenylguanidine dihydrochloride (90 mg).

$^1$H-NMR (DMSO-d$_6$): δ7.44(1H,d,J=8.4 Hz), 7.5–7.8 (7H,m), 7.81(1H,d,J=8.0 Hz), 8.47(1H,dd,J=8.0 Hz,1.7 Hz), 8.96(1H,dd,J=4.8 Hz,1.7 Hz), 10.18(1H,s)

Preparation 42

A solution of 3-(3-methoxypyridin-2-yl)nitrobenzene (0.5 g) in 47% hydrobromic acid (10 ml) was stirred at 130° C. for 24 hours. After cooling, the precipitate was collected by filtration, washed with water and acetone and dried to give 3-(3-hydroxypyridin-2-yl)-nitrobenzene hydrobromide (0.54 g).

¹H-NMR (DMSO-d₆): δ7.50(1H,dd,J=8.4 Hz,4.7 Hz), 7.64(1H,dd,J=8.4 Hz,1.4 Hz), 7.80(1H,t,J=8.1 Hz), 8.2–8.4 (2H,m), 8.48(1H,dt,J=7.8 Hz,1.4 Hz), 8.87(1H,t,J=1.9 Hz), 11.10(1H,broad s)

Preparation 43

To a stirred suspension of 3-(3-hydroxypyridin-2-yl) nitrobenzene hydrobromide (0.3 g) and imidazole (165 mg) in N,N-dimethylformamide (3 ml) was added tert-butyldimethylsilyl chloride (183 mg), and the mixture was stirred for 18 hours. The mixture was diluted with ethyl acetate and washed with a saturated aqueous sodium hydrogencarbonate solution and brine. The separated organic layer was dried over sodium sulfate and evaporated under reduced pressure to give 3-(3-tert-butyldimethylsilyloxypyridin-2-yl)nitrobenzene (332 mg).

¹H-NMR (DMSO-d₆): δ0.09(6H,s), 0.88(9H,s), 7.2–7.4 (2H,m), 7.60(1H,t,J=8.0 Hz), 8.2–8.4(1H,m), 8.37(1H,dd,J= 4.2 Hz,2.4 Hz), 8.81 (1H,t,J=2.0 Hz)

Preparation 44

A suspension of 3-(3-tert-butyldimethylsilyloxypyridin-2-yl)-nitrobenzene (332 mg) in ethanol (5 ml) was hydrogenated over palladium on carbon (10% w/w, 50% wet, 150 mg) under a hydrogen atmosphere for 4 hours. The catalyst was filtered off, and the filtrate was evaporated under reduced pressure to give 3-(3-tert-butyldimethylsilyloxypyridin-2-yl)aniline (303 mg).

¹H-NMR (CDCl₃): δ0.00(6H,s), 0.89(9H,s), 3.4–4.0(2H, broad s), 6.6–6.8(1H,m), 7.1–7.3(5H,m), 8.31(1H,dd,J=4.4 Hz,1.6 Hz)

EXAMPLE 63

To a suspension of 3-(3-tert-butyldimethylsilyloxypyridin-2-yl)-aniline (303 mg), N,N'-bis(tert-butoxycarbonyl)thiourea (335 mg) and diisopropylethylamine (0.405 ml) in dichloromethane (10 ml) was added 1-methyl-2-chloropyridinium iodide (335 mg), and the mixture was stirred for 18 hours. The mixture was diluted with ethyl acetate, washed with water and brine, dried over magnesium sulfate and evaporated under reduced pressure. The residue was purified by column chromatography (silica gel, 35 g, 20% ethyl acetate in n-hexane) to give N,N'-bis(tert-butoxycarbonyl)-N"-(3-(3-tert-butyldimethylsilyloxypyridin-2-yl)phenyl)guanidine (486 mg).

¹H-NMR (CDCl₃): δ0.03(6H,s), 0.89(9H,s), 1.51(9H,s), 1.53(9H,s), 7.1–7.3(2H,m), 7.40(1H,t,J=8.0 Hz), 7.63(1H,d, J=8.0 Hz), 7.77(1H,s), 8.11(1H,d,J=8.1 Hz), 8.32(1H,dd,J= 4.4 Hz,1.6 Hz), 10.49(1H,s), 11 .63(1H,s)

EXAMPLE 64

To a solution of N,N'-bis(tert-butoxycarbonyl)-N"-(3-(3-tert-butyldimethylsilyloxypyridine-2-yl)phenyl)guanidine (300 mg) in dichloromethane (3 ml) was added a solution of hydrogen chloride in 1,4-dioxane (4N, 6 ml), and the mixture was stirred at room temperature for 18 hours. The solvent was evaporated under reduced pressure. To the residue was added 5% ethanol in ethyl acetate (100 ml), and the precipitate was collected by filtration and dried under reduced pressure to give 3-(3-hydroxypyridin-2-yl) phenylguanidine dihydrochloride (145 mg).

¹H-NMR (DMSO-d₆): δ7.38(1H,d,J=8.0 Hz), 7.5–7.9 (8H,m), 8.04(1H,d,J=8.4 Hz), 8.34(1H,d,J=4.2 Hz), 10.33 (1H,s), 11.91(1H,broad s)

Preparation 45

To a suspension of 2-chloro-3-formylpyridine (0.708 g), 3-nitrophenylboronic acid (1.09 g) and tetrakis (triphenylphosphine)-palladium (289 mg) in 1,2-dimethoxyethane (20 ml) was added 2M aqueous solution of sodium carbonate (6.5 ml). The mixture was stirred at 80° C. for 14 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 50 g, h-hexane:ethyl acetate= 1:1) to give 3-(3-formylpyrdin-2-yl)nitrobenzene (1.07 g).

¹H-NMR (CDCl₃): δ7.56(1H,dd,J=7.9 Hz,6.5 Hz), 7.73 (1H,t,J=7.9 Hz), 7.91(1H,dd,J=2.8 Hz,1.4 Hz), 8.3–8.5(2H, m), 8.54(1H,t,J=1.9 Hz), 8.94(1H,dd,J=6.5 Hz,1.8 Hz), 10.08(1H, s)

Preparation 46

To a suspension of 3-(3-formylpyridin-2-yl)nitrobenzene (0.6 g) in ethanol (20 ml) was added sodium borohydride (40 mg), and the mixture was stirred for 5 minutes. The mixture was diluted with dichloromethane and washed with water. The separated aqueous layer was extracted with dichloromethane. The combined organic extract was washed with brine, dried over magnesium sulfate and evaporated under reduced pressure to give 3-(3-hydroxymethylpyridin-2-yl) nitrobenzene (606 mg).

¹H-NMR (CDCl₃): δ4.52(2H,d,J=5.3 Hz), 5.52(1H,t,J= 5.3 Hz), 7.50(1H,dd,J=7.7 Hz,4.7 Hz), 7.78(1H,t,J=8.0 Hz), 8.01(1H,dd,J=7.8 Hz,1.7 Hz), 8.12(1H,dt,J=8. Hz,1.3 Hz), 8.3–8.4(1H,m), 8.50(1H,t,J=1.9 Hz), 8.63(1H,dd,J=6.7 Hz,1.7 Hz)

Preparation 47

To a stirred suspension of 3-(3-hydroxymethylpyridin-2-yl)-nitrobenzene hydrobromide (0.3 g) and imidazole (106 mg) in N,N-dimethylformamide (3 ml) was added tert-butyldimethylsilyl chloride (216 mg), and the mixture was stirred for 18 hours. The mixture was diluted with ethyl acetate and washed with a saturated aqueous sodium hydrogencarbonate solution and brine. The separated organic layer was dried over sodium sulfate and evaporated under reduced pressure to give 3-($^3$-tert-butyldimethylsilyloxymethylpyridin-2-yl)nitrobenzene (438 mg).

¹H-NMR (DMSO-d₆): δ0.06(6H,s), 0.90(9H,s), 4.66(2H, m), 7.38(1H,dd,J=7.8 Hz,4.8 Hz), 7.64(1H,t,J=8.0 Hz), 7.9–8.3(3H,m), 8.51(1H,t,J=1.9 Hz), 8.64(1H,dd,J=4.7 Hz,1.6 Hz)

Preparation 48

A suspension of 3-(3-tert-butyldimethylsilyloxymethylpyridin-2-yl)nitrobenzene (0.4 g) in ethanol (10 ml) was hydrogenated over palladium on carbon (10% w/w, 50% wet, 150 mg) under a hydrogen atmosphere for 2 hours. The catalyst was filtered off, and the filtrate was evaporated under reduced pressure to give 3-(3-tert-butyldimethylsilyloxymethylpyridin-2-yl)aniline (365 mg).

¹H-NMR (CDCl₃): δ0.03(6H,s), 0.86(9H,s), 3.68(2H, broad s), 4.64(2H,s), 6.69(1H,dd,J=7.9 Hz,2.3 Hz), 6.7–6.9 (2H,m), 7.1–7.3(2H,m), 7.88(1H,d,J=7.8 Hz), 8.51(1H,d,J= 3.1 Hz)

EXAMPLE 65

To a suspension of 3-(3-tert-butyldimethylsilyloxymethylpyridin-2-yl)aniline (364 mg), N,N'-bis(tert-butoxycarbonyl)thiourea (385 mg) and diisopropylethylamine (0.465 ml) in dichloromethane (12 ml) was added 1-methyl-2-chloropyridinium iodide (385 mg), and the mixture was stirred for 18 hours. The mixture was diluted with ethyl acetate, washed with water and brine, dried over magnesium sulfate and evaporated under reduced pressure. The residue was purified by column chromatography (silica gel 35 g, 20% ethyl acetate in n-hexane) to give N,N'-bis(tert-butoxycarbonyl)-N"-(3-(3-tert-butyldimethylsilyloxymethylpyridin-2-yl)phenyl)guanidine (549 mg).

$^1$H-NMR (CDCl$_3$): δ0.06(6H,s), 0.90(9H,s), 1.50(9H,s), 1.52(9H,s), 4.70(2H,s), 7.2–7.3(2H,m), 7.43(1H,t,J=7.9 Hz), 7.59(1H,s), 7.9–8.1(2H,m), 8.58(1H,dd,J=4.7 Hz,1.7 Hz), 10.46(1H,s), 11.63(1H,s)

EXAMPLE 66

To a solution of N,N'-bis(tert-butoxycarbonyl)-N"-(3-(3-tert-butyldimethylsilyloxymethylpyridin-2-yl)phenyl)guanidine (300 mg) in dichloromethane (3 ml) was added a solution of hydrogen chloride in 1,4-dioxane (4N, 6 ml), and the mixture was stirred at room temperature for 24 hours. The solvent was evaporated under reduced pressure. To the residue was added 5% ethanol in ethyl acetate (100 ml), and the precipitate was collected by filtration and dried under reduced pressure to give 3-(3-hydroxymethylpyridin-2-yl)-phenylguanidine dihydrochloride (1I40 mg).

$^1$H-NMR (DMSO-d$_6$): δ4.58(2H,s), 7.44(1H,d,J=7.0 Hz), 7.5–7.9(8H,m), 7.95(1H,dd,J=8.0 Hz,5.4 Hz), 8.04(1H,d,J=7.7 Hz), 8.34(1H,d,J=4.1 Hz), 10.45(1H,s)

Preparation 49

A suspension of 2-fluoro-4-methylpyridine (1.11 g), 3-nitrophenol (1.67 g) and potassium carbonate (1.80 g) in N,N-dimethylformamide (10 ml) was stirred at 130° C. for 24 hours. After cooling, the mixture was poured into water and stirred for 30 minutes. The precipitate was collected by filtration and dried to give 3-(4-methylpyridin-2-yloxy)-nitrobenzene (935 mg).

$^1$H-NMR (CDCl$_3$): δ2.36(3H,s), 7.01(1H,s), 7.05(1H,d,J=5.1 Hz), 7.6–7.8(2H,m), 7.94(1H,t,J=2.2 Hz), 8.0–8.2(2H,m)

Preparation 50

A suspension of 3-(4-methylpyridin-2-yloxy) nitrobenzene (0.5 g) in ethanol (5 ml) was hydrogenated over palladium on carbon (10% w/w, 50% wet, 100 mg) under a hydrogen atmosphere for 4 hours. The catalyst was filtered off, and the filtrate was evaporated under reduced pressure to give 3-(4-methylpyridin-2-yloxy)aniline (429 mg).

$^1$H-NMR (CDCl$_3$): δ2.32(3H,s), 3.4–4.0(2H,broad), 6.4–6.6(3H,m), 6.68(1H,s), 6.81(1H,d,J=5.1 Hz), 7.15(1H,t,J=8.0 Hz), 8.08(1H,d,J=5.1 Hz)

EXAMPLE 67

To a suspension of 3-(4-methylpyridin-2-yloxy)aniline (264 mg), N,N'-bis(tert-butoxycarbonyl)thiourea (474 mg) and diisopropylethyl-amine (0.529 ml) in dichloromethane (13.2 ml) was added 1-methyl-2-chloropyridinium iodide (438 mg), and the mixture was stirred for 16 hours. The mixture was diluted with dichloromethane, washed with water and brine, dried over magnesium sulfate and evaporated under reduced pressure. The residue was purified by column chromatography (silica gel 25 g, n-hexane:ethyl acetate 4:1) to give N,N'-bis(tert-butoxycarbonyl)-N"-(3-(4-methylpyridin-2-yloxy)phenyl)-guanidine (452 mg).

$^1$H-NMR (CDCl$_3$): δ1.50(18H,s), 2.34(3H,s), 6.69(1H,s), 6.8–6.9(2H,m), 7.2–7.5(2H,m), 7.48(1H,d,J=8.1 Hz), 8.07 (1H,d,J=5.1 Hz), 10.36(1H,s), 11.61(1H,s)

EXAMPLE 68

To a solution of N,N'-bis(tert-butoxycarbonyl)-N"-(3-(4-methylpyridin-2-yloxy)phenyl)guanidine (0.2 g) in dichloromethane (2 ml) and ethanol (2 ml) was added a solution of hydrogen chloride in 1,4-dioxane (4N, 4 ml), and the mixture was stirred at room temperature for 7 hours. The solvent was evaporated under reduced pressure. To the residue was added 20% ethanol in ethyl acetate (20 ml), and the resultant precipitate was collected by filtration and dried under reduced pressure to give (3-(4-methylpyridin-2-yloxy)-phenyl)guanidine dihydrochloride (125 mg).

$^1$H-NMR (DMSO-d$_6$): δ2.34(3H,s), 6.91(1H,s), 7.0–7.2 (4H,m), 7.45(1H,t,J=8.0 Hz), 7.49(4H,s), 8.04(1H,d,J=5.1 Hz), 10.17(1H,s)

EXAMPLE 69

A suspension of 3-(4-methoxypyridin-2-yl)aniline (0.2 g) and thiophene-2-carboximidothioic acid methyl ester hydroiodide (285 mg) in 2-propanol (1 ml) was refluxed for 1 hour. After cooling, the resultant mixture was poured into a saturated aqueous sodium hydrogencarbonate solution and extracted with dichloromethane. The organic layer was washed with brine, dried over sodium sulfate and evaporated under reduced pressure. The residue was dissolved in ethyl acetate (3 ml) and 2-propanol (3 ml). To the solution was added a solution of hydrogen chloride in 1,4-dioxane (4N, 1 ml). The precipitate was collected by filtration, washed with ethyl acetate and dried to give N-(3-(4-methoxypyridin-2-yl)phenyl)thiophene-2-carboxamidine dihydrochloride (344 mg).

$^1$H-NMR (DMSO-d$_6$): δ4.11(3H,s), 7.3–7.5(2H,m), 7.7–7.9(3H,m), 8.1–8.3(3H,m), 8.72(1H,d,J=6.6 Hz), 9.26 (1H,s), 10.08(1H,s), 11.93(1H,s)

Preparation 51

To a suspension of 2-bromo-4-methoxypyridine (1.88 g), 2-methylphenylboronic acid (1.77 g) and tetrakis (triphenylphosphine)-palladium (578 mg) in 1,2-dimethoxyethane (30 ml) was added 2M aqueous solution of sodium carbonate (13 ml). The mixture was stirred at 80° C. for 7 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 50 g, 25% ethyl acetate in n-hexane) to give 2-(4-methoxypyridin-2-yl)toluene (1.98 g).

$^1$H-NMR (CDCl$_3$): δ2.36(3H,s), 3.91(3H,s), 6.79(1H,dd, J=5.8 Hz,2.5 Hz), 6.91(1H,d,J=1.3 Hz), 7.2–7.5(4H,m), 8.50(1H,d,J=5.8 Hz)

Preparation 52

To a suspension of 2-(4-methoxypyridin-2-yl)toluene (0.5 g) in sulfuric acid (4 ml) was added fuming nitric acid (0.176 ml) dropwise at 5° C., and the mixture was stirred at 5° C. for 90 minutes. The reaction mixture was poured into an aqueous sodium hydroxide solution (4N) and extracted with ethyl acetate. The separated organic layer was washed with water and brine, dried over sodium sulfate and evaporated under reduced pressure. The residue was purified by column chromatography (silica gel 30 g, 25% ethyl acetate in n-hexane) to give 2,4-dinitro-6-(4-methoxypyridin-2-yl) toluene (138 mg) and 2-(4-methoxypyridin-2-yl)-4-nitrotoluene (302 mg). 2-(4-Methoxypyridin-2-yl)-4-nitrotoluene.

$^1$H-NMR (CDCl$_3$): δ2.46(3H,s), 3.92(3H,s), 6.8–7.0(2H, s), 7.43(1H,d,J=8.4 Hz), 8.15(1H,dd,J=8.4 Hz,2.5 Hz), 8.26 (1H,d,J=2.5 Hz), 8.54(1H,d,J=6.0 Hz) 2,4-Dinitro-6-(4-methoxypyridin-2-yl)toluene $^1$H-NMR (CDCl$_3$): δ2.53(3H,s), 3.94(3H,s), 6.8–7.0(2H, s), 8.45(1H,d,J=2.4 Hz), 8.57(1H,dd,J=5.3 Hz, 1.0 Hz), 8.70(1H,d,J=2.4 Hz)

Preparation 53

A suspension of 2-(4-methoxypyridin-2-yl)-4-nitrotoluene (293 mg) in tetrahydrofuran (3 ml) and ethanol (3 ml) was hydrogenated over palladium on carbon (10% w/w, 50% wet, 0.1 g) under a hydrogen atmosphere for 3 hours. The catalyst was filtered off, and the filtrate was evaporated under reduced pressure to give 3-(4-methoxypyridin-2-yl)-4-methylaniline (256 mg).

$^1$H-NMR (CDCl$_3$): δ2.23(3H,s), 2.8–4.0(2H,broad), 3.87 (3H,s), 6.66(1H,dd,J=8.0 Hz,2.5 Hz), 6.7–7.9(3H,m), 7.05 (1H,d,J=8.0 Hz), 8.49(1H,d,J=5.9 Hz)

EXAMPLE 70

To a suspension of 3-(4-methoxypyridin-2-yl)-4-methylaniline (238 mg), N,N'-bis(tert-butoxycarbonyl) thiourea (368 mg) and diisopropylethylamine (0.445 ml) in dichloromethane (10 ml) was added 1-methyl-2-chloropyridinium iodide (369 mg), and the mixture was stirred for 2 hours. The mixture was diluted with dichloromethane, washed with water and brine, dried over magnesium sulfate and evaporated under reduced pressure. The residue was purified by column chromatography (silica gel 25 g, n-hexane:ethyl acetate=3:1) to give N,N'-bis(tert-butoxycarbonyl)-N"-(3-(4-methoxypyridin-2-yl)-4-methylphenyl)guanidine (471 mg).

$^1$H-NMR (CDCl$_3$): δ1.49(9H,s), 1.52(9H,s), 2.32(3H,s), 3.89(3H,s), 6.78(1H,dd,J=5.8 Hz,2.5 Hz), 6.93(1H,d,J=2.4 Hz), 7.2–7.3(1H,m), 7.45(1H,d,J=2.4 Hz), 7.72(1H, dd,J=8.3 Hz), 8.49(1H,d,J=5.8 Hz), 10.31(1H,s), 11.62(1H,s)

EXAMPLE 71

To a solution of N,N'-bis(tert-butoxycarbonyl)-N"-(3-(4-methoxypyridin-2-yl)-4-methylphenyl)guanidine (0.2 g) in dichloromethane (2 ml) was added a solution of hydrogen chloride in 1,4-dioxane (4N, 4 ml), and the mixture was stirred at room temperature for 18 hours. The solvent was evaporated under reduced pressure. To the residue was added 5% ethanol in ethyl acetate (50 ml), and the precipitate was collected by filtration and dried under reduced pressure to give (3-(4-methoxypyridin-2-yl)-4-methylphenyl)-guanidine dihydrochloride (137 mg).

$^1$H-NMR (DMSO-d$_6$): δ2.34(3H,s), 4.11(3H,s), 7.34(1H, dd,J=8.2 Hz,2.4 Hz), 7.4–7.9(8H,m), 8.77(1H,d,J=6.8 Hz), 10.38(1H,s),

Preparation 54

A suspension of 2,4-dinitro-6-(4-methoxypyridin-2-yl) toluene (132 mg) in tetrahydrofuran (2 ml) and ethanol (2 ml) was hydrogenated over palladium on carbon (10% w/w, 50% wet, 50 mg) under a hydrogen atmosphere for 4 hours. The catalyst was filtered off, and the filtrate was evaporated under reduced pressure to give 2,4-diamino-6-(4-methoxypyridin-2-yl)toluene (103 mg).

$^1$H-NMR (CDCl$_3$): δ2.00(3H,s), 2.8–4.0(4H,broad), 3.87 (3H,s), 6.14(1H,d,J=2.3 Hz), 6.21(1H,d,J=2.3 Hz), 6.76(1H, dd,J=5.8 Hz,2.6 Hz), 6.87(1H,d,J=2.6 Hz), 8.47(1H,d,J=5.8 Hz)

EXAMPLE 72

To a suspension of 2,4-diamino-6-(4-methoxypyridin-2-yl)toluene (93 mg), N,N'-bis(tert-butoxycarbonyl)thiourea (269 mg) and diisopropylethylamine (0.329 ml) in dichloromethane (5 ml) was added 1-methyl-2-chloropyridinium iodide (273 mg), and the mixture was stirred for 18 hours. The mixture was diluted with dichloromethane, washed with water and brine, dried over magnesium sulfate and evaporated under reduced pressure. The residue was purified by column chromatography (silica gel 25 g, n-hexane:ethyl acetate=3:1) to give 2,4-bis (N,N'-bis (tert-butoxycarbonyl) guanidino)-6-(4-methoxypyridin-2-yl)toluene (177 mg).

$^1$H-NMR (CDCl$_3$): δ1.4–1.6(36H,s), 2.32(3H,s), 2.22 (3H,s), 3.89(3H,s), 6.79(1H,dd,J=5.8 Hz,2.5 Hz), 6.94(1H, d,J=2.4 Hz), 7.63(1H,d,J=2.2 Hz), 8.04(1H,d,J=2.2 Hz), 8.48(1H,d,J=5.8 Hz), 10.15(1H,s), 10.36(1H,s), 11.59(1H, s), 11.63(1H,s)

EXAMPLE 73

To a solution of 2,4-bis(N,N'-bis(tert-butoxycarbonyl) guanidino)-6-(4-methoxypyridin-2-yl)toluene (0.15 g) in dichloromethane (3 ml) was added a solution of hydrogen chloride in 1,4-dioxane (4N, 3 ml), and the mixture was stirred at room temperature for 24 hours. The solvent was evaporated under reduced pressure. To the residue was added 5% ethanol in ethyl acetate (50 ml), and the precipitate was collected by filtration and dried under reduced pressure to give 2,4-diguanidino-6-(4-methoxypyridin-2-yl) toluene trihydrochloride (85 mg).

$^1$H-NMR (DMSO-d$_6$): δ2.19(3H,s), 4.09(3H,s), 7.38(1H, s), 7.5–7.9(11H,m), 8.76(1H,d,J=6.3 Hz), 10.15(1H,s), 10.31(1H,s)

Preparation 55

To a suspension of 2-bromo-4-methoxypyridine (1.21 g), 4-chlorophenylboronic acid (1.21 g) and tetrakis (triphenylphosphine)-palladium (372 mg) in 1,2-dimethoxyethane (20 ml) was added 2M aqueous solution of sodium carbonate (7.74 ml). The mixture was stirred at 80° C. for 12 hours under a nitrogen atmosphere, then cooled to room temperature and diluted with ethyl acetate. The organic layer was separated, washed with water and brine and dried over sodium sulfate. The solvent was evaporated under reduced pressure. 2-Propanol was added to the residue. The precipitate was collected by filtration and dried under reduced pressure to give 4-(4-methoxypyridin-2-yl)-chlorobenzene (1.03 g).

$^1$H-NMR (CDCl$_3$): δ3.91(3H,s), 6.78(1H,dd,J=5.7 Hz,2.4 Hz), 7.19(1H,d,J=2.4 Hz), 7.42(2H,d,J=8.6 Hz), 7.90(2H,d, J=8.0 Hz), 8.51(1H,d,J=5.7 Hz)

Preparation 56

To a suspension of 4-(4-methoxypyridin-2-yl) chlorobenzene (500 mg) in sulfuric acid (4 ml) was added fuming nitric acid (0.2 ml) dropwise at 0° C., and the mixture was stirred at 5° C. for 30 minutes. The reaction mixture was poured into a saturated aqueous sodium hydrogencarbonate solution and extracted with ethyl acetate. The separated organic layer was washed with water and brine, dried over sodium sulfate and evaporated under reduced pressure. The residue was triturated with diisopropyl ether, filtered, washed with diisopropyl ether and dried under reduced pressure to give 1-chloro-4-(4-methoxypyridin-2-yl)-2-nitrobenzene (601 mg).

$^1$H-NMR (CDCl$_3$): δ3.94(3H,s), 6.86(1H,dd,J=5.8 Hz,2.4 Hz), 7.25(1H,d,J=2.4 Hz), 7.64(1H,d,J=8.5 Hz), 8.16(1H, dd,J=6.5 Hz,3.7 Hz), 8.4–8.6(2H,m)

Preparation 57

To a suspension of 1-chloro-4-(4-methoxypyridin-2-yl)-2-nitrobenzene (200 mg) in ethanol (6 ml) and water (0.6 ml) were added iron powder (206 mg) and ammonium chloride (28 mg), and the mixture was refluxed for 3 hours. The mixture was filtered, and the filtrate was evaporated under reduced pressure. To the residue were added ethyl acetate and water. The separated organic layer was washed with brine, dried over magnesium sulfate and evaporated under reduced pressure to give 2-chloro-5-(4-methoxypyridin-2-yl)aniline (174 mg).

¹H-NMR (CDCl₃): δ3.90(3H,s), 4.0–4.3(2H,broad s), 6.77(1H,dd,J=5.7 Hz,2.4 Hz), 7.2–7.4(2H,m), 7.46(1H,d,J=2.0 Hz), 8.49(1H,d,J=5.7 Hz)

EXAMPLE 74

To a suspension of 2-chloro-5-(4-methoxypyridin-2-yl) aniline (165 mg), N,N'-bis(tert-butoxycarbonyl)thiourea (233 mg) and diisopropylethylamine (0.28 ml) in dichloromethane (7 ml) was added 1-methyl-2-chloropyridinium iodide (232 mg), and the mixture was stirred for 16 hours. The mixture was diluted with dichloromethane, washed with water and brine, dried over magnesium sulfate and evaporated under reduced pressure. The residue was purified by column chromatography (silica gel 30 g, n-hexane:ethyl acetate=2:1) to give N,N'-bis(tert-butoxycarbonyl)-N"-(2-chloro-5-(4-methoxypyridin-2-yl)phenyl)guanidine (144 mg).

¹H-NMR (CDCl₃): δ1.51(9H,s), 1.56(9H,s), 3.92(3H,s), 6.78(1H,dd,J=5.7 Hz,2.4 Hz), 7.31(1H,d,J=2.3 Hz), 7.46 (1H,d,J=8.4 Hz), 7.80(1H,dd,J=8.4 Hz,2.1 Hz), 8.48(1H,d, J=5.7 Hz), 9.08(1H,d,J=2.0 Hz), 10.79(1H,s), 11.63(1H,s)

EXAMPLE 75

To a solution of N,N'-bis(tert-butoxycarbonyl)-N"-(2-chloro-5-(4-methoxypyridin-2-yl)phenyl)guanidine (133 mg) in dichloromethane (1 ml) was added a solution of hydrogen chloride in 1,4-dioxane (4N, 3 ml), and the mixture was stirred at room temperature for 24 hours. The solvent was evaporated under reduced pressure. To the residue was added 5% ethanol in ethyl acetate (100 ml), and the resultant precipitate was collected by filtration and dried under reduced pressure to give (2-chloro-5-(4-methoxypyridin-2-yl)phenyl)guanidine dihydrochloride (83 mg).

¹H-NMR (DMSO-d₆): δ4.09(3H,s), 7.38(1H,d,J=6.3 Hz), 7.6–8.0(6H,m), 8.14(1H,d,J=8.3 Hz), 8.22(1H,s), 8.68(1H, d,J=4.8 Hz), 10.10(1H,s)

Preparation 58

To a suspension of 2-bromo-4-methylpyridine (1.60 g), 4-methoxyphenylboronic acid (1.84g) and tetrakis (triphenylphosphine)-palladium (537 mg) in 1,2-dimethoxyethane (40 ml) was added 2M aqueous solution of sodium carbonate (12.1 ml). The mixture was stirred at 80° C. for 24 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 75 g, 20% ethyl acetate in n-hexane) to give 4-(4-methylpyridin-2-yl)anisole (1.59 g).

¹H-NMR (CDCl₃): δ2.41(3H,s), 3.86(3H,s), 7.0–7.2(3H, m), 7.50(1H,d,J=0.7 Hz), 7.95(1H,d,J=8.9 Hz), 8.52(1H,d, J=5.1 Hz)

Preparation 59

To a suspension of 4-(4-methylpyridin-2-yl)anisole (1.38 g) in sulfuric acid (3 ml) was added fuming nitric acid (0.5 ml) dropwise at 0° C., and the mixture was stirred at 5° C. for 1 hour. The reaction mixture was poured into a saturated aqueous sodium hydrogencarbonate solution and extracted with ethyl acetate. The separated organic layer was washed with water and brine, dried over sodium sulfate and evaporated under reduced pressure. The residue was purified by column chromatography (silica gel 100 g, 0–5% methanol in dichloromethane) to give 4-(4-methylpyridin-2-yl)-2-nitroanisole (378 mg).

¹H-NMR (CDCl₃): δ2.43(3H,s), 4.02(3H,s), 7.08(1H,d, J=5.0 Hz), 7.18(1H,d,J=8.8 Hz), 7.53(1H,s), 8.25(1H,dd,J= 8.8 Hz,2.3 Hz), 8.5–8.7(2H,m)

Preparation 60

A suspension of 4-(4-methylpyridin-2-yl)-2-nitro anisole (347 mg) in ethanol (3.5 ml) and tetrahydrofuran (3.5 ml) was hydrogenated over palladium on carbon (10% w/w, 50% wet, 120 mg) under a hydrogen atmosphere for 1 hour. The catalyst was filtered off, and the filtrate was evaporated under reduced pressure to give 2-methoxy-5-(4-methylpyridin-2-yl)aniline (304 mg).

¹H-NMR (CDCl₃): δ2.43(3H,s), 3.90(3H,s), 6.85(1H,d, J=8.4 Hz), 6.98(1H,d,J=5.0 Hz), 7.33(1H,dd,J=8.4 Hz,2.2 Hz), 7.46(1H,d,J=2.2 Hz), 7.47(1H,s), 8.48(1H,d,J=5.0 Hz)

EXAMPLE 76

To a suspension of 2-methoxy-5-(4-methylpyridin-2-yl) aniline (294 mg), N,N'-bis(tert-butoxycarbonyl)thiourea (455 mg) and diisopropylethylamine (0.55 ml) in dichloromethane (15 ml) was added 1-methyl-2-chloropyridinium iodide (455 mg), and the mixture was stirred for 16 hours. The mixture was diluted with ethyl acetate, washed with water and brine, dried over magnesium sulfate and evaporated under reduced pressure. The residue was purified by column chromatography (silica gel 70 g, n-hexane:ethyl acetate=3:1) to give N,N'-bis(tert-butoxycarbonyl)-N"-(2-methoxy-5-(4-methylpyridin-2-yl)phenyl)guanidine (334 mg).

¹H-NMR (CDCl₃): δ1.54(9H,s), 1.55(9H,s), 2.40(3H,s), 3.97(3H,s), 6.9–7.1(2H,m), 7.62(1H,s), 7.88(1H,dd,J=8.6 Hz,2.2 Hz), 8.49(1H,d,J=4.9 Hz), 9.26(1H,d,J=2.2 Hz), 10.75(1H,s), 11.56(1H,s)

EXAMPLE 77

To a solution of N,N'-bis(tert-butoxycarbonyl)-N"-(2-methoxy-5-(4-methylpyridin-2-yl)phenyl)guanidine (200 mg) in dichloromethane (2 ml) was added a solution of hydrogen chloride in 1,4-dioxane (4N, 4 ml), and the mixture was stirred at room temperature for 24 hours. The solvent was evaporated under reduced pressure. To the residue was added 5% ethanol in ethyl acetate (100 ml), and the resultant precipitate was collected by filtration and dried under reduced pressure to give (2-methoxy-5-(4-methylpyridin-2-yl)phenyl)guanidine dihydrochloride (127 mg).

¹H-NMR (DMSO-d₆): δ2.58(3H,s), 3.94(3H,s), 7.39(1H, d,J=8.8 Hz), 7.5–7.7(5H,m), 8.03(1H,s), 8.14(1H,d,J=8.8 Hz), 8.21(1H,s), 8.65(1H,d,J=6.2 Hz), 9.62(1H,s)

Preparation 61

A suspension of 4-(4-methoxypyridin-2-yl)-2-nitrotoluene (300 mg) in tetrahydrofuran (3 ml) and ethanol (3 ml) was hydrogenated over palladium on carbon (10% w/w, 50% wet, 150 mg) under a hydrogen atmosphere for 3 hours. The catalyst was filtered off, and the filtrate was evaporated under reduced pressure to give 5-(4-methoxypyridin-2-yl)-2-methylaniline (254 mg).

¹H-NMR (CDCl₃): δ2.21(3H,s), 3.2–3.8(2H,broad), 3.89 (3H,s), 6.74(1H,dd,J=5.7 Hz,2.4 Hz), 7.1–7.3(3H,m), 7.37 (1H,d,J=1.7 Hz), 8.48(1H,d,J=5.7 Hz)

EXAMPLE 78

To a suspension of 5-(4-methoxypyridin-2-yl)-2-methylaniline (200 mg), N,N'-bis(tert-butoxycarbonyl) thiourea (310 mg) and diisopropyl-ethylamine (0.374 ml) in dichloromethane (10 ml) was added 1-methyl-2-chloropyridinium iodide (310 mg), and the mixture was stirred for 2 hours. The mixture was diluted with dichloromethane, washed with water and brine, dried over magnesium sulfate and evaporated under reduced pressure.

The residue was purified by column chromatography (silica gel 25 g, n-hexane:ethyl acetate=3:1) to give N,N'-bis(tert-butoxycarbonyl)-N"-(5-(4-methoxypyridin-2-yl)-2-methylphenyl)guanidine (357 mg).

$^1$H-NMR (CDCl$_3$): δ1.47(9H,s), 1.54(9H,s), 2.35(3H,s), 3.92(3H,s), 6.76(1H,dd,J=5.8 Hz,2.4 Hz), 7.2–7.3(1H,m), 7.78(1H,dd,J=8.0 Hz,1.9 Hz), 8.49(1H,d,J=5.8 Hz), 8.52 (1H,s), 10.23(1H,s), 11.68(1H,s)

EXAMPLE 79

To a solution of N,N'-bis(tert-butoxycarbonyl)-N"-(5-(4-methoxypyridin-2-yl)-2-methylphenyl)guanidine (200 mg) in dichloromethane (2 ml) was added a solution of hydrogen chloride in 1,4-dioxane (4N, 4 ml), and the mixture was stirred at room temperature for 18 hours. The solvent was evaporated under reduced pressure. To the residue was added 5% ethanol in ethyl acetate (100 ml), and the precipitate was collected by filtration and dried under reduced pressure to give (5-(4-methoxypyridin-2-yl)-2-methylphenyl)-guanidine dihydrochloride (127 mg).

$^1$H-NMR (DMSO-d$_6$): δ2.35(3H,s), 4.12(3H,s), 7.44(1H, dd,J=7.3 Hz,2.5 Hz), 7.5–7.7(5H,m), 7,85(1H,d,J=2.5Hz), 8.0–8.2(2H,m), 8.69(1H,d,J=7.3 Hz), 10.08(1H,s)

Preparation 62

A suspension of 4-(4-methylpyridin-2-yl)-2-nitrotoluene (342 mg) in ethanol (7 ml) was hydrogenated over palladium on carbon (10% w/w, 50% wet, 103 mg) under a hydrogen atmosphere for 3 hours. The catalyst was filtered off, and the filtrate was evaporated under reduced pressure to give 2-methyl-5-(4-methylpyridin-2-yl)aniline (297 mg).

$^1$H-NMR (CDCl$_3$): δ2.21(3H,s), 2.40(3H,s), 3.2–3.6(2H, broad), 7.03(1H,d,J=5.0 Hz), 7.12(1H,d,J=7.8 Hz), 7.2–7.4 (2H,m), 7.39(1H,d,J=1.7 Hz), 7.51(1H,s), 8.51(1H,d,J=5.0 Hz)

EXAMPLE 80

To a suspension of 2-methyl-5-(4-methylpyridin-2-yl) aniline (285 mg), N,N'-bis(tert-butoxycarbonyl)thiourea (475 mg) and diisopropylethylamine (0.577 ml) in dichloromethane (15 ml) was added 1-methyl-2-chloropyridinium iodide (478 mg), and the mixture was stirred for 2 hours. The mixture was diluted with dichloromethane, washed with water and brine, dried over magnesium sulfate and evaporated under reduced pressure. To the residue was added 2-propanol, and the mixture was stirred. The precipitate was collected by filtration and dried to give N,N'-bis(tert-butoxycarbonyl)-N"-(2-methyl-5-(4-methylpyridin-2-yl) phenyl)guanidine (527 mg).

$^1$H-NMR (CDCl$_3$): δ1.50(9H,s), 1.54(9H,s), 2.36(3H,s), 2.44(3H,s), 7.09(1H,d,J=5.0 Hz), 7.29(1H,d,J=8.0 Hz), 7.64 (1H,s), 7.84(1H,dd,J=8.0 Hz,2.0 Hz), 8.55(1H,d,J=5.0 Hz), 8.66(1H,s), 10.26(1H,s), 11.64(1H,s)

EXAMPLE 81

To a solution of N,N'-bis(tert-butoxycarbonyl)-N"-(2-methyl-5-(4-methylpyridin-2-yl)phenyl)guanidine (200 mg) in dichloromethane (2 ml) was added a solution of hydrogen chloride in 1,4-dioxane (4N, 4 ml), and the mixture was stirred at room temperature for 16 hours. The solvent was evaporated under reduced pressure. To the residue were added ethanol (2 ml) and ethyl acetate (10 ml), and the precipitate was collected by filtration and dried under reduced pressure to give (2-methyl-5-(4-methylpyridin-2-yl)phenyl)guanidine dihydrochloride (127 mg).

$^1$H-NMR (DMSO-d$_6$): δ2.35(3H,s), 4.12(3H,s), 7.44(1H, dd,J=7.3 Hz,2.5 Hz), 7.5–7.7(5H,m), 7.85(1H,d,J=2.5 Hz), 8.0–8.2(2H,m), 8.69(1H,d,J=7.3Hz), 10.08(1H,s)

Preparation 63

To a suspension of 2-bromo-4-methoxypyridine (0.94 g), 4-fluorophenylboronic acid (909 mg) and tetrakis (triphenylphosphine)-palladium (289 mg) in 1,2-dimethoxyethane (20 ml) was added 2M aqueous solution of sodium carbonate (6.5 ml). The mixture was stirred at 80° C. for 4 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 50 g, 30% ethyl acetate in n-hexane) to give 4-(4-methoxypyridin-2-yl)fluorobenzene (0.866 g).

$^1$H-NMR (CDCl$_3$): δ3.91(3H,s), 6.7–6.9(1H,m), 7.1–7.2 (2H,m), 7.9–8.1(1H,m), 8.50(1H,d,J=5.7 Hz)

Preparation 64

To a suspension of 4-(4-methoxypyridin-2-yl) fluorobenzene (0.71 g) in sulfuric acid (10 ml) was added fuming nitric acid (0.176 ml) dropwise at 0° C., and the mixture was stirred at 0° C. for 30 minutes. The reaction mixture was poured into an aqueous sodium hydroxide solution (4N) and extracted with ethyl acetate. The separated organic layer was washed with water and brine, dried over sodium sulfate and evaporated under reduced pressure to give 2-fluoro-5-(4-methoxypyridin-2-yl)nitrobenzene (831 mg).

$^1$H-NMR (CDCl$_3$): δ3.94(3H,s), 6.84(1H,dd,J=5.7 Hz,2.4 Hz), 7.24(1H,d,J=2.4 Hz), 7.38(1H,dd,J=10.4 Hz,8.5 Hz), 8.2–8.4(1H,m), 8.53(1H,d,J=5.7 Hz), 8.67(1H,dd,J=7.2 Hz,2.4 Hz)

Preparation 65

A suspension of 2-fluoro-5-(4-methoxypyridin-2-yl) nitrobenzene (0.2 g) in ethanol (4 ml) and tetrahydrofuran (3 ml) was hydrogenated over palladium on carbon (10% w/w, 50% wet, 60 mg) under a hydrogen atmosphere for 5 hours. The catalyst was filtered off, and the filtrate was evaporated under reduced pressure to give 2-fluoro-5-(4-methoxypyridin-2-yl)aniline (176 mg).

$^1$H-NMR (DMSO-d$_6$): δ3.90(3H,s), 5.0–6.0(2H,broad s), 6.94(1H,dd,J=5.8 Hz,2.4 Hz), 7.07(1H,dd,J=11.2 Hz,8.5 Hz), 7.2–7.3(1H,m), 7.34(1H,d,J=2.4 Hz), 7.54(1H,dd,J=9.0 Hz,2.2 Hz), 8.43(1H,d,J=5.8 Hz)

EXAMPLE 82

To a suspension of 2-fluoro-5-(4-methoxypyridin-2-yl) aniline (174 mg), N,N'-bis(tert-butoxycarbonyl)thiourea (265 mg) and diisopropylethylamine (0.417 ml) in dichloromethane (10 ml) was added 1-methyl-2-chloropyridinium iodide (266 mg), and the mixture was stirred for 18 hours. The mixture was diluted with dichloromethane, washed with water and brine, dried over magnesium sulfate and evaporated under reduced pressure. The residue was purified by column chromatography (silica gel 30 g, n-hexane:ethyl acetate=3:1) to give N,N'-bis(tert-butoxycarbonyl)-N"-(2-fluoro-5-(4-methoxypyridin-2-yl)phenyl)guanidine (248 mg).

$^1$H-NMR (CDCl$_3$): δ1.51(9H,s), 1.56(9H,s), 3.92(3H,s), 6.76(1H,dd,J=5.7 Hz,2.4 Hz), 7.18(1H,dd,J=10.5 Hz,8.7 Hz), 7.2–7.4(1H,m), 7.7–7.9(1H,m), 8.48(1H,d,J=5.7 Hz), 9.02(1H,dd,J=7.6 Hz,2.4 Hz), 10.63(1H,s), 11.61(1H,s)

EXAMPLE 83

To a solution of N,N'-bis(tert-butoxycarbonyl)-N"-(2-fluoro-5-(4-methoxypyridin-2-yl)phenyl)guanidine (0.2 g) in dichloromethane (2 ml) was added a solution of hydrogen chloride in 1,4-dioxane (4N, 4 ml), and the mixture was stirred at room temperature for 24 hours. The solvent was evaporated under reduced pressure. To the residue was added 5% ethanol in ethyl acetate (100 ml), and the resultant precipitate was collected by filtration and dried under reduced pressure to give (2-fluoro-5-(4-methoxypyridin-2-yl)phenyl)guanidine dihydrochloride (143 mg).

$^1$H-NMR (DMSO-d$_6$): δ4.12(3H,s), 7.3–8.0(7H,m), 8.1–8.3(2H,m), 8.69(1H,d,J=6.6 Hz), 10.20(1H,s)

Preparation 66

To a stirred solution of ammonium isothiocyanate (142 mg) in acetone (3 ml) was added benzoyl chloride (0.199 ml) at 50° C., and the mixture was stirred at 50° C. for 10 minutes. To the resultant suspension was added a solution of 3-(4-methylpyridin-2-yl)aniline (300 mg) in acetone (6 ml) dropwise, and the mixture was stirred at 60° C. for 2 hours. Water was added to the reaction mixture, and the precipitate was collected by filtration and dried to give N-(3-(4-methylpyridin-2-yl)phenyl)-N'-benzoylthiourea (557 mg).

$^1$H-NMR (DMSO-d$_6$): δ2.41(3H,s), 7.22(1H,d,J=4.9 Hz), 7.5–7.9(6H,m), 7.9–8.1(3H,m), 8.36(1H,s), 8.54(1H,d,J=4.9 Hz), 11.62(1H,s), 12.70(1H,s)

EXAMPLE 84

To a suspension of N-(3-(4-methylpyridin-2-yl)phenyl)-N'-benzoylthiourea (540 mg) in methanol (5 ml) was added an aqueous sodium hydroxide solution (1N, 1.55 ml) dropwise. The mixture was stirred at 60° C. for 1 hour, cooled to ambient temperature, and the pH was adjusted to 8.0 with 1N hydrochloric acid. The mixture was diluted with water (50 ml) and extracted with ethyl acetate. The organic layer was washed with brine, dried over sodium sulfate and evaporated under reduced pressure. The residue was triturated with diisopropyl ether, collected by filtration, washed with diisopropyl ether and dried under reduced pressure to give N-(3-(4-methylpyridin-2-yl)phenyl)thiourea (356 mg).

$^1$H-NMR (DMSO-d$_6$): δ2.39(3H,s), 7.19(1H,d,J=5.0 Hz), 7.3–7.6(4H,m), 7.7–7.9(2H,m), 8.10(1H,d,J=1.7 Hz), 8.51(1H,d,J=5.0 Hz), 9.79(1H,s)

EXAMPLE 85

To a suspension of N-(3-(4-methylpyridin-2-yl)phenyl)thiourea (243 mg) in N,N-dimethylformamide (5 ml) were added a solution of hydrogen chloride in 1,4-dioxane (4N, 0.5 ml) and iodoethane (0.4 ml), and the mixture was stirred at 50° C. for 2 hours. Ethyl acetate (100 ml) was added to the mixture, and the mixture was cooled. The precipitate was collected by filtration and dissolved in water. To the solution was added a saturated aqueous sodium hydrogencarbonate solution, and the mixture was extracted with dichloromethane. The organic layer was washed with brine, dried over sodium sulfate and evaporated under reduced pressure. The residue was dissolved in ethyl acetate, and to the solution was added a solution of hydrogen chloride in 1,4-dioxane (4N, 1 ml). The precipitate was collected by filtration and dried under reduced pressure to give N-(3-(4-methylpyridin-2-yl)phenyl)-S-ethylisothiourea dihydrochloride (294 mg).

$^1$H-NMR (DMSO-d$_6$): δ1.33(3H,t,J=7.3 Hz), 2.59(3H,s), 3.40(2H,q,J=7.3 Hz), 7.57(1H,d,J=8.2 Hz), 7.6–7.8(2H,m), 8.1–8.3(3H,m), 8.72(1H,d,J=5.6 Hz), 9.4–10.0(1H,broad), 12.10(1H,broad s)

Preparation 67

To a suspension of 2-bromo-4-methylpyridine (2.0 g), 4-formylphenylboronic acid (2.27 g) and tetrakis(triphenylphosphine)-palladium (0.67 g) in 1,2-dimethoxyethane (40 ml) was added 2M aqueous solution of sodium carbonate (15.1 ml). The mixture was stirred at 90° C. for 6 hours under a nitrogen atmosphere, then cooled to room temperature and diluted with ethyl acetate. The organic layer was separated, washed with water and brine and dried over sodium sulfate. The solvent was evaporated under reduced pressure. The residue was purified by column chromatography (silica gel 75 g, dichloromethane) to give 4-(4-methylpyridin-2-yl)benzaldehyde (483 mg).

$^1$H-NMR (CDCl$_3$): δ2.45(3H,s), 7.15(1H, dd,J=5.0 Hz,0.8 Hz), 7.63(1H,d,J=0.8 Hz), 7.98(2H,d,J=8.3 Hz), 8.17(2H,d,J=8.3 Hz), 8.60(1H,d,J=5.0 Hz), 10.08(1H,s)

Preparation 68

To a suspension of 4-(4-methylpyridin-2-yl)benzaldehyde (425 mg) in ethanol (5 ml) was added hydroxylamine hydrochloride (224 mg), and the mixture was stirred at 60° C. for 1 hour. After cooling, the mixture was poured into a saturated aqueous sodium hydrogencarbonate solution and extracted with dichloromethane. The organic layer was washed with water and brine, dried over sodium sulfate and evaporated under reduced pressure to give 4-(4-methylpyridin-2-yl)benzaldehyde oxime (0.43 g).

$^1$H-NMR (CDCl$_3$): δ2.43(3H,s), 7.10(1H,d,J=5.0 Hz), 7.65(1H,s), 7.75(2H,d,J=8.0 Hz), 8.09(2H,d,J=8.0 Hz), 8.19(1H,s), 8.2–8.4(1H,broad s), 8.57(1H,d,J=5.0 Hz)

EXAMPLE 86

To a solution of 4-(4-methylpyridin-2-yl)benzaldehyde oxime (0.41 g) in N,N-dimethylformamide (2 ml) were added a solution of hydrogen chloride in 1,4-dioxane (4N, 1.06 ml) and potassium peroxymonosulfate (OXONE, 0.712 g). The reaction mixture was stirred for 1.5 hours, and to the mixture were added tetrahydrofuran (10 ml) and thiourea (0.176 g). Then to the resultant suspension was added a solution of triethylamine (0.673 ml) in tetrahydrofuran (2 ml) dropwise, and the mixture was stirred for 1 hour. The mixture was poured into water (100 ml) and extracted with ethyl acetate (100 ml). The separated aqueous layer was extracted with ethyl acetate (50 ml). The combined organic layer was washed with brine, dried over sodium sulfate and evaporated under reduced pressure. The residue was dissolved in tetrahydrofuran (5 ml), and to the solution was added aqueous ammonia (28%, 3 ml) dropwise. The mixture was diluted with ethyl acetate and washed with water and brine. The organic layer was dried over sodium sulfate and evaporated under reduced pressure. To the residue was added dichloromethane and diisopropyl ether, and the precipitate was collected by filtration and dried to give N-(4-(4-methylpyridin-2-yl)-phenyl)thiourea (206 mg).

$^1$H-NMR (DMSO-d$_6$): δ2.38(3H,s), 7.14(1H,d,J=4.8 Hz), 7.55(2H,d,J=8.4 Hz), 7.4–7.8(2H,broad s), 8.03(2H,d,J=8.4 Hz), 8.49(1H,d,J=4.8 Hz), 9.83(1H,s)

EXAMPLE 87

To a suspension of N-(4-(4-methylpyridin-2-yl)phenyl)thiourea (186 mg) in N,N-dimethylformamide(4 ml) were added a solution of hydrogen chloride in 1,4-dioxane (4N, 0.383 ml) and iodoethane (0.306 ml), and the mixture was stirred at 50° C. for 2.5 hours. After cooling, the mixture was poured into a saturated aqueous sodium hydrogencarbonate solution and extracted with ethyl acetate. The organic layer was washed with brine, dried over sodium sulfate and evaporated under reduced pressure. The residue was dissolved in ethyl acetate, and to the solution was added a solution of hydrogen chloride in 1,4-dioxane (4N, 0.5 ml). The precipitate was collected by filtration and recrystallized from ethanol-ethyl acetate to give N-(4-(4-methylpyridin-2-yl)phenyl)-S-ethylisothiourea dihydrochloride (162 mg).

$^1$H-NMR (DMSO-d$_6$): δ1.32(3H,t,J=7.1 Hz), 2.50(3H,s), 3.35(2H,q,J=7.1 Hz), 7.4–7.6(3H,m), 8.11(1H,s), 8.23(2H,d,J=7.7 Hz), 8.65 (1H,d,J=5.3 Hz), 9.64 (1H,broad s)

Preparation 69

A suspension of 2-methyl-5-(4-methoxypyridin-2-yl)nitrobenzene (0.19 g) in ethanol (2 ml) and tetrahydrofuran (2 ml) was hydrogenated over palladium on carbon (10% w/w, 50% wet, 80 mg) under a hydrogen atmosphere for 2 hours. The catalyst was filtered off, and the filtrate was evaporated under reduced pressure. The residue was dissolved in acetone (5 ml). To the solution was added benzoyl isothiocyanate (0.12 ml), and the mixture was stirred at ambient temperature for 4 hours. To the reaction mixture was added water, and the precipitate was collected by filtration and dried to give N-(5-(4-methoxypyridin-2-yl)-2-methylphenyl)-N'-benzoylthiourea (282 mg).

$^1$H-NMR (DMSO-d$_6$): δ2.34(3H,s), 3.98(3H,s), 7.08(1H,dd,J=6.0 Hz,2.4 Hz), 7.4–7.7(4H,m), 7.9–8.1(3H,m), 8.26 (1H,s), 8.53(1H,d,J=6.0 Hz), 11.71(lH,s), 12.36(1H,s)

EXAMPLE 88

To a suspension of N-(5-(4-methoxypyridin-2-yl)-2-methylphenyl)-N'-benzoylthiourea (0.27 g) in methanol (5 ml) was added an aqueous sodium hydroxide solution (IN, 0.89 ml) dropwise. The mixture was stirred at ambient temperature for 4 hours, and the pH was adjusted to 8.0 with 1N hydrochloric acid. The mixture was diluted with water (50 ml) and extracted with dichloromethane-methanol (4:1) three times. The organic layer was washed with brine, dried over sodium sulfate and evaporated under reduced pressure. The residue was triturated with diisopropyl ether, collected by filtration, washed with diisopropyl ether and dried under reduced pressure to give N-(5-(4-methoxypyridin-2-yl)-2-methylphenyl)thiourea (176 mg).

$^1$H-NMR (DMSO-d$_6$): δ2.23(3H,s), 3.91(3H,s), 6.93(1H,dd,J=5.7 Hz,2.4 Hz), 7.0–7.8(2H,broad), 7.33(1H,d,J=8.0 Hz), 7.44(1H,d,J=2.4 Hz), 7.8–8.0(2H,m), 8.44(1H,d,J=5.7 Hz), 9.31(1H,s)

EXAMPLE 89

To a suspension of N-(5-(4-methoxypyridin-2-yl)-2-methylphenyl)-thiourea (0.15 g) in N,N-dimethylformamide (3 ml) were added a solution of hydrogen chloride in 1,4-dioxane (4N, 0.274 ml) and iodoethane (0.22 ml), and the mixture was stirred at ambient temperature for 5 hours. Ethyl acetate (100 ml) was added to the mixture, and the mixture was cooled. The precipitate was collected by filtration. The precipitate was dissolved in water, and to the solution was added a saturated aqueous sodium hydrogencarbonate solution and extracted with ethyl acetate. The organic layer was washed with brine, dried over sodium sulfate and evaporated under reduced pressure. The residue was dissolved in ethyl acetate, and to the solution was added a solution of hydrogen chloride in 1,4-dioxane (4N, 0.5 ml). The precipitate was collected by filtration and dried under reduced pressure to give N-(5-(4-methoxypyridin-2-yl)-2-methylphenyl)-S-ethylisothiourea dihydrochloride (168 mg).

$^1$H-NMR (DMSO-d$_6$): δ1.34(3H,t,J=7.3 Hz), 2.33(3H,s), 3.38(2H,q,J=7.3 Hz), 4.12(3H,s), 7.43(1H,d,J=6.6 Hz), 7.64 (1H,d,J=7.8 Hz), 7.85(1H,d,J=2.4 Hz), 8.1–8.3(2H,m), 8.68 (1H,d,J=6.6 Hz), 9.0–10.0(2H,broad)

Preparation 70

A suspension of 2-fluoro-5-(4-methoxypyridin-2-yl)nitrobenzene (0.3 g) in ethanol (3 ml) and tetrahydrofuran (3 ml) was hydrogenated over palladium on carbon (10% w/w, 50% wet, 100 mg) under a hydrogen atmosphere for 2 hours. The catalyst was filtered off, and the filtrate was evaporated under reduced pressure. The residue was oh; dissolved in acetone (10 ml). To the solution was added benzoyl isothiocyanate (0.195 ml), and the mixture was stirred at ambient temperature for 18 hours. To the reaction mixture was added water, and the precipitate was collected by filtration and dried to give N-(2-fluoro-5-(4-methoxypyridin-2-yl)phenyl)-N'-benzoylthiourea (350 mg).

$^1$H-NMR (DMSO-d$_6$): δ3.98(3H,s), 6.97(1H,dd,J=5.7 Hz,2.4 Hz), 7.4–7.8(5H,m), 8.0–8.2(3H,m), 8.49(1H,d,J=5.7 Hz), 8.70(1H,d,J=5.4 Hz), 11.85(1H,s), 12.57(1H,s)

EXAMPLE 90

To a suspension of N-(2-fluoro-5-(4-methoxypyridin-2-yl)phenyl)-N'-benzoylthiourea (0.32 g) in methanol (3 ml) was added an aqueous sodium hydroxide solution (1N, 1 ml) dropwise. The mixture was stirred at ambient temperature for 4 hours, and the pH was adjusted to 8.0 with 1N hydrochloric acid. The precipitate was triturated with water, collected by filtration, washed with water and dried under reduced pressure to give N-(2-fluoro-5-(4-methoxypyridin-2-yl)-phenyl)thiourea (216 mg).

$^1$H-NMR (DMSO-d$_6$): δ3.91(3H,s), 6.95 (1H,dd,J=5.7 Hz,2.4 Hz), 7.0–8.0(2H,broad), 7.33(1H,dd,J=10.2 Hz,8.7 Hz), 7.44(1H,d,J=2.3 Hz), 7.8–8.0(1H,m), 8.37(1H,dd,J=5.8 Hz,2.2 Hz), 8.47(1H,d,J=5.7 Hz), 9.46(1H,s)

EXAMPLE 91

To a suspension of N-(2-fluoro-5-(4-methoxypyridin-2-yl)phenyl)-thiourea (0.1 g) in N,N-dimethylformamide (2 ml) were added a solution of hydrogen chloride in 1,4-dioxane (4N, 0.181 ml) and iodoethane (0.144 ml), and the mixture was stirred at 80° C. for 3 hours. Ethyl acetate (100 ml) was added to the mixture, and the mixture was cooled. The precipitate was collected by filtration. The precipitate was dissolved in water, and to the solution was added a saturated aqueous sodium hydrogencarbonate solution and extracted with ethyl acetate. The organic layer was washed with brine, dried over sodium sulfate and evaporated under reduced pressure. The residue was dissolved in ethyl acetate, and to the solution was added a solution of hydrogen chloride in 1,4-dioxane (4N, 1 ml). The precipitate was collected by filtration and dried under reduced pressure to give N-(2-fluoro-5-(4-methoxypyridin-2-yl)phenyl)-S-ethylisothiourea dihydrochloride (125 mg).

$^1$H-NMR (DMSO-d$_6$): δ1.34(3H,t,J=7.3 Hz), 3.36(2H,q,J=7.3 Hz), 4.06(3H,s), 7.3–7.4(1H,m), 7.66(1H,d,J=9.6 Hz), 7.77(1H,d,J=2.4 Hz), 8.1–8.3(2H,m), 8.64 (1H,d,J=6.3 Hz), 9.4–10.0(2H,broad)

Preparation 71

To a suspension of 3-(4-methoxypyridin-2-yl)aniline (357 mg) in acetone (5 ml) was added benzoyl isothiocyanate (0.252 ml), and the mixture was stirred at ambient temperature for 1 hour. To the reaction mixture was added diisopropyl ether, and the precipitate was collected by filtration and dried to give N-(3-(4-methoxypyridin-2-yl)phenyl)-N'-benzoylthiourea (462 mg).

$^1$H-NMR (DMSO-d$_6$): δ3.93(3H,s), 6.98(1H,dd,J=5.7 Hz,2.4 Hz), 6.7–8.1(9H,m), 8.37(1H,s), 8.50(1H,d,J=5.7 Hz), 11.63(1H,s), 12.69(1H,s)

EXAMPLE 92

To a suspension of N-(3-(4-methoxypyridin-2-yl)phenyl)-N'-benzoylthiourea (429 mg) in methanol (5 ml) was added an aqueous sodium hydroxide solution (1N, 1.42 ml) dropwise. The mixture was stirred at 60° C. for 1 hour and cooled to ambient temperature. The pH was adjusted to 8.0 with 1N hydrochloric acid. The mixture was diluted with water (50 ml) and extracted with dichloromethane-methanol (4:1). The organic layer was washed with brine, dried over sodium sulfate and evaporated under reduced pressure. The residue was triturated with diisopropyl ether, collected by filtration, washed with diisopropyl ether and dried under reduced pressure to give N-(3-(4-methoxypyridin-2-yl)phenyl) thiourea (294 mg).

$^1$H-NMR (DMSO-d$_6$): δ3.91(3H,s), 6.96(1H,dd,J=5.7 Hz,2.4 Hz), 7.3–7.7(5H,m), 7.82(1H,d,J=7.6 Hz), 8.10(1H, s), 8.48(1H,d,J=5.7 Hz), 9.79(1H,s)

EXAMPLE 93

To a suspension of N-(3-(4-methoxypyridin-2-yl)phenyl) thiourea (171 mg) in N,N-dimethylformamide (4 ml) were added a solution of hydrogen chloride in 1,4-dioxane (4N, 0.33 ml) and iodoethane (0.263 ml), and the mixture was stirred at 50° C. for 1.5 hours. Ethyl acetate (100 ml) was added to the mixture, and the mixture was cooled. The precipitate was collected by filtration. The precipitate was dissolved in water, and to the solution was added a saturated aqueous sodium hydrogencarbonate solution and extracted with dichloromethane. The organic layer was washed with brine, dried over sodium sulfate and evaporated under reduced pressure. The residue was dissolved in ethyl acetate, and to the solution was added a solution of hydrogen chloride in 1,4-dioxane (4N, 0.5 ml). The precipitate was collected by filtration and dried under reduced pressure to give N-(3-(4-methoxypyridin-2-yl)phenyl)-S-ethylisothiourea dihydrochloride (204 mg).

$^1$H-NMR (DMSO-d$_6$): δ1.33(3H,t,J=7.3 Hz), 3.38(2H,q, J=7.3 Hz), 4.12(3H s), 7.43(1H,dd,J=6.6 Hz,2.4 Hz), 7.58 (1H,d,J=8.0 Hz), 7.74(1H,t,J=8.0 Hz), 7.85(1H,d,J=2.4 Hz), 8.0–8.2(2H,m), 8.71(1H,d,J=6.6 Hz), 9.78(1H,broad s), 11.94(1H,broad s)

EXAMPLE 94

To a suspension of N-(3-(4-methoxypyridin-2-yl)phenyl) thiourea (122 mg) in N,N-dimethylformamide (2.5 ml) were added a solution of hydrogen chloride in 1,4-dioxane (4N, 0.25 ml) and iodomethane (0.156 ml), and the mixture was stirred at ambient temperature for 5 hours. Ethyl acetate (100 ml) was added to the mixture, and the mixture was cooled. The precipitate was collected by filtration. The precipitate was dissolved in water, and to the solution was added a saturated aqueous sodium hydrogencarbonate solution and extracted with dichloromethane. The organic layer was washed with brine, dried over sodium sulfate and evaporated under reduced pressure. The residue was dissolved in ethyl acetate, and to the solution was added a solution of hydrogen chloride in 1,4-dioxane (4N, 0.5 ml). The precipitate was collected by filtration and dried under reduced pressure to give N-(3-(4-methoxypyridin-2-yl)phenyl)-S-methylisothiourea dihydrochloride (153 mg).

$^1$H-NMR (DMSO-d$_6$): δ2.75(3H,s), 4.12(3H,s), 7.43(1H, d,J=6.3 Hz), 7.58(1H,d,J=8.3 Hz), 7.74(1H,t,J=8.2 Hz), 7.84 (1H,d,J=2.4 Hz), 8.0–8.2(2H,m), 8.70(1H,d,J=6.6 Hz), 9.64 (1H,broad s)

EXAMPLE 95

To a suspension of N-(3-(4-methoxypyridin-2-yl)phenyl) thiourea (104 mg) in N,N-dimethylformamide (2 ml) were added a solution of hydrogen chloride in 1,4-dioxane (4N, 0.2 ml) and iodopropane (0.195 ml), and the mixture was stirred at 50° C. for 2 hours. Ethyl acetate (100 ml) was added to the mixture, and the mixture was cooled. The precipitate was collected by filtration. The precipitate was dissolved in water, and to the solution was added a saturated aqueous sodium hydrogencarbonate solution and extracted with dichloromethane. The organic layer was washed with brine, dried over sodium sulfate and evaporated under reduced pressure. The residue was dissolved in ethyl acetate, and to the solution was added a solution of hydrogen chloride in 1,4-dioxane (4N, 0.5 ml). The precipitate was collected by filtration and dried under reduced pressure to give N-(3-(4-methoxypyridin-2-yl)phenyl)-S-propylisothiourea dihydrochloride (143 mg).

$^1$H-NMR (DMSO-d$_6$): δ1.03(3H,t,J=7.1 Hz), 1.6–1.8(2H, m), 3.37(2H,q,J=7.3 Hz), 4.11(3H,s), 7.43(1H,dd,J=6.5 Hz,2.3 Hz), 7.58(1H,d,J=8.4 Hz), 7.73(1H,t,J=8.2 Hz), 7.85 (1H,d,J=2.5 Hz), 8.0–8.2(2H,m), 8.71(1H,d,J=6.6 Hz), 9.4–10.0(2H,broad), 11.95(1H,broad s)

Preparation 72

To a suspension of 2-bromo-4-methoxypyridine (2.5 g), 4-methyl-3-nitrophenylboronic acid (3.37 g) and tetrakis (triphenylphosphine)-palladium (768 mg) in 1,2-dimethoxyethane (100 ml) was added 2M aqueous solution of sodium carbonate (18.6 ml). The mixture was stirred at 80° C. for 7 hours under a nitrogen atmosphere, then cooled to room temperature and diluted with ethyl acetate. The organic layer was separated, washed with water and brine and dried over sodium sulfate. The solvent was evaporated under reduced pressure. Methanol was added to the residue. The precipitate was collected by filtration and dried under reduced pressure to give 4-(4-methoxypyridin-2-yl)-2-nitrotoluene (3.09 g).

$^1$H-NMR (CDCl$_3$): δ2.65(3H,s), 3.93(3H,s), 6.82(1H,dd, J=5.7 Hz,2.4 Hz), 7.25(1H,d,J=2.7 Hz), 7.43(1H,d,J=8.0 Hz), 8.14(1H,dd,J=8.0 Hz,2.0 Hz), 8.53(1H,d,J=5.8 Hz), 8.58(1H,d,J=2.0 Hz)

Preparation 73

To a solution of 4-(4-methoxypyridin-2-yl)-2-nitrotoluene (2.5 g) in N,N-dimethylformamide (15 ml) was added N,N-dimethylformamide dimethyl acetal (2.72 ml), and the mixture was stirred at 140° C. for 24 hours under a nitrogen atmosphere. The reaction mixture was evaporated under reduced pressure, and the residue was suspended in tetrahydrofuran (60 ml) and water (60 ml). Sodium metaperiodate (6.57 g) was added to the suspension, and the mixture was stirred at ambient temperature for 3 hours. The reaction mixture was filtered, and the filtrate was extracted with ethyl acetate. The separated organic layer was washed with brine, dried over magnesium sulfate and evaporated under reduced pressure. The residue was purified by column chromatography (silica gel 150 g, 25–45% ethyl acetate in n-hexane) to give 4-(4-methoxypyridin-2-yl)-2-nitrobenzaldehyde (1.99 g).

$^1$H-NMR (CDCl$_3$): δ3.97(3H,s), 6.91(1H,dd,J=5.7 Hz,2.4 Hz), 7.35(1H,d,J=2.3 Hz), 8.05 (1H,d,J=8.0 Hz), 8.40(1H, dd,J=8.0 Hz,1.2 Hz), 8.59 (1H,d,J=5.7 Hz), 8.75(1H,d,J=1.8 Hz), 10.46(1H,s)

Preparation 74

To a suspension of sodium hydride (60% dispersion in mineral oil, 192 mg) in tetrahydrofuran (10 ml) was added a solution of diethyl cyanomethylphosphonate (0.777 ml) dropwise at 0° C., and the mixture was stirred at ambient temperature for 30 minutes. Then to the resultant mixture was added a solution of 4-(4-methoxypyridin-2-yl)-2-nitrobenzaldehyde (1.03 g) in tetrahydrofuran (20 ml) dropwise at 0° C., and the mixture was stirred at ambient temperature for 1 hour. The reaction mixture was poured into water and extracted with ethyl acetate. The organic layer was washed with brine, dried over sodium sulfate and evaporated under reduced pressure. The residue was triturated with diisopropyl ether, filtered and dried to give 4-(4-methoxypyridin-2-yl)-2-nitrocinnamonitrile (1.11 g) as a mixture of regioisomers.

$^1$H-NMR (CDCl3): δ3.95(3H,s), 5.7–6.0(1H,m), 6.88 (1H,dd,J=5.7 Hz,2.4 Hz), 7.31(1H,d,J=5.5 Hz), 7.7–8.1(2H, m), 8.3–8.5(1H,m), 8.57(1H,d,J=5.7 Hz), 8.7–8.9(1H,m)

EXAMPLE 96

To a suspension of 4-(4-methoxypyridin-2-yl)-2-nitrocinnamonitrile (308 mg) in ethanol (30 ml) was added tin (II) chloride dihydrate (1.41 g), and the mixture was refluxed for 30 minutes. Then to the solution was added hydrochloric acid (12N, 5 ml), and the mixture was refluxed for 6 hours. After cooling, the reaction mixture was poured into a saturated aqueous sodium hydrogencarbonate solution and extracted with dichloromethane. The organic layer was washed with brine, dried over sodium sulfate and evaporated under reduced pressure. The residue was purified by column chromatography (silica gel 150 g, 10% methanol in dichloromethane). The compound obtained was dissolved in ethyl acetate, and a solution of hydrogen chloride in 1,4-dioxane (4N, 1 ml) was added. The precipitate was collected by filtration and dried to give 2-amino-7-(4-methoxypyridin-2-yl)-quinoline dihydrochloride (77 mg).

$^1$H-NMR (DMSO-d$_6$): δ4.10(3H,s), 7.26(1H,d,J=9.3 Hz), 7.41(1H,dd,J=6.4 Hz,2.5 Hz), 7.84(1H,d,J=2.5 Hz), 8.12 (2H,s), 8.34(1H,s), 8.45(1H,d,J=9.4 Hz), 8.4–8.8(1H,broad s), 8.73(1H,d,J=6.4 Hz), 9.4–9.7(1H,broad s), 14.2–15.0 (1H,broad s)

Preparation 75

To a suspension of 2-bromo-4-methylpyridine (5.16 g), 4-methyl-3-nitrophenylboronic acid (7.06 g) and tetrakis (triphenylphosphine)-palladium (1.73 g) in 1,2-dimethoxyethane (100 ml) was added 2M aqueous solution of sodium carbonate (39 ml). The mixture was stirred at 80° C. for 12 hours under a nitrogen atmosphere, then cooled to room temperature and diluted with ethyl acetate. The organic layer was separated, washed with water and brine and dried over sodium sulfate. The solvent was evaporated under reduced pressure. 2-Propanol was added to the residue. The precipitate was collected by filtration and dried under reduced pressure to give 4-(4-methylpyridin-2-yl)-2-nitrotoluene (4.54 g).

$^1$H-NMR (CDCl$_3$): δ2.44(3H,s), 2.65(3H,s), 7.11(1H,d, J=4.3 Hz), 7.43(1H,d,J=8.0 Hz), 7.58(1H,s), 8.17(1H,dd,J= 8.0 Hz,1.9 Hz), 8.55(1H,d,J=5.0 Hz), 8.58(1H,d,J=1.9 Hz)

Preparation 76

To a solution of 4-(4-methylpyridin-2-yl)-2-nitrotoluene (3.42 g) in N,N-dimethylformamide (20 ml) was added N,N-dimethylformamide dimethyl acetal (2.59 ml), and the mixture was stirred at 150° C. for 18 hours under a nitrogen atmosphere. The reaction mixture was evaporated under reduced pressure, and the residue was dissolved in tetrahydrofuran (80 ml) and water (80 ml). Sodium metaperiodate (10.59 g) was added to the solution, and the mixture was stirred at ambient temperature for 4 hours. The reaction mixture was filtered, and the filtrate was extracted with ethyl acetate. The separated organic layer was washed with brine, dried over magnesium sulfate and evaporated under reduced pressure. The residue was purified by column chromatography (silica gel 75 g, 0–1% ethanol in dichloromethane) to give 4-(4-methylpyridin-2-yl)-2-nitrobenzaldehyde (3.58 g).

$^1$H-NMR (CDCl$_3$): δ2.48(3H,s), 7.20(1H,d,J=5.0 Hz), 7.68(1H,s), 8.05(1H,d,J=8.0 Hz), 8.42(1H,dd,J=8.0 Hz,1.6 Hz), 8.62(1H,d,J=5.0 Hz), 8.78(1H,d,J=1.6 Hz), 10.47(1H, s)

Preparation 77

To a suspension of sodium hydride (60% dispersion in mineral oil, 240 mg) in tetrahydrofuran (10 ml) was added a solution of diethyl cyanomethylphosphonate (0.971 ml) dropwise at 0° C., and the mixture was stirred at ambient temperature for 30 minutes. Then to the resultant mixture was added a solution of 4-(4-methylpyridin-2-yl)-2-nitrobenzaldehyde (1.21 g) in tetrahydrofuran (15 ml) dropwise at 0° C., and the mixture was stirred at ambient temperature for 1 hour. The reaction mixture was poured into water and extracted with ethyl acetate. The organic layer was washed with brine, dried over sodium sulfate and evaporated under reduced pressure. The residue was triturated with diisopropyl ether, filtered and dried to give 4-(4-methylpyridin-2-yl)-2-nitrocinnamonitrile (1.22 g) as a mixture of regioisomers.

$^1$H-NMR (CDCl$_3$): δ2.47(3H,s), 5.7–6.0(1H,m), 7.18(1H, d,J=5.1 Hz), 7.64(1H,s), 7.7–8.1(2H,m), 8.3–8.5(1H,m), 8.59(1H,d,J=5.1 Hz), 8.7–8.9(1H,m)

EXAMPLE 97

To a suspension of 4-(4-methylpyridin-2-yl)-2-nitrocinnamonitrile (1.32 g) in acetic acid (5 ml) and N,N-dimethylformamide (5 ml) was added iron powder (1.63 g), and the mixture was stirred at 100° C. for 3 hours. After cooling, the reaction mixture was poured into a saturated aqueous sodium hydrogencarbonate solution and extracted with dichloromethane. The organic layer was washed with brine, dried over sodium sulfate and evaporated under reduced pressure. The residue was purified by column chromatography (silica gel 50 g, 5–10% methanol in dichloromethane). The compound obtained was dissolved in ethyl acetate, and a solution of hydrogen chloride in 1,4-dioxane (4N, 1 ml) was added. The precipitate was collected by filtration and dried to give 2-amino-7-(4-methylpyridin-2-yl)quinoline dihydrochloride (482 mg).

$^1$H-NMR (DMSO-d$_6$): δ2.51(3H,s), 7.21(1H,d,J=9.3 Hz), 7.54(1H,d,J=5.1 Hz), 8.0–8.3(2H,m), 8.4–8.6(2H,m), 8.69 (1H,d,J=5.3 Hz), 9.44(1H,broad s), 14.61(1H,broad s)

Preparation 78

To a suspension of sodium hydride (60% dispersion in mineral oil, 101 mg) in tetrahydrofuran (10 ml) was added a solution of diethylphosphonoacetic acid ethyl ester (0.535 ml) dropwise at 0° C., and the mixture was stirred at 5° C. for 30 minutes. Then to the resultant mixture was added a solution of 4-(4-methoxypyridin-2-yl)-2-nitrobenzaldehyde (543 mg) in tetrahydrofuran (10 ml) dropwise at 0° C., and the mixture was stirred at ambient temperature for 1 hour. The reaction mixture was poured into water and extracted with ethyl acetate. The organic layer was washed with brine, dried over sodium sulfate and evaporated under reduced pressure. The residue was triturated with diisopropyl ether, filtered and dried to give 4-(4-methoxypyridin-2-yl)-2-nitrocinnamic acid ethyl ester (557 mg).

$^1$H-NMR (CDCl$_3$): δ1.35(3H,t,J=7.1 Hz), 3.95(3H,s), 4.30(2H,q,J=7.1 Hz), 6.43(1H,dd,J=15.8 Hz), 6.86(1H,dd, J=5.7 Hz,2.4 Hz), 7.30(1H,d,J=2.4 Hz), 7.74(1H,d,J=8.2 Hz), 8.13(1H,d,J=15.8 Hz), 8.28(1H,dd,J=8.0 Hz,1.6 Hz), 8.56(1H,d,J=5.7 Hz), 8.65(1H,d,J=1.6 Hz)

Preparation 79

To a suspension of 4-(4-methoxypyridin-2-yl)-2-nitrocinnamic acid ethyl ester (659 mg) in acetic acid (11 ml) was added iron powder (673 mg), and the mixture was stirred at 100° C. for 2 hours. After cooling, the reaction mixture was poured into a saturated aqueous sodium hydrogencarbonate solution and filtered, and the filtrate was extracted with dichloromethane-methanol (5:1). The organic layer was washed with brine, dried over sodium sulfate and evaporated under reduced pressure. The residue was dissolved in ethanol (5 ml). To the solution was added a solution of sodium methoxide in methanol (28%, 3 ml), and the mixture was refluxed for 2 hours. After cooling, the reaction mixture was poured into a saturated aqueous ammonium chloride solution and extracted with dichloromethane. The organic layer was washed with brine, dried over sodium sulfate and evaporated under reduced pressure to give 7-(4-methoxypyridin-2-yl)-2-quinolone (140 mg).

$^1$H-NMR (DMSO-d$_6$): δ3.93(3H,s), 6.53(1H,d,J=9.4 Hz), 7.01(1H,dd,J=5.7 Hz,2.3 Hz), 7.51(1H,d,J=2.3 Hz), 7.74 (1H,d,J=8.3 Hz), 7.88(1H,d,J=8.3 Hz), 8.08(1H,s), 8.52(1H, d,J=5.7 Hz), 11.82(1H,broad s)

Preparation 80

A suspension of 7-(4-methoxypyridin-2-yl)-2-quinolone (130 mg) in phosphorus oxychloride (5 ml) was refluxed for 2 hours. The mixture was evaporated under reduced pressure. The residue was poured into a saturated aqueous sodium hydrogencarbonate solution and extracted with dichloromethane. The organic layer was washed with brine, dried over sodium sulfate and evaporated under reduced pressure to give 2-chloro-7-(4-methoxypyridin-2-yl) quinoline (140mg).

$^1$H-NMR (DMSO-d$_6$): δ3.97(3H,s), 7.03(1H,dd,J=5.7 Hz,2.4 Hz), 7.63(1H,d,J=8.4 Hz), 7.77(1H,d,J=2.4 Hz), 8.15 (1H,d,J=8.4 Hz), 8.4–8.6(2H,m), 8.56(1H,d,J=5.7 Hz), 8.69 (1H,s)

EXAMPLE 98

To a solution of methylamine in methanol (40% w/w, 5 ml) was added 2-chloro-7-(4-methoxypyridin-2-yl) quinoline (140 mg). The mixture was heated in a steel autoclave at 120° C. for 16 hours. After cooling, the solvent was evaporated under reduced pressure. The residue was purified by column chromatography (silica gel 25 g, 5% methanol in dichloromethane). The compound obtained was dissolved in ethyl acetate, and a solution of hydrogen chloride in 1,4-dioxane (4N, 1 ml) was added. The precipitate was collected by filtration and dried to give 7-(4-methoxypyridin-2-yl)-2-methylaminoquinoline dihydrochloride (106 mg).

$^1$H-NMR (DMSO-d$_6$): δ3.19(3H,d,J=4.5 Hz), 4.06(3H,s), 7.2–7.4(2H,m), 7.72(1H,s), 8.0–8.2(2H,m), 8.32(1H,d,J=9.5 Hz), 8.70(1H,d,J=6.2 Hz), 8.88(1H,s), 10.1–10.3(1H,broad s)

Preparation 81

A suspension of 4-(4-methylpyridin-2-yl)-2-nitrobenzaldehyde (203 mg) and 2-(triphenylphosphoranylidene)propionitrile (0.45 g) in toluene (10 ml) was refluxed for 3 hours. After cooling, to the reaction mixture were added magnesium sulfate and silica gel (10 g), and the suspension was stirred for 30 minutes. The solid was removed by filtration and washed with toluene (10 ml) three times. The combined filtrate was evaporated under reduced pressure to give 2-(4-(4-methylpyridin-2-yl)-2-nitrobenzylidene)propionitrile (221 mg) as a mixture of regioisomers.

$^1$H-NMR (CDCl$_3$): δ2.00 and 2.24(3H), 2.49(3H,s), 7.1–7.3(1H,m), 7.4–7.8(3H,m), 8.2–8.4(1H,m), 8.60(1H,d, J=5.0 Hz), 8.81(1H,d,J=1.8 Hz)

EXAMPLE 99

To a suspension of 2-(4-(4-methylpyridin-2-yl)-2-nitrobenzylidene)-propionitrile (221 mg) in ethanol (30 ml) was added tin (II) chloride dihydrate (1.25 g), and the mixture was refluxed for 30 minutes. Then to the solution was added hydrochloric acid (12N, 5 ml), and the mixture was refluxed for 6 hours. After cooling, the reaction mixture was poured into a saturated aqueous sodium hydrogencarbonate solution and extracted with dichloromethane. The organic layer was washed with brine, dried over sodium sulfate and evaporated under reduced pressure. The residue was purified by column chromatography (silica gel 25 g, 10% methanol in dichloromethane). The compound obtained was dissolved in ethyl acetate, and a solution of hydrogen chloride in 1,4-dioxane (4N, 1 ml) was added. The precipitate was collected by filtration and dried to give 2-amino-3-methyl-7-(4-methylpyridin-2-yl)quinoline dihydrochloride (57 mg).

$^1$H-NMR (DMSO-d$_6$): δ2.34(3H,s), 2.49(3H,s), 7.47(1H, d,J=5.3 Hz), 7.99(1H,d,J=8.4 Hz), 8.06(1H,s), 8.14(1H,d,J= 8.4 Hz), 8.32(1H,s), 8.40(1H,s), 8.67(1H,d,J=5.3 Hz), 8.74 (1H,s), 14.4–14.6(1H,broad s)

Preparation 82

To a suspension of 4-(4-methylpyridin-2-yl)-2-nitrobenzaldehyde (242 mg), ethyleneglycol (1.2 ml) and magnesium sulfate (1.0 g) in toluene (5 ml) was added p-toluenesulfonic acid monohydrate (209 mg), and the resultant suspension was refluxed for 5 hours. After cooling, the mixture was poured into 0.1N aqueous sodium hydroxide and extracted with ethyl acetate. The organic layer was washed with brine, dried over magnesium sulfate and evaporated under reduced pressure. The residue was purified by column chromatography (silica gel 25 g, 25% ethyl acetate in n-hexane) to give 2-(4-(4-methylpyridin-2-yl)-2-nitrophenyl)-1,3-dioxolane (215 mg).

$^1$H-NMR (CDCl$_3$): δ2.45(3H,s), 4.0–4.2(4H,m), 6.54(1H, s), 7.14(1H,d,J=4.3 Hz), 7.61(1H,s), 7.88(1H,d,J=8.2 Hz), 8.26(1H,dd,J=8.2 Hz, 1.8 Hz), 8.5–8.7(2H,m)

Preparation 83

A suspension of 2-(4-(4-methylpyridin-2-yl)-2-nitrophenyl)-1,3-dioxolane (0.201 g) in ethanol (4 ml) and tetrahydrofuran (2 ml) was hydrogenated over palladium on carbon (10% w/w, 50% wet, 0.05 g) under a hydrogen atmosphere for 4 hours. The catalyst was filtered off, and the filtrate was evaporated under reduced pressure. The residue was dissolved in dichloromethane (7 ml). To the solution were added N,N'-bis(tert-butoxycarbonyl)thiourea (232 mg), 1-methyl-2-chloropyridinium iodide (233 mg) and diisopropylethylamine (0.282 ml), and the mixture was stirred at ambient temperature for 18 hours. The resultant suspension was diluted with dichloromethane and washed with water and brine. The separated organic layer was dried over sodium sulfate and evaporated under reduced pressure. The residue was purified by column chromatography (silica gel 25 g, n-hexane:ethyl acetate=1:1) to give N,N'-bis(tert-butoxycarbonyl)-N"-(2-(1,3-dioxolan-2-yl)-5-(4-methylpyridin-2-yl)phenyl)guanidine (237 mg).

$^1$H-NMR (CDCl$_3$): δ1.4–1.6(18H,m), 2.41(3H,s), 4.0–4.3 (4H,m), 5.78(1H,s), 7.06(1H,d,J=5.0 Hz), 7.48(1H,d,J=8.0 Hz), 7.63(1H,s), 7.85(1H,dd,J=8.0 Hz, 1.7 Hz), 8.53(1H,d, J=5.0 Hz), 8.83(1H,s), 10.69(1H,s), 11.68(1H,s)

EXAMPLE 100

To a solution of N,N'-bis(tert-butoxycarbonyl)-N"-(2-(1, 3-dioxolan-2-yl)-5-(4-methylpyridin-2-yl)phenyl)guanidine (190 mg) in ethanol (2 ml) was added hydrochloric acid (36%, 1 ml), and the mixture was stirred for 6 hours. The solvent was evaporated under reduced pressure. To the residue was added 5% ethanol in ethyl acetate (50 ml), and the precipitate was collected by filtration and dried under reduced pressure to give 2-amino-7-(4-methylpyridin-2-yl)quinazoline dihydrochloride (92 mg).

¹H-NMR (DMSO-d₆): δ2.49(3H,s), 7.47(1H,d,J=5.2 Hz), 8.10(1H,s), 8.24(2H,s), 8.41(1H,s), 8.68(1H,d,J=5.2 Hz), 9.60(1H,s)

Preparation 84

To a suspension of 4-(4-methoxypyridin-2-yl)-2-nitrobenzaldehyde (413 mg), ethyleneglycol (0.266 ml) and magnesium sulfate (1.0 g) in toluene (10 ml) was added p-toluenesulfonic acid monohydrate (334 mg), and the resultant suspension was refluxed for 5 hours. After cooling, the mixture was poured into 0.1N aqueous sodium hydroxide and extracted with ethyl acetate. The organic layer was washed with brine, dried over potassium carbonate and evaporated under reduced pressure. The residue was triturated with diisopropyl ether. The solid was collected by filtration, washed with diisopropyl ether and dried under reduced pressure to give 2-(4-(4-methoxypyridin-2-yl)-2-nitrophenyl)-1,3-dioxolane (412 mg).

¹H-NMR (CDCl₃): δ3.93(3H,s), 4.0–4.2(4H,m), 6.54(1H, s), 6.85(1H,dd,J=5.9 Hz,2.4 Hz), 7.2–7.3(1H,m), 7.87(1H, d,J=7.1 Hz), 8.23(1H,dd,J=8.1 Hz,1.8 Hz), 8.5–8.7(2H,m)

Preparation 85

A suspension of 2-(4-(4-methoxypyridin-2-yl)-2-nitrophenyl)-1,3-dioxolane (0.3 g) in ethanol (3 ml) and tetrahydrofuran (3 ml) was hydrogenated over palladium on carbon (10% W/W, 50% wet, 0.15 g) under a hydrogen atmosphere for 1 hour. The catalyst was filtered off, and the filtrate was evaporated under reduced pressure. The residue was dissolved in dichloromethane (10 ml). To the solution were added N,N'-bis(tert-butoxycarbonyl)thiourea (329 mg), 1-methyl-2-chloropyridinium iodide (329 mg) and diisopropylethylamine (0.397 ml), and the mixture was stirred at ambient temperature for 18 hours. The resultant suspension was diluted with dichloromethane and washed with water and brine. The separated organic layer was dried over sodium sulfate and evaporated under reduced pressure. The residue was purified by column chromatography (silica gel 25 g, n-hexane:ethyl acetate=2:1) to give N,N'-bis(tert-butoxycarbonyl)-N"-(2-(1,3-dioxolan-2-yl)-5-(4-methoxypyridin-2-yl)phenyl)guanidine (419 mg).

¹H-NMR (CDCl₃): δ1.4–1.6(18H,m), 3.91(3H,s), 4.0–4.3 (4H,m), 5.79(1H,s), 6.78(1H,dd,J=5.7 Hz,2.4 Hz), 7.32(1H, d,J=2.3 Hz), 7.49(1H,d,J=8.1 Hz), 7.82(1H,dd,J=8.0 Hz,1.7 Hz), 8.49(1H,d,J=5.7 Hz), 8.71(1H,s), 10.67(1H,s), 11.70 (1H,s)

EXAMPLE 101

To a solution of N,N'-bis(tert-butoxycarbonyl)-N"-(2-(1, 3-dioxolan-2-yl)-5-(4-methoxylpyridin-2-yl)phenyl) guanidine (200 mg) in ethanol (2 ml) was added hydrochloric acid (36%, 1 ml), and the mixture was stirred for 18 hours. The solvent was evaporated under reduced pressure. To the residue was added 5% ethanol in ethyl acetate (50 ml), and the precipitate was collected by filtration and dried under reduced pressure to give 2-amino-7-(4-methoxypyridin-2-yl)quinazoline dihydrochloride (89 mg).

¹H-NMR (DMSO-d₆): δ4.05(3H,s), 7.34(1H,d,J=5.2 Hz), 7.7–8.1(3H,m), 8.2–8.4(2H,m), 8.70(1H,d,J=6.1 Hz), 9.60 (1H,s)

Preparation 86

To a solution of 4-tert-butyldimethylsilyloxybromobenzene (11.49 g) in tetrahydrofuran (100 ml) was added a solution of n-butyllithium in n-hexane (1.59M, 32.7 ml) dropwise at −55° C. under a nitrogen atmosphere, and the mixture was stirred for 1 hour at −60° C. To the reaction mixture was added triisopropyl borate (12.84 ml), and the mixture was stirred at −60° C. for 1 hour. The reaction mixture was warmed to ambient temperature, poured into a saturated aqueous ammonium chloride solution and extracted with ethyl acetate. The separated organic layer was washed with brine, dried over magnesium sulfate and evaporated under reduced pressure. The solid was triturated with n-hexane, filtered and washed with n-hexane to give 4-tert-butyldimethylsilyloxyphenylboronic acid (7.45 g).

¹H-NMR (CDCl₃): δ0.23(6H,s), 1.01(9H,s), 6.94(2H,d, J=8.5 Hz), 8.10(2H,d,J=8.5 Hz)

Preparation 87

To a suspension of 4-tert-butyldimethylsilyloxyphenylboronic acid (3.28 g), 2-bromo-4-methoxypyridine (1.88 g) and tetrakis(triphenylphosphine)palladium (578 mg) in 1,2-dimethoxyethane (30 ml) was added 2M aqueous solution of sodium carbonate (13 ml). The mixture was stirred at 80° C. for 3 hours under a nitrogen atmosphere, then cooled to room temperature and diluted with ethyl acetate. The organic layer was separated, washed with water and brine and dried over sodium sulfate. The residue was dissolved in ethanol (15 ml) and 1N aqueous hydrochloric acid (30 ml) and stirred for 12 hours at ambient temperature. The solvent was evaporated under reduced pressure. The residue was triturated with 2-propanol, filtered and washed with diisopropyl ether to give 4-(4-methoxypyridin-2-yl)phenol hydrochloride (2.38 g).

¹H-NMR (DMSO-d₆): δ4.14(3H,s), 4.8–5.2(1H,broad s), 7.02(2H,d,J=8.8 Hz), 7.4–7.8(2H,m), 7.76(1H,d,J=2.6 Hz), 7.99(2H,d,J=8.8 Hz), 8.59(1H,d,J=6.9 Hz)

Preparation 88

To a suspension of 4-(4-methoxypyridin-2-yl)phenol hydrochloride (500 mg) in acetic acid (5 ml) was added fuming nitric acid (0.09 ml), and the mixture was stirred at 40° C. for 1 hour. The reaction mixture was poured into a saturated aqueous sodium hydrogencarbonate solution and extracted with ethyl acetate. The separated organic layer was washed with water and brine, dried over sodium sulfate and evaporated under reduced pressure. The residue was triturated with diisopropyl ether, filtered, washed with diisopropyl ether and dried under reduced pressure to give 4-(4-methoxypyridin-2-yl)-3-nitrophenol (293 mg).

¹H-NMR (DMSO-d₆): δ3.91(3H,s), 6.95(1H,dd,J=5.7 Hz,2.4 Hz), 7.22(1H,d,J=8.8 Hz), 7.5–7.7(3H,m), 8.29(1H, dd,J=8.8 Hz,2.3 Hz), 8.46(1H,d,J=5.7 Hz), 8.62(1H,d,J=2.3 Hz), 11.93(1H,s)

EXAMPLE 102

A suspension of 4-(4-methoxypyridin-2-yl)-3-nitrophenol (250 mg) in ethanol (5 ml) and tetrahydrofuran (2.5 ml) was hydrogenated over palladium on carbon (10% w/w, 50% wet, 125 mg) under a hydrogen atmosphere for 2 hours. The catalyst was filtered off, and to the filtrate was added cyanogen bromide (129 mg). The solution was stirred at ambient temperature for 18 hours, then evaporated under reduced pressure. The residue was purified by column chromatography (silica gel 15 g, 4–6% methanol in dichloromethane). The compound obtained was dissolved in ethyl acetate, and a solution of hydrogen chloride in 1,4-dioxane (4N, 1 ml) was added. The precipitate was collected by filtration and dried to give 2-amino-5-(4-methoxypyridin-2-yl)benzoxazole dihydrochloride (182 mg).

¹H-NMR (DMSO-d₆): δ4.17(3H,s), 7.48(1H,dd,J=6.9 Hz,2.6 Hz), 7.67(1H,d,J=8.4 Hz), 7.80(1H,dd,J=8.5 Hz,2.6 Hz),7.99(1H,d,J=1.7 Hz), 8.3–8.6(2H,broad s), 8.67(1H,d, J=6.9 Hz)

Preparation 89

To a solution of methylamine in tetrahydrofuran (2M, 11 ml) was added 1-fluoro-4-(4-methoxypyridin-2-yl)-2-nitrobenzene (289 mg). The mixture was stirred at ambient temperature for 2 hours and poured into water. The precipitate was collected by filtration and dried to give 1-methylamino-4-(4-methoxypyridin-2-yl)-2-nitrobenzene (280 mg).

$^1$H-NMR (CDCl$_3$): δ3.10(1H,d,J=5.1 Hz), 3.94(3H,s), 6.77(1H,dd,J=5.8 Hz,2.4 Hz), 6.96(1H,d,J=9.1 Hz), 7.21 (1H,d,J=2.3 Hz), 8.1–8.3(1H,broad), 8.27(1H,dd,J=9.1 Hz,1.9 Hz), 8.48(1H,d,J=5.8 Hz), 8.78(1H,d,J=2.2 Hz)

EXAMPLE 103

A suspension of 1-methylamino-4-(4-methoxypyridin-2-yl)-2-nitrobenzene (130 mg) in ethanol (5 ml) was hydrogenated over palladium on carbon (10% w/w, 50% wet, 46 mg) under a hydrogen atmosphere for 3 hours. The catalyst was filtered off, and to the filtrate was added cyanogen bromide (69 mg). The solution was stirred at ambient temperature for 18 hours, then evaporated under reduced pressure. The residue was purified by column chromatography (silica gel 25 g, dichloromethane:methanol:aqueous ammonia=100:10:1). The compound obtained was dissolved in-ethyl acetate, and a solution of hydrogen chloride in 1,4-dioxane (4N, 1 ml) was added. The precipitate was collected by filtration and dried to give 2-amino-5-(4-methoxypyridin-2-yl)-1-methylbenzimidazole dihydrochloride (123 mg).

$^1$H-NMR (DMSO-d$_6$): δ3.71(3H,s), 4.13(3H,s), 7.42(1H, dd,J=6.7 Hz,2.5 Hz), 7.74(1H,d,J=8.3 Hz), 7.82(1H,d,J=2.5 Hz), 8.02(1H,d,J=8.5 Hz), 8.11(1H,s), 8.67(1H,d,J=6.7 Hz), 9.03(2H,s)

Preparation 90

To a solution of ethylamine in ethanol (20% w/w, 2 ml) was added 1-fluoro-4-(4-methoxypyridin-2-yl)-2-nitrobenzene (200 mg). The mixture was stirred at ambient temperature for 4 hours and poured into water. The precipitate was collected by filtration and dried to give 1-ethylamino-4-(4-methoxypyridin-2-yl)-2-nitrobenzene (206 mg).

$^1$H-NMR (CDCl3): δ1.40(3H,t,J=7.2 Hz), 3.40(2H,m), 3.92(3H,s), 6.75(1H,dd,J=5.8 Hz,2.4 Hz), 6.96(1H,d,J=9.1 Hz), 7.19(1H,d,J=2.3 Hz), 8.1–8.3(1H,broad), 8.20(1H,dd, J=9.1 Hz,2.0 Hz), 8.47(1H,d,J=5.8 Hz), 8.77(1H,d,J=2.2 Hz)

EXAMPLE 104

A suspension of 1-ethylamino-4-(4-methoxypyridin-2-yl)-2-nitrobenzene (180 mg) in ethanol (2 ml) and tetrahydrofuran (2 ml) was hydrogenated over palladium on carbon (10% w/w, 50% wet, 90 mg) under a hydrogen atmosphere for 1 hour. The catalyst was filtered off, and to the filtrate was added cyanogen bromide (91 mg). The solution was stirred at ambient temperature for 18 hours, then evaporated under reduced pressure. The residue was purified by column chromatography (silica gel 25 g, dichloromethane:methanol:aqueous ammonia=100:10:1). The compound obtained was dissolved in ethyl acetate, and a solution of hydrogen chloride in 1,4-dioxane (4N, 1 ml) was added. The precipitate was collected by filtration and dried to give 2-amino-1-ethyl-5-(4-methoxypyridin-2-yl)benzimidazole dihydrochloride (171 mg).

$^1$H-NMR (DMSO-d$_6$): δ1.30(3H,t,J=6.9 Hz), 4.12(3H,s), 4.2–4.4(2H,m), 7.42(1H,d,J=6.7 Hz), 7.7–7.9(2H,m), 8.02 (1H,d,J=8.5 Hz), 8.11(1H,s), 8.67(1H,d,J=6.7 Hz), 9.07(2H, s)

Preparation 91

To a solution of 1-fluoro-4-(4-methoxypyridin-2-yl)-2-nitrobenzene (200 mg) and triethylamine (0.135 ml) in tetrahydrofuran (2 ml) was added aniline (2 ml). The mixture was stirred under reflux for 6 hours and evaporated under reduced pressure. The residue was dissolved in ethyl acetate and washed with water and brine, dried over magnesium sulfate and evaporated under reduced pressure. The precipitate was triturated with diisopropyl ether, collected by filtration and dried to give 4-(4-methoxypyridin-2-yl)-2-nitro-N-phenylaniline (235 mg).

$^1$H-NMR (CDCl3): δ3.95(3H,s), 6.79(1H,dd,J=5.8 Hz,2.4 Hz), 7.1–7.5(7H,m), 8.14(1H,dd,J=9.0 Hz,2.0 Hz), 8.50(1H, d,J=5.8 Hz), 8.81(1H,d,J=2.2 Hz), 9.65(1H,s)

EXAMPLE 105

A suspension of 4-(4-methoxypyridin-2-yl)-2-nitro-N-phenylaniline (205 mg) in ethanol (2 ml) and tetrahydrofuran (2 ml) was hydrogenated over palladium on carbon (10% w/w, 50% wet, 103 mg) under a hydrogen atmosphere for 2 hours. The catalyst was filtered off, and to the filtrate was added cyanogen bromide (88 mg). The solution was stirred at ambient temperature for 18 hours, then evaporated under reduced pressure. The residue was purified by column chromatography (silica gel 25 g, dichloromethane:methanol aqueous ammonia=100:10:1). The compound obtained was dissolved in ethyl acetate, and a solution of hydrogen chloride in 1,4-dioxane (4N, 1 ml) was added. The precipitate was collected by filtration and dried to give 2-amino-5-(4-methoxypyridin-2-yl)-1-phenyl-benzimidazole dihydrochloride (183 mg).

$^1$H-NMR (DMSO-d$_6$): δ4.12(3H,s), 7.14(1H,d,J=8.5 Hz), 7.42(1H,dd,J=6.7 Hz,2.4 Hz), 7.6–7.9(6H,m), 7.92(1H,dd, J=8.5 Hz,1.7Hz), 8.21 (1H,d,J=1.44 Hz), 8.68(1H,d,J=6.7 Hz), 8.86(2H,s)

Preparation 92

To a solution of cyanamide (101 mg) in N,N-dimethylformamide (15 ml) was added sodium hydride (60% dispersion in mineral oil, 90 mg), and the resultant suspension was stirred at ambient temperature for 30 minutes. To the suspension was added 1-chloro-4-(4-methoxypyridin-2-yl)-2-nitrobenzene (264 mg), and the mixture was stirred at 80° C. for 4 hours. The mixture was poured into a saturated aqueous ammonium chloride solution and extracted with ethyl acetate three times. The combined organic layer was washed with brine, dried over sodium sulfate and evaporated under reduced pressure. The residue was triturated with diisopropyl ether, filtered and dried under reduced pressure to give N-cyano-4-(4-methoxypyridin-2-yl)-2-nitroaniline (241 mg).

$^1$H-NMR (CDCl$_3$): δ3.95(3H,s), 6.84(1H,dd,J=5.7 Hz,2.4 Hz), 7.2–7.3(1H,m), 7.61(1H,d,J=8.7 Hz), 8.39(1H,dd,J=8.7 Hz,2.0 Hz), 8.54(1H,d,J=5.7 Hz), 8.91(1H,d,J=2.0 Hz), 9.51 (1H,broad s)

EXAMPLE 106

A suspension of N-cyano-4-(4-methoxypyridin-2-yl)-2-nitroaniline (200 mg) in ethanol (10 ml) was hydrogenated over Raney-nickel (500 mg) under a hydrogen atmosphere for 12 hours. The catalyst was filtered off, and the filtrate was evaporated under reduced pressure. The residue was purified by column chromatography (silica gel 20 g, dichloromethane:methanol:aqueous ammonia=100:10:1). The compound obtained was dissolved in ethyl acetate, and a solution of hydrogen chloride in 1,4-dioxane (4N, 1 ml) was added. The precipitate was collected by filtration and dried to give 2-amino-5-(4-methoxypyridin-2-yl)benzimidazole dihydrochloride (142 mg).

$^1$H-NMR (DMSO-d$_6$): δ4.14(3H,s), 7.4–7.5(1H,m), 7.58 (1H,d,J=8.4 Hz), 7.81(1H,d,J=2.5 Hz), 7.92(1H,dd,J=8.4 Hz,1.8 Hz), 8.07(1H,d,J=1.4 Hz), 8.68(1H,d,J=6.8 Hz), 8.83 (2H,s)

EXAMPLE 107

To a suspension of N-(2-fluoro-5-(4-methoxypyridin-2-yl)phenyl)-thiourea (0.104 g) in dimethyl sulfoxide (5 ml) was added a sodium hydride (60% dispersion in mineral oil ,15.4 mg), and the mixture was stirred at 100° C. for 5 hours. The mixture was diluted with ethyl acetate and washed with water three times and brine. The separated organic layer was dried over sodium sulfate and evaporated under reduced pressure. The residue was purified by column chromatography (silica gel 10 g, 5% methanol in dichloromethane). The compound obtained was dissolved in ethyl acetate, and a solution of hydrogen chloride in 1,4-dioxane (4N, 1 ml) was added. The precipitate was collected by filtration and dried under reduced pressure to give 2-amino-5-(4-methoxypyridin-2-yl)benzothiazole dihydrochloride (46 mg).

$^1$H-NMR (DMSO-d$_6$): δ4.15(3H,s), 7.47(1H,d,J=6.8 Hz,2.6 Hz), 7.76(1H,dd,J=8.3 Hz,1.7 Hz), 7.87(1H,d,J=2.6 Hz), 8.01(1H,d,J=8.3 Hz), 8.06(1H,d,J=1.7 Hz), 8.3–8.8 (2H,m), 8.69(1H,d,J=6.8 Hz)

What is claimed is:

1. A compound of the formula wherein

R$^1$ and R$^2$ are the same or different and each is hydrogen, lower alkyl, lower alkoxy, cyano, lower alkoxycarbonyl, carboxy, lower haloalkyl, hydroxy (lower)alkyl, hydroxy, nitro, amino, mono or di(lower) alkylamino, protected hydroxy or lower alkyl substituted by protected hydroxy;

X is a single bond or a group of the formula selected from the group consisting of $$-O-, \quad -CH_2-, \quad -\overset{O}{\underset{\parallel}{C}}-, \quad -\overset{OH}{\underset{|}{CH}}-,$$

$$-NH-CH_2- \quad \text{and} \quad -\overset{NHR^4}{\underset{|}{CH}}-,$$

wherein R$^4$ is hydrogen or acyl;

ring A is heterocycle or arylene wherein said heterocycle and arylene may be substituted by suitable substituent (s) selected from the group consisting of lower alkyl, lower alkoxy, halogen and guanidino which may be substituted by suitable substituent(s); and R$^3$ is a group of the formula selected from the group consisting of $$-N=\overset{R^5}{\underset{}{C}}-\overset{R^6}{\underset{R^7}{N}}, \quad -\overset{}{\underset{H}{N}}-\overset{S}{\underset{\parallel}{C}}-\overset{R^6}{\underset{R^7}{N}} \quad \text{and} \quad -NH-R^8$$

wherein R$^5$ is hydrogen, lower alkyl, lower alkylthio, amino which may be substituted by suitable substituent(s) or aromatic heterocyclic group, or when $$R^3 \text{ is } -N=\overset{R^5}{\underset{}{C}}-\overset{R^6}{\underset{R^7}{N}}, \quad -\underset{}{\bigcirc}-N=\overset{R^5}{\underset{}{C}}-$$

may form a bicyclic group selected from the group consisting of wherein said bicyclic group may be substituted by suitable substituent(s) selected from the group consisting of lower alkyl and aryl, R$^6$ and R$^7$ are the same or different and each is hydrogen, lower alkyl, cyano, amino, hydroxy, acyl or amidino which may be substituted by suitable substituent(s), and R$^8$ is thiazolinyl or pyridyl, or a pharmaceutically acceptable salt thereof.

2. The compound of claim 1 wherein R$^1$ and R$^2$ are the same or different and each is hydrogen, lower alkyl, lower alkoxy, cyano, lower alkoxycarbonyl, carboxy, lower haloalkyl, hydroxy(lower)alkyl, hydroxy, nitro, amino or mono or di(lower)alkylamino, or a pharmaceutically acceptable salt thereof.

3. The compound of claim 1 wherein ring A is a ring selected from the group consisting of wherein said ring A may be substituted by suitable substituent(s) selected from the group consisting of lower alkyl, lower alkoxy, halogen and guanidino, or a pharmaceutically acceptable salt thereof.

4. The compound of claim 1 wherein $R^3$ is

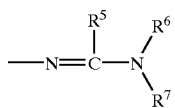

wherein $R^5$, $R^6$ and $R^7$ are as defined in claim 1, or a pharmaceutically acceptable salt thereof.

5. The compound of claim 4 wherein $R^5$ is hydrogen, lower alkyl, lower alkylthio, amino, mono or di(lower)alkylamino, acylamino, cyanoamino or 5-membered aromatic heteromonocyclic group containing sulfur atom or oxygen atom, or

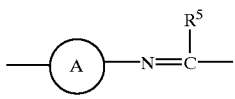

may form a bicyclic group selected from the group consisting of

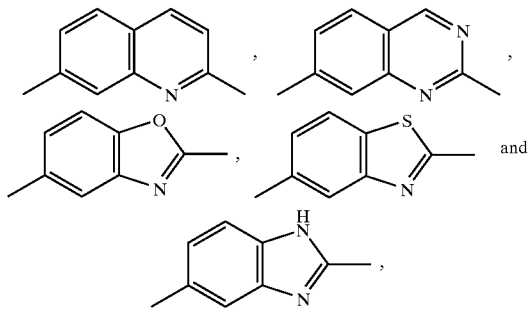

wherein said bicyclic group may be substituted by suitable substituent(s) selected from the group consisting of lower alkyl and aryl, and $R^6$ and $R^7$ are the same or different and each is hydrogen, lower alkyl, cyano, amino, hydroxy or amidino which may be substituted by suitable substituent(s) selected from the group consisting of lower alkyl and cyano, or a pharmaceutically acceptable salt thereof.

6. A pharmaceutical composition comprising the compound of claim 1 or a pharmaceutically acceptable salt thereof in admixture with a pharmaceutically acceptable carrier.

7. A method of inhibiting NOS-mediated diseases comprising therapeutically administering a pharmaceutical composition comprising said compound of claim 1 or a pharmaceutically acceptable salt thereof.

8. A method of treating a NOS-mediated disease comprising therapeutically administering a pharmaceutical composition comprising said compound of claim 1 or a pharmaceutically acceptable salt thereof.

9. The method as claimed in claim 8, wherein said NOS-mediated disease is selected from the group consisting of adult respiratory distress syndrome, myocarditis, synovitis, septic shock, insulin-dependent diabetes mellitus, ulcerative colitis, cerebral infarction, rheumatoid arthritis, osteoarthritis, osteoperosis, systemic lupus erythematosus, rejection by organ transplantation, asthma, pain, and ulcer.

10. A method of inhibiting nitric oxide synthase comprising administering said compound of claim 1.

11. The method of claim 10, wherein said compound is selected from the group consisting of 2-guanidino-4-methyl-5-(4-methoxypyridin-2-yl)thiazole, (5-(4-methoxypyridin-2-yl)-2-methylphenyl)guanidine dihydrochloride, N-(3-(4-methoxypyridin-2-yl)phenyl)-S-ethylisothiourea dihydrochloride, 2-amino-7-(4-methoxypyridin-2-yl)quinoline dihydrochloride, 2-amino-7-(4-methylpyridin-2-yl)quinoline dihydrochloride, and 7-(4-methoxypyridin-2-yl)-2-methylaminoquinoline dihydrochloride.

* * * * *